United States Patent
Serrano-Brizuela et al.

(10) Patent No.: US 10,744,119 B1
(45) Date of Patent: Aug. 18, 2020

(54) INHIBITORS OF THE MALARIAL GST

(71) Applicants: Adelfa E. Serrano-Brizuela, San Juan, PR (US); Emilee E. Colón-Lorenzo, San Juan, PR (US); Jürgen Bosh, Baltimore, MD (US); Daisy Colón-López, Baltimore, MD (US)

(72) Inventors: Adelfa E. Serrano-Brizuela, San Juan, PR (US); Emilee E. Colón-Lorenzo, San Juan, PR (US); Jürgen Bosh, Baltimore, MD (US); Daisy Colón-López, Baltimore, MD (US)

(73) Assignee: University of Puerto Rico, San Juan, PR (US)

( * ) Notice: Subject to any disclaimer, the term of this patent is extended or adjusted under 35 U.S.C. 154(b) by 47 days.

(21) Appl. No.: 14/970,515

(22) Filed: Dec. 15, 2015

Related U.S. Application Data

(60) Provisional application No. 62/091,637, filed on Dec. 15, 2014.

(51) Int. Cl.
| | |
|---|---|
| *A61K 31/4184* | (2006.01) |
| *A61K 31/166* | (2006.01) |
| *A61P 33/06* | (2006.01) |
| *A61K 31/426* | (2006.01) |
| *A61K 31/4375* | (2006.01) |
| *A61K 31/4439* | (2006.01) |
| *A61K 31/47* | (2006.01) |
| *A61K 31/4709* | (2006.01) |
| *A61K 31/506* | (2006.01) |
| *A61K 31/522* | (2006.01) |
| *A61K 31/53* | (2006.01) |
| *A61K 31/5377* | (2006.01) |

(52) U.S. Cl.
CPC ........ *A61K 31/4184* (2013.01); *A61K 31/166* (2013.01); *A61K 31/426* (2013.01); *A61K 31/4375* (2013.01); *A61K 31/4439* (2013.01); *A61K 31/47* (2013.01); *A61K 31/4709* (2013.01); *A61K 31/506* (2013.01); *A61K 31/522* (2013.01); *A61K 31/53* (2013.01); *A61K 31/5377* (2013.01); *A61P 33/06* (2018.01)

(58) Field of Classification Search
CPC .............. A61K 31/4184; A61K 31/166; A61K 31/426; A61K 31/4375; A61K 31/4439; A61K 31/47; A61K 31/4709; A61K 31/506; A61K 31/522; A61K 31/53; A61K 31/5377; A61P 33/06
See application file for complete search history.

*Primary Examiner* — Kortney L. Klinkel
*Assistant Examiner* — William Y Lee
(74) *Attorney, Agent, or Firm* — Hoglund & Pamias, PSC; Robert J. Rios

(57) ABSTRACT

A compound to inhibit a glutathione S-transferase (GST) enzyme activity having formula (I). The compound having formula (I) is an antimalarial compound that inhibits the growth of the *Plasmodium* spp parasites. The compound of the present invention inhibits the growth of a malarial parasite by 50%.

6 Claims, 33 Drawing Sheets
Specification includes a Sequence Listing.

FIG. 1

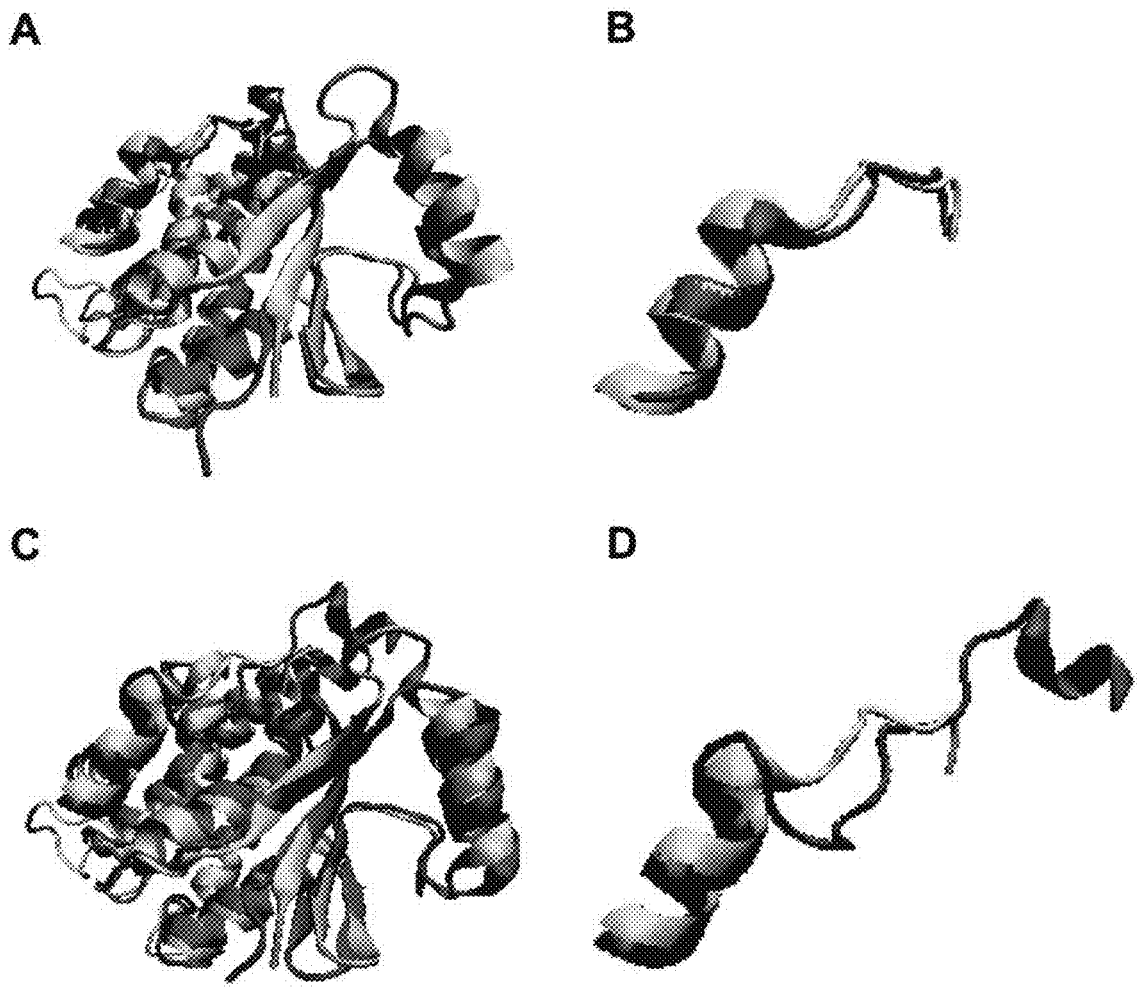
FIG. 4A-D

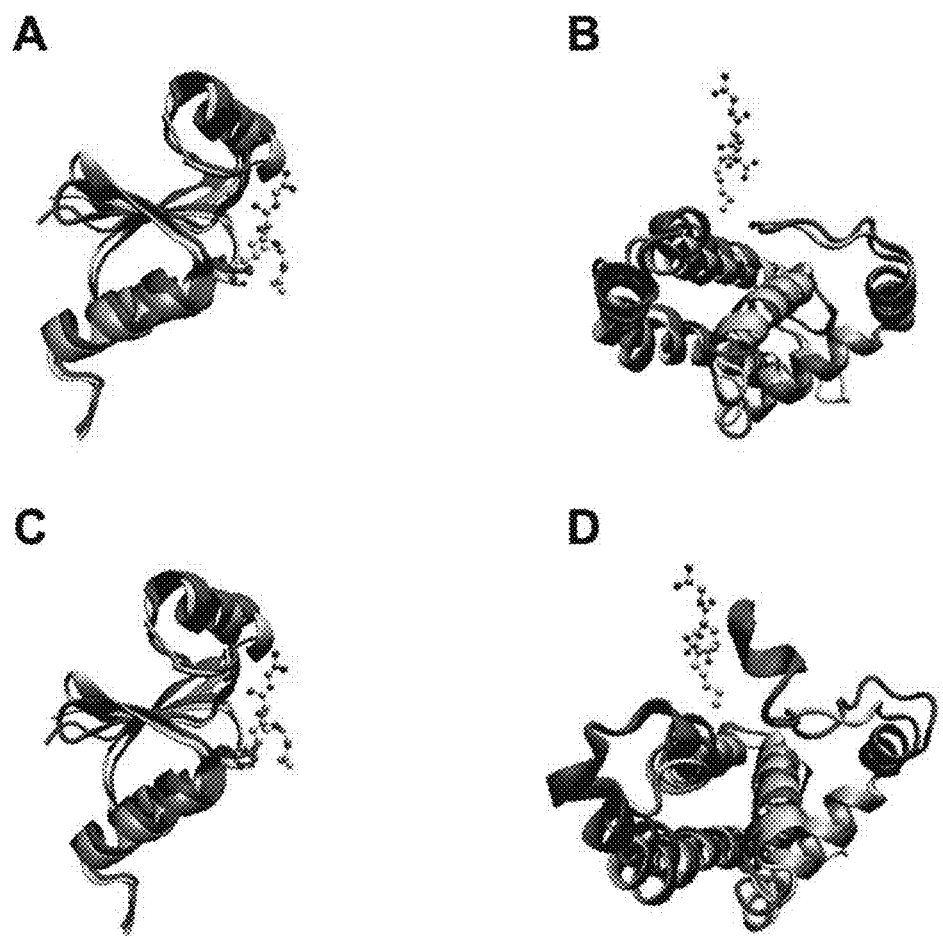
FIG. 5A-D

FIG. 6A-B

```
SEQ ID NO.:86  1 - ATGATGGACAACATAGTGCTGTATTATTTTGACGCAAGgtaaaaaaaaattaataaataa - 60
SEQ ID NO.:87  1 -  M  M  D  N  I  V  L  Y  Y  F  D  A  R  -  -  -  -  -  -  -  - 13

61 - aataattaatctgaaaagttagaaaataatatatgggtttgtgattgtcaatttctttgc - 120
                   -  -  -  -  -  -  -  -  -  -  -  -  -  -  -  -  -  -  -  -

121 - catatttataaagacactttgtaaatacatggatatacatacattgtgtgttatgtaatt - 180
                   -  -  -  -  -  -  -  -  -  -  -  -  -  -  -  -  -  -  -  -

181 - ttatttccgcatggatatatatatatatatatatatttttttttttaagAGGTAAAGCTGA - 240
              14 -  -  -  -  -  -  -  -  -  -  -  -  -  -  -  -  G  K  A  E - 17

241 - ACTGATCAGACTTATTTTTGCATATTTACAAGTTAAATATACAGATATAAGATTTGGAGT - 300
              18 -  L  I  R  L  I  F  A  Y  L  Q  V  K  Y  T  D  I  R  F  G  V - 37

301 - AAATGGTGATGCATTTGCAGAATTTAACAATTTTAAAAAGAAAAGAAATTCCTTTTAA - 360
              38 -  N  G  D  A  F  A  E  F  N  N  F  K  K  E  K  E  I  P  F  N - 57

361 - TCAAGTTCCTATATTGGAAATAGGAGGTTTAATATTAGCTCAAAGCCAATCTATAGTTCG - 420
              58 -  Q  V  P  I  L  E  I  G  G  L  I  L  A  Q  S  Q  S  I  V  R - 77

421 - ATATTTATCAAAAAAATATAATATTAGTGGAAATGGCGAATTAAATGAATTTTATGCTGA - 480
              78 -  Y  L  S  K  K  Y  N  I  S  G  N  G  E  L  N  E  F  Y  A  D - 97

481 - TATGATATTTTGTGGTGTACAAGATATTCATTATAAATTTAATAATACAAATTTATTTAA - 540
              98 -  M  I  F  C  G  V  Q  D  I  H  Y  K  F  N  N  T  N  L  F  K - 117

541 - ACAAAATGAAACTACTTTTTTAAATGAAGAATTACCTAAATGGTCAGGTTATTTTGAAAA - 600
             118 -  Q  N  E  T  T  F  L  N  E  E  L  P  K  W  S  G  Y  F  E  K - 137

601 - ACTTTTACAAAAAAATAATACTAATTATTTTGTAGGGGATACTATAACATATGCAGATTT - 660
             138 -  L  L  Q  K  N  N  T  N  Y  F  V  G  D  T  I  T  Y  A  D  L - 157

661 - AGCAGTTTTTAATTTATATTATGATATTGAATCAAAATATCCAAATTGTTTAAAAAAATT - 720
             158 -  A  V  F  N  L  Y  Y  D  I  E  S  K  Y  P  N  C  L  K  K  F - 177

721 - TCCATTATTAAAAGCCCATACTGAACTTATAAGTAATATTCCAAATATAAAACATTATAT - 780
             178 -  P  L  L  K  A  H  T  E  L  I  S  N  I  P  N  I  K  H  Y  I - 197

781 - TGCTAATAGAAAAGAAAGCGTCTATTAA - 808
             198 -  A  N  R  K  E  S  V  Y  -  - 205
```

FIG. 7

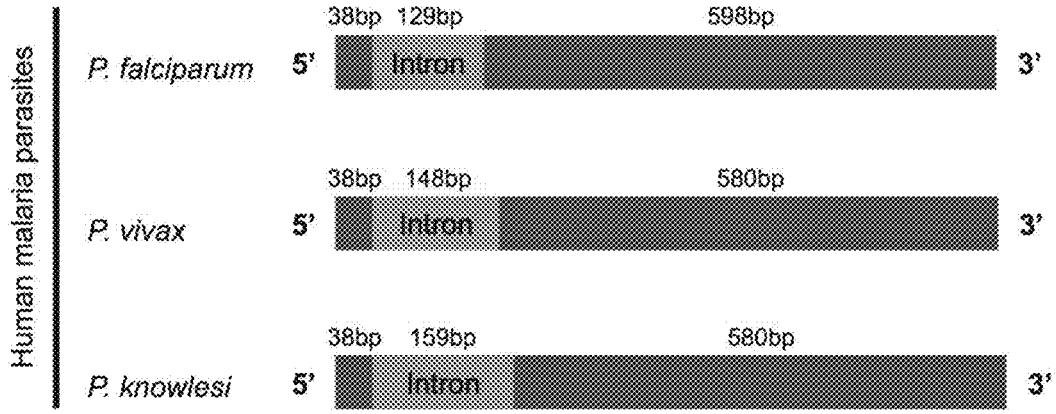
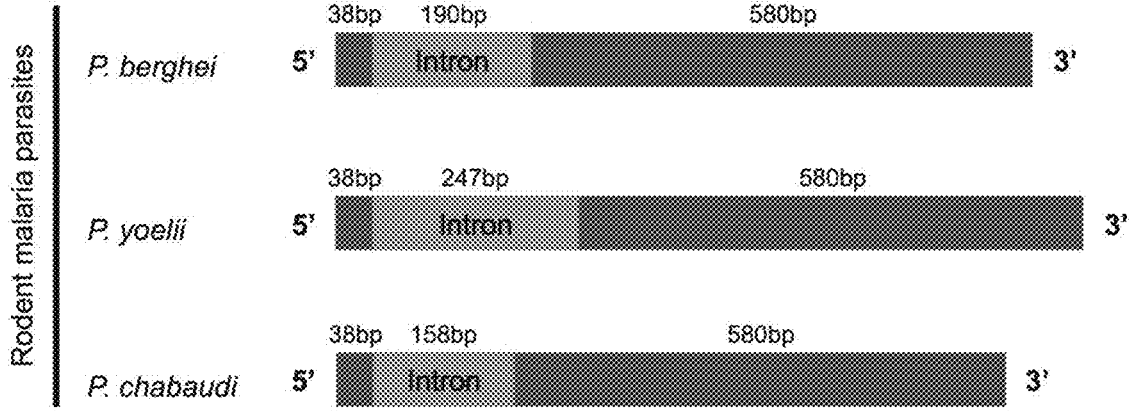
FIG. 8A-B

FIG. 10

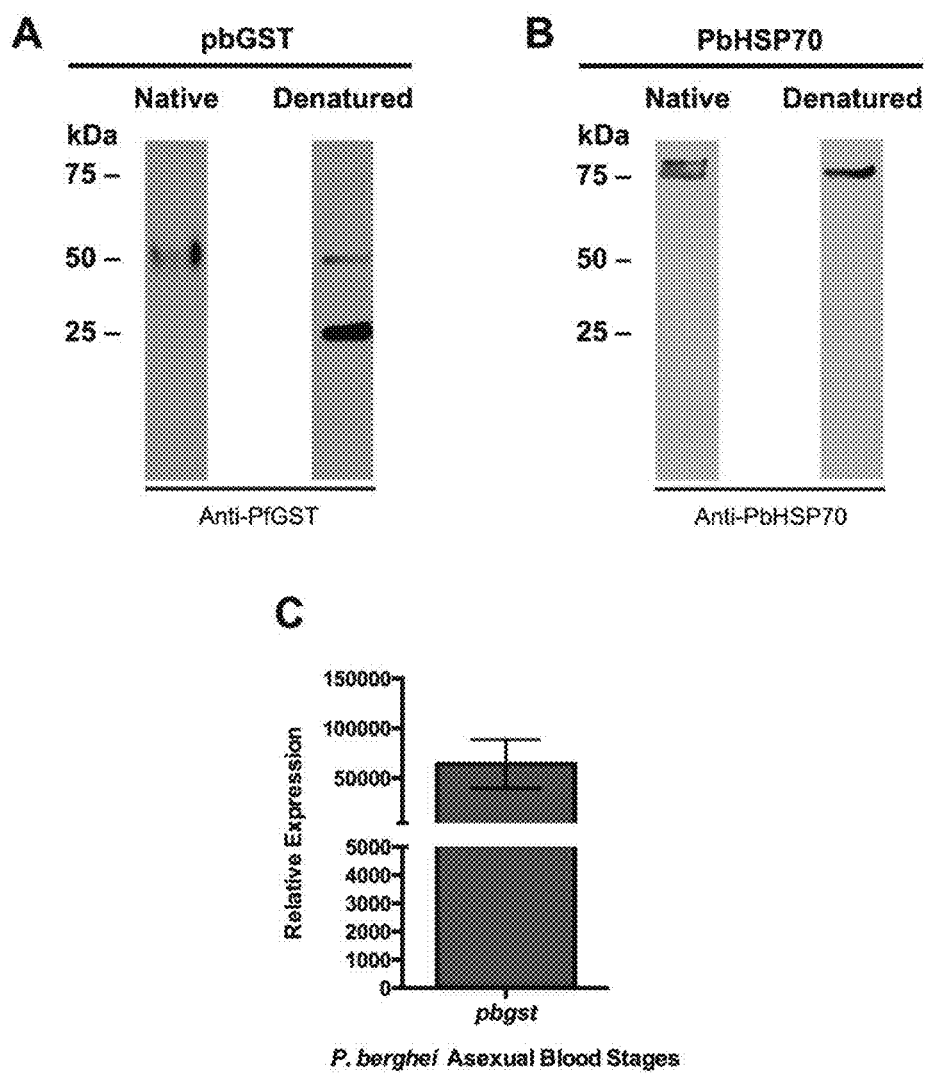
FIG. 11A-C

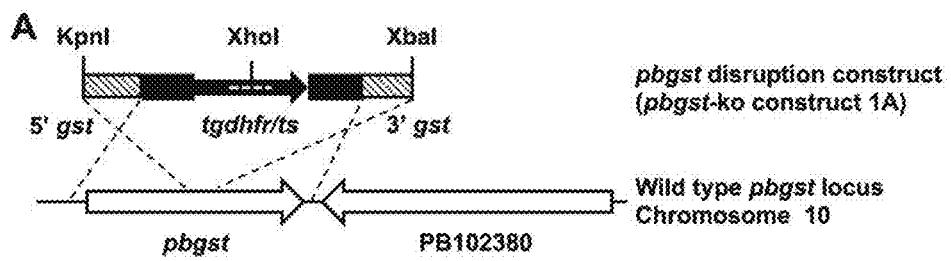
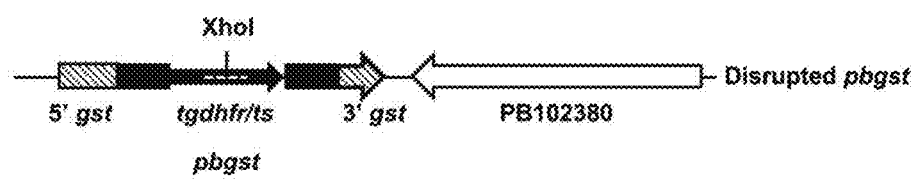
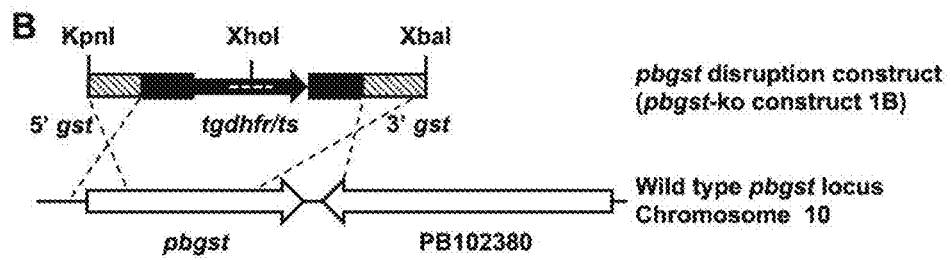
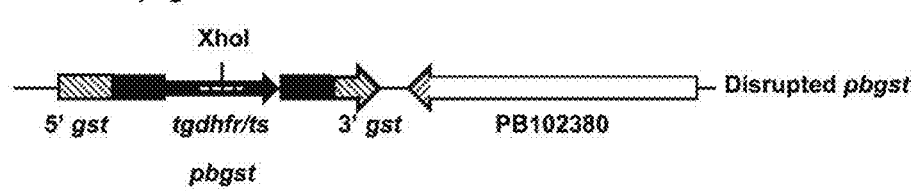
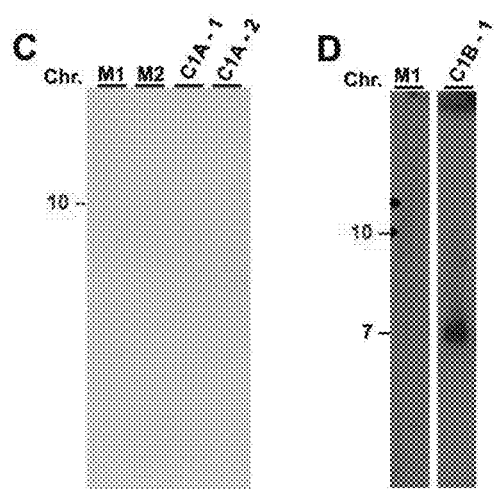
FIG. 12A-E

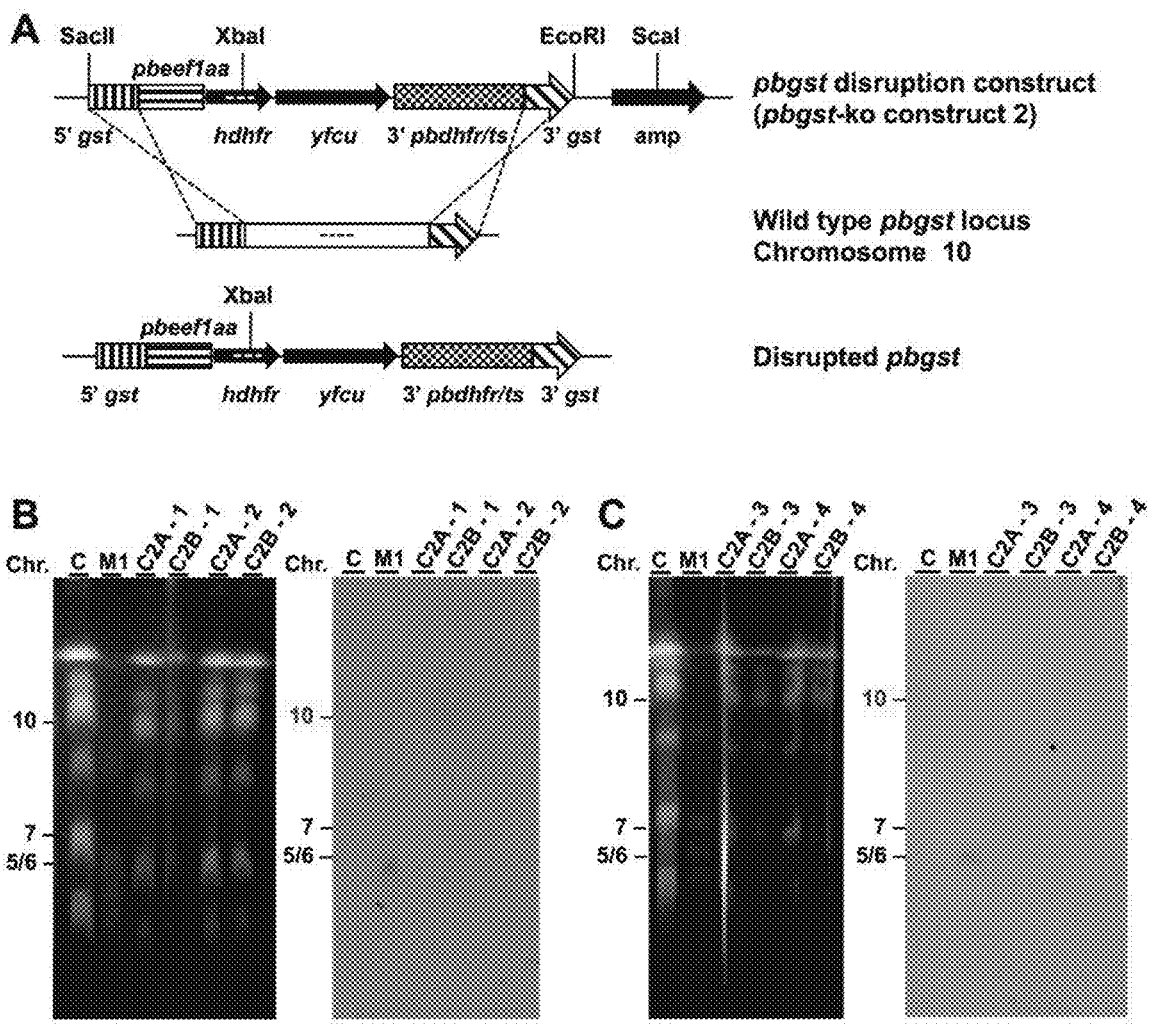
FIG. 13A-D

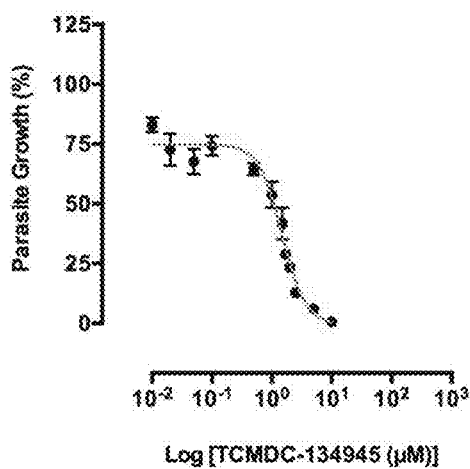
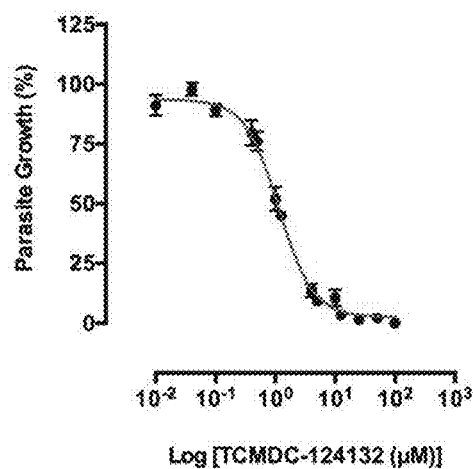
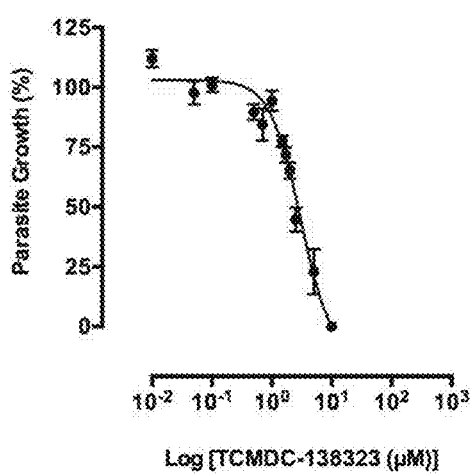
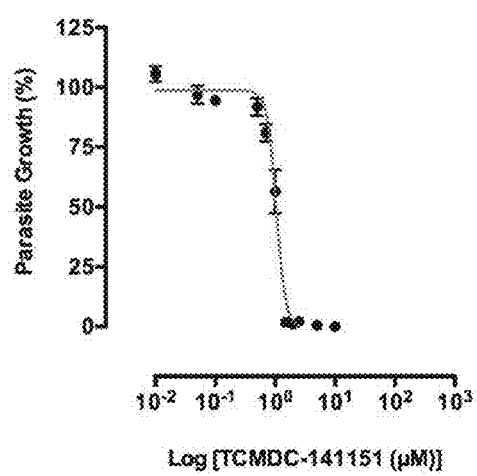
| Legend | Compound | EC$_{50}$ (µM) | 95% CI |
|---|---|---|---|
| A | TCMDC-134945 | 1.48 | 1.25 to 1.76 |
| B | TCMDC-124132 | 1.15 | 0.95 to 1.39 |
| C | TCMDC-138323 | 3.03 | 2.14 to 4.31 |
| D | TCMDC-141151 TCMDC-141221 | 1.04 | 0.97 to 1.12 |
FIG. 23A-E

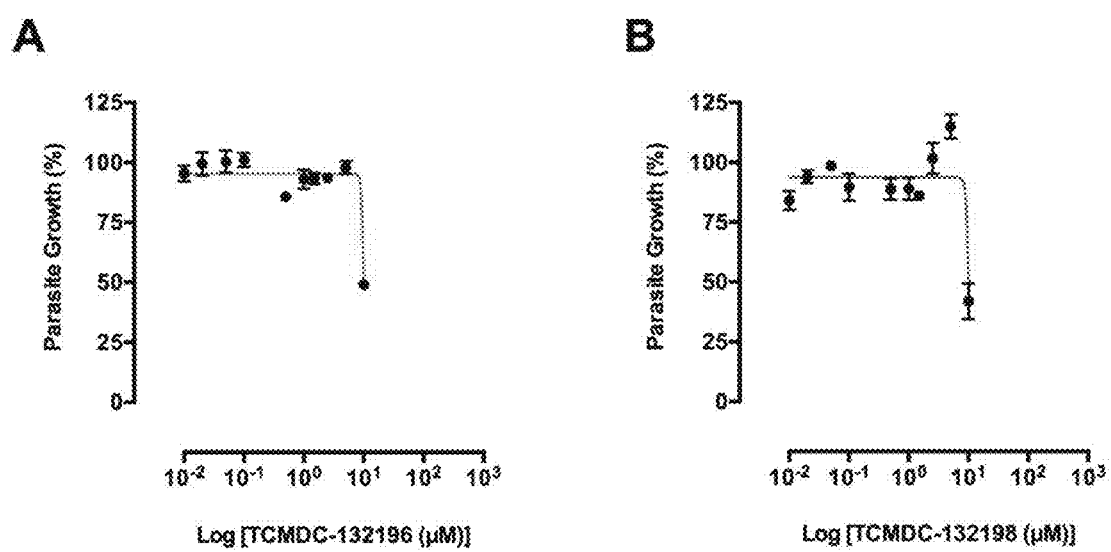
FIG. 24A-B

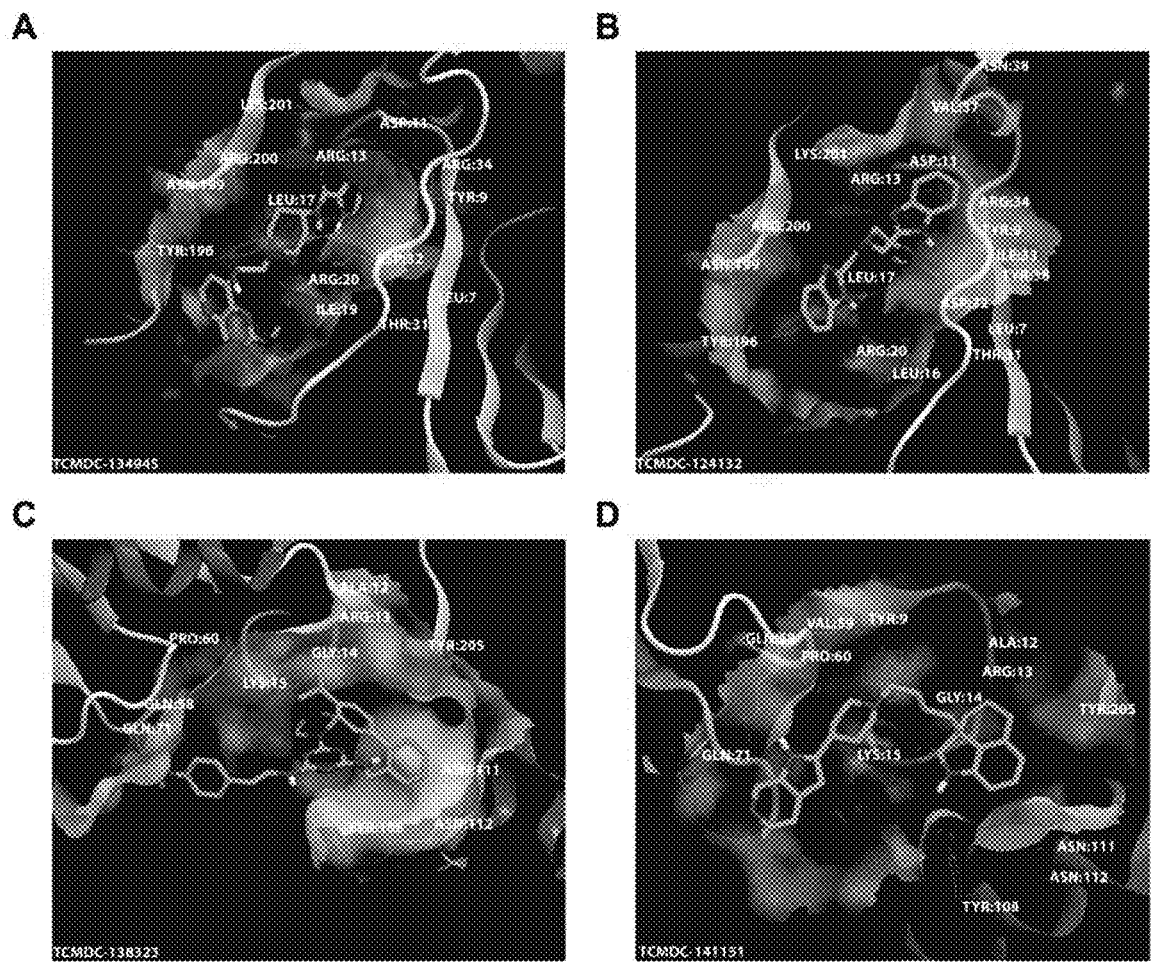
FIG. 25A-D

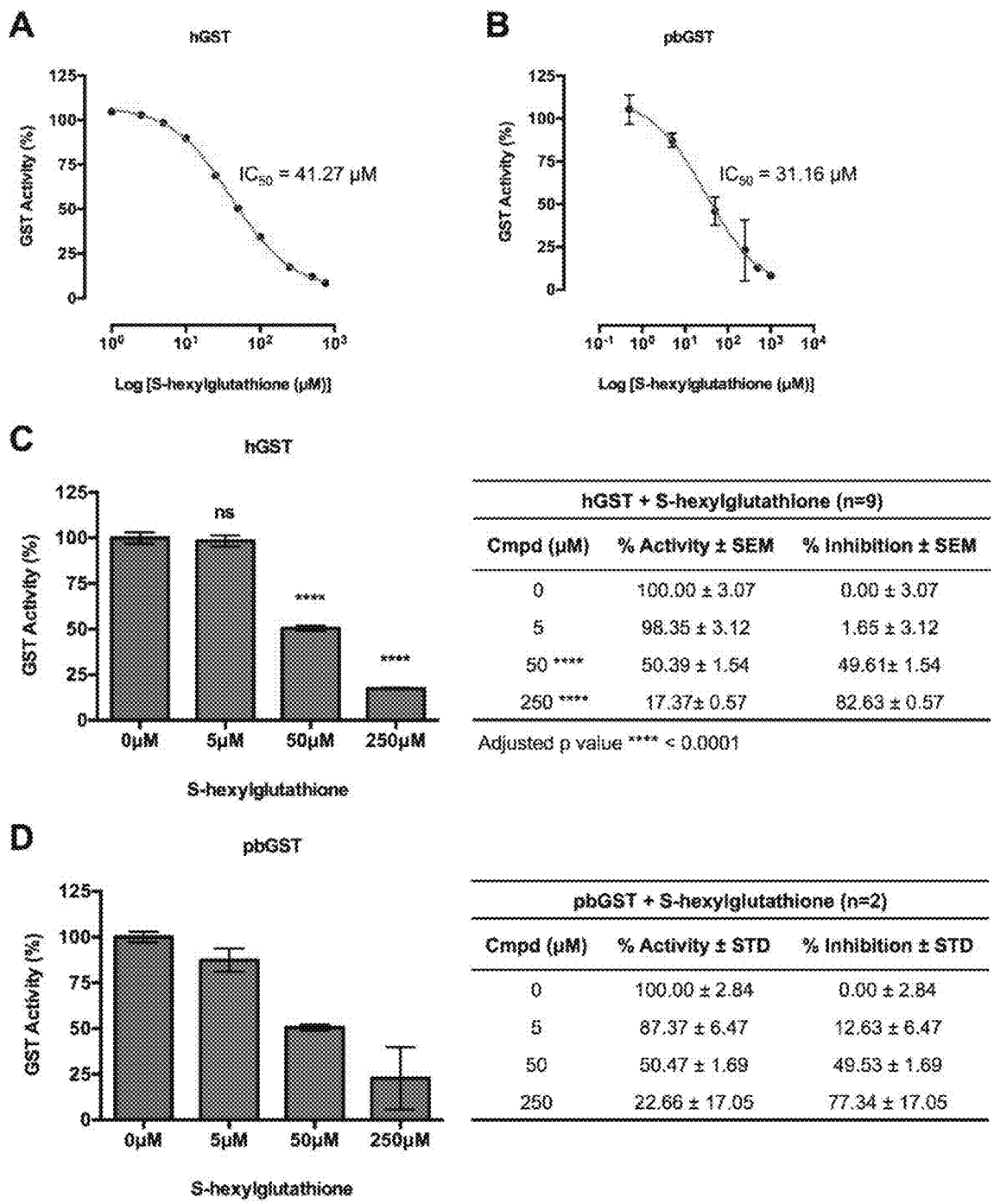
FIG. 26A-D

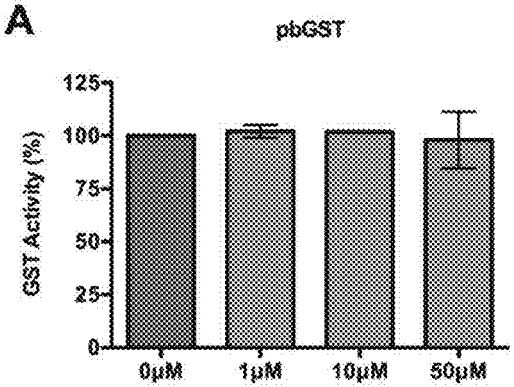
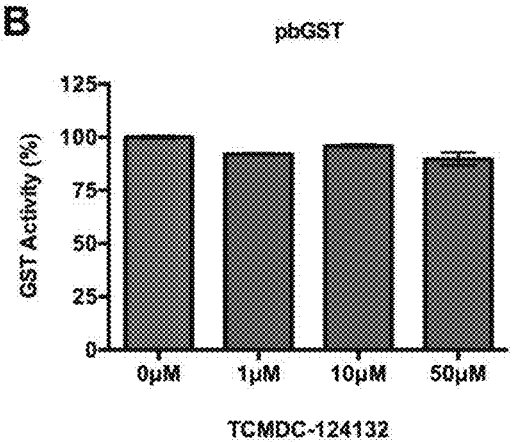
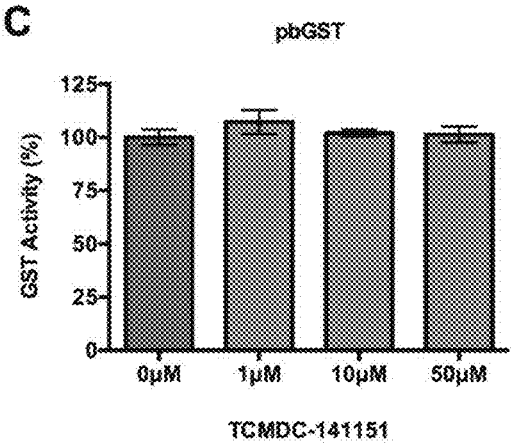
FIG. 27A-C

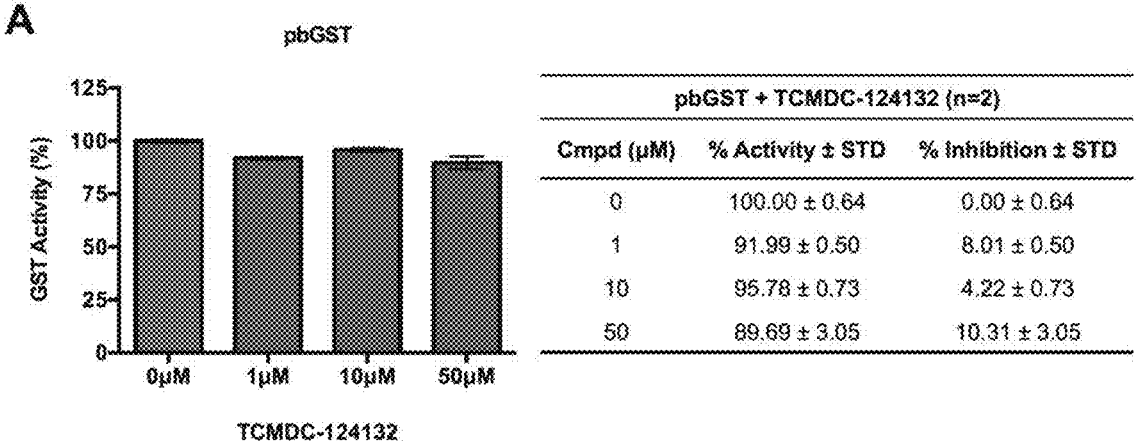
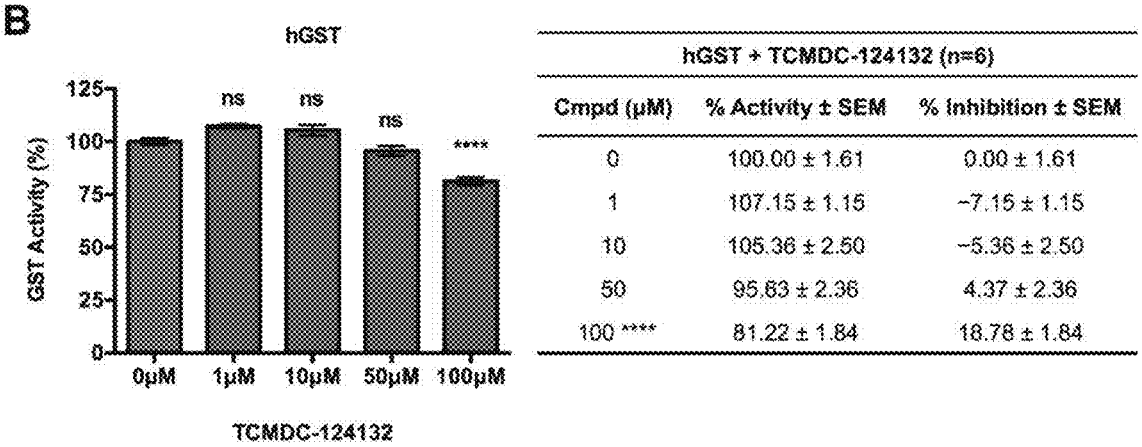
FIG. 28A-B

SEQUENCE LISTING

<160> NUMBER OF SEQ ID NOS: 90

<210> SEQ ID NO 1
<211> LENGTH: 211
<212> TYPE: PRT
<213> ORGANISM: Plasmodium falciparum

<400> SEQUENCE: 1

```
Met Gly Asp Asn Ile Val Leu Tyr Tyr Phe Asp Ala Arg Gly Lys Ala
1               5                   10                  15
Glu Leu Ile Arg Leu Ile Phe Ala Tyr Leu Gly Ile Glu Tyr Thr Asp
            20                  25                  30
Lys Arg Phe Gly Val Asn Gly Asp Ala Phe Val Glu Phe Lys Asn Phe
        35                  40                  45
Lys Lys Glu Lys Asp Thr Pro Phe Glu Gln Val Pro Ile Leu Gln Ile
    50                  55                  60
Gly Asp Leu Ile Leu Ala Gln Ser Gln Ala Ile Val Arg Tyr Leu Ser
65                  70                  75                  80
Lys Lys Tyr Asn Ile Cys Gly Glu Ser Glu Leu Asn Glu Phe Tyr Ala
                85                  90                  95
Asp Met Ile Phe Cys Gly Val Gln Asp Ile His Tyr Lys Phe Asn Asn
            100                 105                 110
Thr Asn Leu Phe Lys Gln Asn Glu Thr Thr Phe Leu Asn Glu Asp Leu
        115                 120                 125
Pro Lys Trp Ser Gly Tyr Phe Glu Lys Leu Leu Lys Lys Asn His Thr
    130                 135                 140
Asn Asn Asn Asp Lys Tyr Tyr Phe Val Gly Asn Asn Leu Thr Tyr
145                 150                 155                 160
Ala Asp Leu Ala Val Phe Asn Leu Tyr Asp Asp Ile Glu Thr Lys Tyr
                165                 170                 175
Pro Ser Ser Leu Lys Asn Phe Pro Leu Leu Lys Ala His Asn Glu Phe
            180                 185                 190
Ile Ser Asn Leu Pro Asn Ile Lys Asn Tyr Ile Thr Asn Arg Lys Glu
        195                 200                 205
Ser Val Tyr
    210
```

<210> SEQ ID NO 2
<211> LENGTH: 205
<212> TYPE: PRT
<213> ORGANISM: Plasmodium vivax

<400> SEQUENCE: 2

```
Met Ala Glu Glu Ile Val Leu Tyr Tyr Phe Asp Ala Arg Gly Lys Ala
1               5                   10                  15
Glu Leu Ile Arg Leu Ile Phe Ala Tyr Leu Gly Ile Gln Tyr Thr Asp
            20                  25                  30
Lys Arg Phe Gly Glu Asn Gly Asp Ala Phe Ile Glu Phe Lys Asn Phe
        35                  40                  45
Lys Lys Glu Lys Glu Thr Pro Phe Asn Gln Val Pro Ile Leu Glu Met
    50                  55                  60
Asp Asn Ile Ile Phe Ala Gln Ser Gln Ala Ile Val Arg Tyr Leu Ser
65                  70                  75                  80
Lys Lys Tyr Lys Ile Ser Gly Asn Ser Glu Leu Asn Glu Phe Tyr Ala
                85                  90                  95
Asp Met Ile Phe Cys Gly Val Gln Asp Ile His Tyr Lys Phe Asn Asn
```

```
                100                 105                 110
Thr Asn Leu Phe Lys Gln Asn Glu Thr Thr Phe Leu Asn Glu Glu Leu
            115                 120                 125
Pro Lys Trp Ser Gly Tyr Phe Glu Asn Ile Leu Lys Lys Asn Asn Cys
            130                 135                 140
Asn Tyr Phe Val Gly Asp Asp Leu Thr Tyr Ala Asp Leu Ala Val Phe
145                 150                 155                 160
Asn Leu Tyr Asp Asp Ile Glu Thr Lys Tyr Pro Asn Ser Leu Lys Asn
                165                 170                 175
Phe Pro Leu Leu Lys Ala His Asn Glu Phe Ile Ser Asn Leu Pro Asn
            180                 185                 190
Ile Lys Asn Tyr Ile Ser Asn Arg Lys Glu Ser Val Tyr
            195                 200                 205

<210> SEQ ID NO 3
<211> LENGTH: 205
<212> TYPE: PRT
<213> ORGANISM: Plasmodium knowlesi

<400> SEQUENCE: 3

Met Ala Glu Glu Ile Val Leu Tyr Tyr Phe Asp Ala Arg Gly Lys Ala
1               5                   10                  15
Glu Leu Ile Arg Leu Ile Phe Ala Tyr Leu Gly Ile Lys Tyr Thr Asp
            20                  25                  30
Lys Arg Phe Gly Glu Lys Gly Asp Ala Phe Ile Glu Phe Lys Asn Phe
        35                  40                  45
Lys Lys Glu Lys Lys Thr Pro Phe Glu Gln Val Pro Ile Leu Glu Met
    50                  55                  60
Asp Asn Ile Ile Phe Ala Gln Ser Gln Ala Ile Val Arg Tyr Leu Ser
65                  70                  75                  80
Lys Lys Tyr Lys Ile Gly Gly Asp Thr Asp Leu Asp Glu Phe Tyr Ala
                85                  90                  95
Asp Met Ile Phe Cys Gly Val Gln Asp Ile His Tyr Lys Phe Asn Asn
            100                 105                 110
Thr Asn Leu Phe Lys Gln Asn Glu Thr Thr Phe Leu Asn Glu Glu Leu
            115                 120                 125
Pro Lys Trp Ser Gly Tyr Phe Glu Asn Ile Leu Lys Lys Asn Lys Cys
            130                 135                 140
His Tyr Phe Val Gly Asp Asn Leu Thr Tyr Ala Asp Leu Ala Val Phe
145                 150                 155                 160
Asn Leu Tyr Asp Asp Ile Glu Thr Lys Tyr Pro Asn Ser Leu Lys Asn
                165                 170                 175
Phe Pro Leu Leu Lys Ala His Asn Glu Phe Ile Ser Asn Leu Pro Asn
            180                 185                 190
Ile Lys Asn Tyr Ile Ser Asn Arg Lys Glu Ser Val Tyr
            195                 200                 205

<210> SEQ ID NO 4
<211> LENGTH: 209
<212> TYPE: PRT
<213> ORGANISM: Plasmodium yoelii

<400> SEQUENCE: 4

Met Thr Tyr Leu Tyr Asn Phe Phe Phe Phe Phe Phe Phe Phe Phe Ser
1               5                   10                  15
Arg Gly Lys Ala Glu Leu Ile Arg Leu Ile Phe Ala Tyr Leu Gln Val
```

```
                     20                  25                  30
Lys Tyr Thr Asp Ile Arg Phe Gly Val Asn Gly Asp Ala Phe Ala Glu
                 35                  40                  45
Phe Asn Asn Phe Lys Lys Glu Lys Glu Ile Pro Phe Asn Gln Val Pro
             50                  55                  60
Ile Leu Glu Ile Gly Gly Leu Ile Leu Ala Gln Ser Gln Ala Ile Val
 65                  70                  75                  80
Arg Tyr Leu Ser Lys Lys Tyr Asn Ile Ser Gly Asn Gly Glu Leu Asn
                 85                  90                  95
Glu Phe Tyr Ala Asp Met Ile Phe Cys Gly Val Gln Asp Ile His Tyr
            100                 105                 110
Lys Phe Asn Asn Thr Asn Leu Phe Lys Gln Asn Glu Thr Thr Phe Leu
            115                 120                 125
Asn Glu Glu Leu Pro Lys Trp Ser Gly Tyr Phe Glu Lys Leu Leu Gln
            130                 135                 140
Lys Asn Asn Thr Asn Tyr Phe Val Gly Asp Thr Ile Thr Tyr Ala Asp
145                 150                 155                 160
Leu Ala Val Phe Asn Leu Tyr Asp Asp Ile Glu Ser Lys Tyr Pro Asn
                165                 170                 175
Cys Leu Lys Asn Phe Pro Leu Leu Lys Ala His Ile Glu Leu Ile Ser
            180                 185                 190
Asn Ile Pro Asn Ile Lys His Tyr Ile Ala Asn Arg Lys Glu Ser Val
            195                 200                 205
Tyr

<210> SEQ ID NO 5
<211> LENGTH: 222
<212> TYPE: PRT
<213> ORGANISM: Homo sapiens

<400> SEQUENCE: 5

Met Ala Glu Lys Pro Lys Leu His Tyr Phe Asn Ala Arg Gly Arg Met
 1               5                  10                  15
Glu Ser Thr Arg Trp Leu Leu Ala Ala Ala Gly Val Glu Phe Glu Glu
                 20                  25                  30
Lys Phe Ile Lys Ser Ala Glu Asp Leu Asp Lys Leu Arg Asn Asp Gly
                 35                  40                  45
Tyr Leu Met Phe Gln Gln Val Pro Met Val Glu Ile Asp Gly Met Lys
             50                  55                  60
Leu Val Gln Thr Arg Ala Ile Leu Asn Tyr Ile Ala Ser Lys Tyr Asn
 65                  70                  75                  80
Leu Tyr Gly Lys Asp Ile Lys Glu Arg Ala Leu Ile Asp Met Tyr Ile
                 85                  90                  95
Glu Gly Ile Ala Asp Leu Gly Glu Met Ile Leu Leu Pro Val Cys
            100                 105                 110
Pro Pro Glu Glu Lys Asp Ala Lys Leu Ala Leu Ile Lys Glu Lys Ile
            115                 120                 125
Lys Asn Arg Tyr Phe Pro Ala Phe Glu Lys Val Leu Lys Ser His Gly
            130                 135                 140
Gln Asp Tyr Leu Val Gly Asn Lys Leu Ser Arg Ala Asp Ile His Leu
145                 150                 155                 160
Val Glu Leu Leu Tyr Tyr Val Glu Glu Leu Asp Ser Ser Leu Ile Ser
                165                 170                 175
Ser Phe Pro Leu Leu Lys Ala Leu Lys Thr Arg Ile Ser Asn Leu Pro
```

```
              180                 185                 190
Thr Val Lys Lys Phe Leu Gln Pro Gly Ser Arg Lys Pro Pro Met
             195                 200                 205

Asp Glu Lys Ser Leu Glu Glu Ala Arg Lys Ile Phe Arg Phe
 210                 215                 220
```

<210> SEQ ID NO 6
<211> LENGTH: 222
<212> TYPE: PRT
<213> ORGANISM: Rattus norvegicus

<400> SEQUENCE: 6

```
Met Ser Gly Lys Pro Val Leu His Tyr Phe Asn Ala Arg Gly Arg Met
 1               5                  10                  15

Glu Cys Ile Arg Trp Leu Leu Ala Ala Ala Gly Val Glu Phe Asp Glu
                20                  25                  30

Lys Phe Ile Gln Ser Pro Glu Asp Leu Glu Lys Leu Lys Lys Asp Gly
                35                  40                  45

Asn Leu Met Phe Asp Gln Val Pro Met Val Glu Ile Asp Gly Met Lys
 50                  55                  60

Leu Ala Gln Thr Arg Ala Ile Leu Asn Tyr Ile Ala Thr Lys Tyr Asp
 65                  70                  75                  80

Leu Tyr Gly Lys Asp Met Lys Glu Arg Ala Leu Ile Asp Met Tyr Thr
                 85                  90                  95

Glu Gly Ile Leu Asp Leu Thr Glu Met Ile Met Gln Leu Val Ile Cys
                100                 105                 110

Pro Pro Asp Gln Lys Glu Ala Lys Thr Ala Leu Ala Lys Asp Arg Thr
                115                 120                 125

Lys Asn Arg Tyr Leu Pro Ala Phe Glu Lys Val Leu Lys Ser His Gly
 130                 135                 140

Gln Asp Tyr Leu Val Gly Asn Arg Leu Thr Arg Val Asp Ile His Leu
 145                 150                 155                 160

Leu Glu Leu Leu Leu Tyr Val Glu Glu Phe Asp Ala Ser Leu Leu Thr
                 165                 170                 175

Ser Phe Pro Leu Leu Lys Ala Phe Lys Ser Arg Ile Ser Ser Leu Pro
                180                 185                 190

Asn Val Lys Lys Phe Leu Gln Pro Gly Ser Gln Arg Lys Leu Pro Val
                195                 200                 205

Asp Ala Lys Gln Ile Glu Glu Ala Arg Lys Ile Phe Lys Phe
 210                 215                 220
```

<210> SEQ ID NO 7
<211> LENGTH: 223
<212> TYPE: PRT
<213> ORGANISM: Mus musculus

<400> SEQUENCE: 7

```
Met Ala Gly Lys Pro Val Leu His Tyr Phe Asn Ala Arg Gly Arg Met
 1               5                  10                  15

Glu Cys Ile Arg Trp Leu Leu Ala Ala Ala Gly Val Glu Phe Glu Glu
                20                  25                  30

Lys Phe Ile Gln Ser Pro Glu Asp Leu Glu Lys Leu Lys Lys Asp Gly
                35                  40                  45

Asn Leu Met Phe Asp Gln Val Pro Met Val Glu Ile Asp Gly Met Lys
 50                  55                  60

Leu Ala Gln Thr Arg Ala Ile Leu Asn Tyr Ile Ala Thr Lys Tyr Asp
```

```
                65                  70                  75                  80
Leu Tyr Gly Lys Asp Met Lys Glu Arg Ala Leu Ile Asp Met Tyr Ser
                    85                  90                  95

Glu Gly Ile Leu Asp Leu Thr Glu Met Ile Gly Gln Leu Val Leu Cys
                100                 105                 110

Pro Pro Asp Gln Arg Glu Ala Lys Thr Ala Leu Ala Lys Asp Arg Thr
                115                 120                 125

Lys Asn Arg Tyr Leu Pro Ala Phe Glu Lys Val Leu Lys Ser His Gly
130                 135                 140

Gln Asp Tyr Leu Val Gly Asn Arg Leu Thr Arg Val Asp Ile His Leu
145                 150                 155                 160

Leu Glu Val Leu Leu Tyr Val Glu Glu Phe Asp Ala Ser Leu Leu Thr
                165                 170                 175

Pro Phe Pro Leu Leu Lys Ala Phe Lys Ser Arg Ile Ser Ser Leu Pro
                180                 185                 190

Asn Val Lys Lys Phe Leu Gln Pro Gly Ser Gln Arg Lys Pro Pro Met
                195                 200                 205

Asp Ala Lys Gln Ile Gln Glu Ala Arg Lys Ala Phe Lys Ile Gln
210                 215                 220

<210> SEQ ID NO 8
<211> LENGTH: 222
<212> TYPE: PRT
<213> ORGANISM: Sus scrofa

<400> SEQUENCE: 8

Met Ala Gly Lys Pro Ile Leu His Tyr Phe Asn Gly Arg Gly Arg Met
1               5                   10                  15

Glu Cys Ile Arg Trp Leu Leu Ala Ala Ala Gly Val Glu Phe Glu Glu
                20                  25                  30

Lys Phe Ile Lys Thr Pro Glu Asp Leu Asp Lys Leu Thr Asn Asp Gly
                35                  40                  45

Ser Leu Leu Phe Gln Gln Val Pro Met Val Glu Ile Asp Gly Met Lys
50                  55                  60

Leu Val Gln Thr Arg Ala Ile Leu Asn Tyr Ile Ala Thr Lys Tyr Asn
65                  70                  75                  80

Leu Tyr Gly Lys Asp Ala Lys Glu Arg Ala Leu Ile Asp Met Tyr Thr
                    85                  90                  95

Glu Gly Val Ala Asp Leu Gly Glu Met Ile Leu Leu Leu Pro Leu Cys
                100                 105                 110

Pro Pro Asn Glu Lys Asp Ala Lys Val Ala Ser Ile Lys Glu Lys Ser
                115                 120                 125

Thr Asn Arg Tyr Leu Pro Ala Phe Glu Lys Val Leu Lys Ser His Gly
130                 135                 140

Gln Asp Tyr Leu Val Gly Asn Lys Leu Ser Arg Ala Asp Ile Gln Leu
145                 150                 155                 160

Val Glu Leu Leu Tyr Tyr Val Glu Glu Leu Asp Pro Ser Leu Leu Ala
                165                 170                 175

Asn Phe Pro Leu Leu Lys Ala Leu Lys Thr Arg Val Ser Asn Leu Pro
                180                 185                 190

Thr Val Lys Lys Phe Leu Gln Pro Gly Ser Gln Arg Lys Pro Pro Met
                195                 200                 205

Asp Ala Lys Lys Ile Arg Arg Ser Gln Glu Tyr Phe Pro Asp
210                 215                 220
```

```
<210> SEQ ID NO 9
<211> LENGTH: 218
<212> TYPE: PRT
<213> ORGANISM: Cavia porcellus

<400> SEQUENCE: 9

Ser Gly Lys Pro Val Leu His Tyr Phe Asn Val Gln Gly Arg Met Glu
1               5                   10                  15

Ser Ile Arg Trp Leu Leu Ala Ala Gly Val Glu Phe Glu Glu Lys
            20                  25                  30

Leu Ile Met Cys Gln Glu Asp Leu Asp Lys Leu Lys Asn Asp Gly Leu
            35                  40                  45

Leu Met Phe Gln Gln Val Pro Met Val Glu Met Asp Gly Met Lys Met
        50                  55                  60

Val Gln Ser Arg Ala Ile Leu Asn Tyr Ile Ala Thr Lys Tyr Asn Leu
65                  70                  75                  80

Tyr Gly Lys Asp Thr Lys Glu Arg Leu Leu Ile Asp Met Tyr Thr Glu
                85                  90                  95

Gly Met Thr Asp Leu Tyr Glu Leu Phe Phe Lys Val Ile Leu Ala Pro
            100                 105                 110

Pro Glu Glu Lys Asp Ala Ala Lys Ser Leu Ile Lys Asp Arg Ala Lys
        115                 120                 125

Asn Arg Phe Leu Pro Ala Phe Glu Lys Val Leu Lys Ser His Gly Gln
130                 135                 140

Gly Tyr Leu Val Gly Asn Lys Leu Ser Lys Ala Asp Ile Leu Leu Thr
145                 150                 155                 160

Glu Leu Leu Tyr Met Val Glu Phe Asp Ala Ser Leu Leu Ala Asn
                165                 170                 175

Phe Thr Leu Leu Gln Ala Leu Lys Thr Arg Val Ser Asn Leu Pro Asn
            180                 185                 190

Val Lys Lys Phe Leu Gln Pro Gly Ser Gln Arg Lys Pro Phe Pro Thr
        195                 200                 205

Gln Glu Met Phe Glu Glu Met Arg Lys Phe
    210                 215

<210> SEQ ID NO 10
<211> LENGTH: 235
<212> TYPE: PRT
<213> ORGANISM: Oncocherca volvulus

<400> SEQUENCE: 10

Phe Ile Thr Met Asn Phe Val Val Glu Ala Ala Ser Ser Asn Ala Asn
1               5                   10                  15

Gln Ala Ile Thr Ser Glu Asn Ser Ile Lys Pro Lys Gly Lys Leu Gln
            20                  25                  30

Pro Gln Met Glu Lys Tyr Thr Leu Thr Tyr Phe Asn Gly Arg Gly Arg
            35                  40                  45

Ala Glu Val Ile Arg Leu Leu Phe Ala Leu Ala Asn Val Ser Tyr Glu
        50                  55                  60

Asp Asn Arg Ile Thr Arg Asp Glu Trp Lys Tyr Leu Lys Pro Arg Thr
65                  70                  75                  80

Pro Phe Gly His Val Pro Met Leu Asn Val Ser Gly Asn Val Leu Gly
                85                  90                  95

Glu Ser His Ala Ile Glu Leu Leu Leu Gly Gly Arg Phe Gly Leu Leu
            100                 105                 110
```

```
Gly Thr Asn Asp Trp Glu Glu Ala Lys Ile Met Ala Val Leu Asn
            115                 120                 125
Ile Asp Glu Leu Phe Gln Lys Leu Ile Pro Trp Thr His Glu Lys Asn
130                 135                 140
Thr Thr Lys Lys Ala Glu Leu Phe Arg Asn Leu Ser Glu Ser Asp Val
145                 150                 155                 160
Met Pro Phe Leu Gly Arg Tyr Glu Lys Phe Leu Lys Glu Ser Thr Thr
                165                 170                 175
Gly His Ile Val Gly Asn Lys Val Ser Val Ala Asp Leu Thr Val Phe
                180                 185                 190
Asn Met Leu Met Thr Leu Asp Asp Glu Val Lys Leu Glu Glu Tyr Pro
            195                 200                 205
Gln Leu Ala Ser Phe Val Asn Lys Ile Gly Gln Met Pro Gly Ile Lys
            210                 215                 220
Glu Trp Ile Lys Lys Arg Pro Lys Thr Tyr Phe
225                 230                 235

<210> SEQ ID NO 11
<211> LENGTH: 241
<212> TYPE: PRT
<213> ORGANISM: Musca domestica

<400> SEQUENCE: 11

Met Ala Asp Glu Ala Pro Ala Ala Pro Pro Glu Gly Glu Ala Pro
1               5                   10                  15
Ala Ala Pro Ala Glu Gly Glu Ala Pro Pro Ala Glu Gly Glu Ala
                20                  25                  30
Pro Pro Ala Glu Pro Val Lys Asn Thr Tyr Thr Leu Phe Tyr Phe Asn
                35                  40                  45
Val Lys Ala Leu Ala Glu Pro Leu Arg Tyr Leu Phe Ala Tyr Gly Gly
            50                  55                  60
Ile Glu Tyr Glu Asp Val Arg Val Thr Arg Asp Glu Trp Pro Ala Leu
65                  70                  75                  80
Lys Pro Thr Met Pro Met Gly Gln Met Pro Val Leu Glu Val Asn Gly
                85                  90                  95
Lys Arg Val His Gln Ser Ile Ser Met Ala Arg Phe Leu Ala Lys Thr
                100                 105                 110
Val Gly Leu Cys Gly Ala Thr Pro Trp Glu Asp Leu Gln Val Asp Ile
            115                 120                 125
Val Val Asp Thr Ile Asn Asp Phe Arg Leu Lys Ile Ala Val Val Ser
130                 135                 140
Tyr Glu Pro Glu Asp Glu Ile Lys Glu Lys Lys Leu Val Thr Leu Asn
145                 150                 155                 160
Asn Glu Val Ile Pro Phe Tyr Leu Glu Lys Leu Glu Gln Thr Val Lys
                165                 170                 175
Asp Asn Asp Gly His Leu Ala Leu Asn Lys Leu Thr Trp Ala Asp Val
            180                 185                 190
Tyr Phe Ala Gly Ile Leu Asp Tyr Met Asn Tyr Met Val Lys Arg Asp
            195                 200                 205
Ile Leu Glu Gln Tyr Pro Ala Leu Arg Gly Val Val Asp Ser Val Asn
            210                 215                 220
Ala Leu Glu Pro Ile Lys Ala Trp Ile Glu Lys Arg Pro Gln Thr Glu
225                 230                 235                 240
Val
```

<210> SEQ ID NO 12
<211> LENGTH: 203
<212> TYPE: PRT
<213> ORGANISM: Ommastrephes sloanei

<400> SEQUENCE: 12

Met Pro Lys Tyr Thr Leu His Tyr Phe Pro Leu Met Gly Arg Ala Glu
1               5                   10                  15

Leu Cys Arg Phe Val Leu Ala Ala His Gly Glu Glu Phe Thr Asp Arg
            20                  25                  30

Val Val Glu Met Ala Asp Trp Pro Asn Leu Lys Ala Thr Met Tyr Ser
        35                  40                  45

Asn Ala Met Pro Val Leu Asp Ile Asp Gly Thr Lys Met Ser Gln Ser
    50                  55                  60

Met Cys Ile Ala Arg His Leu Ala Arg Glu Phe Gly Leu Asp Gly Lys
65                  70                  75                  80

Thr Ser Leu Glu Lys Tyr Arg Val Asp Glu Ile Thr Glu Thr Leu Gln
                85                  90                  95

Asp Ile Phe Asn Asp Val Val Lys Ile Lys Phe Ala Pro Glu Ala Ala
            100                 105                 110

Lys Glu Ala Val Gln Gln Asn Tyr Glu Lys Ser Cys Lys Arg Leu Ala
        115                 120                 125

Pro Phe Leu Glu Gly Leu Leu Val Ser Asn Gly Gly Asp Gly Phe
    130                 135                 140

Phe Val Gly Asn Ser Met Thr Leu Ala Asp Leu His Cys Tyr Val Ala
145                 150                 155                 160

Leu Glu Val Pro Leu Lys His Thr Pro Glu Leu Leu Lys Asp Cys Pro
                165                 170                 175

Lys Ile Val Ala Leu Arg Lys Arg Val Ala Glu Cys Pro Lys Ile Ala
            180                 185                 190

Ala Tyr Leu Lys Lys Arg Pro Val Arg Asp Phe
        195                 200

<210> SEQ ID NO 13
<211> LENGTH: 207
<212> TYPE: PRT
<213> ORGANISM: Caenorhabditis elegans

<400> SEQUENCE: 13

Met Pro Asn Tyr Lys Leu Leu Tyr Phe Asp Ala Arg Ala Leu Ala Glu
1               5                   10                  15

Pro Ile Arg Ile Met Phe Ala Met Leu Asn Val Pro Tyr Glu Asp Tyr
            20                  25                  30

Arg Val Ser Val Glu Glu Trp Ser Lys Leu Lys Pro Thr Thr Pro Phe
        35                  40                  45

Gly Gln Leu Pro Ile Leu Gln Val Asp Gly Glu Gln Phe Gly Gln Ser
    50                  55                  60

Met Ser Ile Thr Arg Tyr Leu Ala Arg Lys Phe Gly Leu Ala Gly Lys
65                  70                  75                  80

Thr Ala Glu Glu Glu Ala Tyr Ala Asp Ser Ile Val Asp Gln Tyr Arg
                85                  90                  95

Asp Phe Ile Phe Phe Arg Gln Phe Thr Ser Ser Val Phe Tyr Gly
            100                 105                 110

Ser Asp Ala Asp His Ile Asn Lys Val Arg Phe Glu Val Glu Pro
        115                 120                 125

```
Ala Arg Asp Asp Phe Leu Ala Ile Ile Asn Lys Phe Leu Ala Lys Ser
    130                 135                 140

Lys Ser Gly Phe Leu Val Gly Asp Ser Leu Thr Trp Ala Asp Ile Val
145                 150                 155                 160

Ile Ala Asp Asn Leu Thr Ser Leu Leu Lys Asn Gly Phe Leu Asp Phe
                165                 170                 175

Asn Lys Glu Lys Lys Leu Glu Glu Phe Tyr Asn Lys Ile His Ser Ile
            180                 185                 190

Pro Glu Ile Lys Asn Tyr Val Ala Thr Arg Lys Asp Ser Ile Val
            195                 200                 205
```

<210> SEQ ID NO 14
<211> LENGTH: 207
<212> TYPE: PRT
<213> ORGANISM: Caenorhabditis elegans

<400> SEQUENCE: 14

```
Met Val His Tyr Lys Leu Thr Tyr Phe Asn Ala Arg Gly Leu Ala Glu
1               5                   10                  15

Ile Ser Arg Gln Leu Phe His Met Ala Gly Val Glu Phe Glu Asp Glu
            20                  25                  30

Arg Ile Asn Glu Glu Lys Phe Ser Gln Leu Lys Pro Thr Phe Pro Ser
        35                  40                  45

Gly Gln Val Pro Ile Leu Cys Ile Asp Gly Ala Gln Phe Ser Gln Ser
50                  55                  60

Thr Ala Ile Ala Arg Tyr Leu Ala Arg Lys Phe Gly Phe Val Gly Gln
65                  70                  75                  80

Thr Ala Glu Glu Glu Leu Gln Ala Asp Glu Val Val Asp Thr Phe Lys
                85                  90                  95

Asp Phe Ile Glu Ser Phe Arg Lys Phe Val Ile Ala Val Leu Ser Gly
            100                 105                 110

Glu Ser Glu Glu Ile Leu Lys Asn Ile Arg Glu Glu Val Ile Lys Pro
        115                 120                 125

Ala Val Lys Thr Tyr Thr Ala Tyr Leu Lys Ala Ile Leu Glu Lys Ser
130                 135                 140

Ser Ser Gly Tyr Leu Val Gly Asn Glu Leu Thr Trp Ala Asp Leu Val
145                 150                 155                 160

Ile Ala Asp Asn Leu Thr Thr Leu Ile Asn Ala Glu Leu Leu Asp Ile
                165                 170                 175

Glu Asn Asp Lys Leu Leu Lys Glu Phe Arg Glu Lys Ile Ile Glu Thr
            180                 185                 190

Pro Lys Leu Lys Glu Trp Leu Ala Lys Arg Pro Glu Thr Arg Phe
            195                 200                 205
```

<210> SEQ ID NO 15
<211> LENGTH: 210
<212> TYPE: PRT
<213> ORGANISM: Homo sapiens

<400> SEQUENCE: 15

```
Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45
```

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
            115                 120                 125

Pro Phe Glu Thr Leu Leu Ser Gln Asn Gln Gly Gly Lys Thr Phe Ile
        130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210

<210> SEQ ID NO 16
<211> LENGTH: 210
<212> TYPE: PRT
<213> ORGANISM: mus musculus

<400> SEQUENCE: 16

Met Pro Pro Tyr Thr Ile Val Tyr Phe Pro Val Arg Gly Arg Cys Glu
1               5                   10                  15

Ala Met Arg Met Leu Leu Ala Asp Gln Gly Gln Ser Trp Lys Glu Glu
            20                  25                  30

Val Val Thr Ile Asp Thr Trp Met Gln Gly Leu Leu Lys Pro Thr Cys
        35                  40                  45

Leu Tyr Gly Gln Leu Pro Lys Phe Glu Asp Gly Asp Leu Thr Leu Tyr
    50                  55                  60

Gln Ser Asn Ala Ile Leu Arg His Leu Gly Arg Ser Leu Gly Leu Tyr
65                  70                  75                  80

Gly Lys Asn Gln Arg Glu Ala Ala Gln Met Asp Met Val Asn Asp Gly
                85                  90                  95

Val Glu Asp Leu Arg Gly Lys Tyr Val Thr Leu Ile Tyr Thr Asn Tyr
            100                 105                 110

Glu Asn Gly Lys Asn Asp Tyr Val Lys Ala Leu Pro Gly His Leu Lys
            115                 120                 125

Pro Phe Glu Thr Leu Leu Ser Gln Asn Gln Gly Gly Lys Ala Phe Ile
        130                 135                 140

Val Gly Asp Gln Ile Ser Phe Ala Asp Tyr Asn Leu Leu Asp Leu Leu
145                 150                 155                 160

Leu Ile His Gln Val Leu Ala Pro Gly Cys Leu Asp Asn Phe Pro Leu
                165                 170                 175

Leu Ser Ala Tyr Val Ala Arg Leu Ser Ala Arg Pro Lys Ile Lys Ala
            180                 185                 190

Phe Leu Ser Ser Pro Glu His Val Asn Arg Pro Ile Asn Gly Asn Gly
        195                 200                 205

Lys Gln
    210

<210> SEQ ID NO 17
<211> LENGTH: 210
<212> TYPE: PRT
<213> ORGANISM: Rattus norvegicus

<400> SEQUENCE: 17

Met Pro Pro Tyr Thr Ile Val Tyr Phe Pro Val Arg Gly Arg Cys Glu
1               5                   10                  15

Ala Thr Arg Met Leu Leu Ala Asp Gln Gly Gln Ser Trp Lys Glu Glu
            20                  25                  30

Val Val Thr Ile Asp Val Trp Leu Gln Gly Ser Leu Lys Ser Thr Cys
        35                  40                  45

Leu Tyr Gly Gln Leu Pro Lys Phe Glu Asp Gly Asp Leu Thr Leu Tyr
    50                  55                  60

Gln Ser Asn Ala Ile Leu Arg His Leu Gly Arg Ser Leu Gly Leu Tyr
65                  70                  75                  80

Gly Lys Asp Gln Lys Glu Ala Ala Leu Val Asp Met Val Asn Asp Gly
                85                  90                  95

Val Glu Asp Leu Arg Cys Lys Tyr Gly Thr Leu Ile Tyr Thr Asn Tyr
            100                 105                 110

Glu Asn Gly Lys Asp Asp Tyr Val Lys Ala Leu Pro Gly His Leu Lys
        115                 120                 125

Pro Phe Glu Thr Leu Leu Ser Gln Asn Gln Gly Gly Lys Ala Phe Ile
    130                 135                 140

Val Gly Asn Gln Ile Ser Phe Ala Asp Tyr Asn Leu Leu Asp Leu Leu
145                 150                 155                 160

Leu Val His Gln Val Leu Ala Pro Gly Cys Leu Asp Asn Phe Pro Leu
                165                 170                 175

Leu Ser Ala Tyr Val Ala Arg Leu Ser Ala Arg Pro Lys Ile Lys Ala
            180                 185                 190

Phe Leu Ser Ser Pro Asp His Leu Asn Arg Pro Ile Asn Gly Asn Gly
        195                 200                 205

Lys Gln
    210

<210> SEQ ID NO 18
<211> LENGTH: 207
<212> TYPE: PRT
<213> ORGANISM: Sus scrofa

<400> SEQUENCE: 18

Pro Pro Tyr Thr Ile Thr Tyr Phe Pro Val Arg Gly Arg Cys Glu Ala
1               5                   10                  15

Met Arg Met Leu Leu Ala Asp Gln Asp Gln Ser Trp Lys Glu Glu Val
            20                  25                  30

Val Thr Met Glu Thr Trp Pro Pro Leu Lys Pro Ser Cys Leu Phe Arg
        35                  40                  45

Gln Leu Pro Lys Phe Gln Asp Gly Asp Leu Thr Leu Tyr Gln Ser Asn
    50                  55                  60

Ala Ile Leu Arg His Leu Gly Arg Ser Phe Gly Leu Tyr Gly Lys Asp
65                  70                  75                  80

Gln Lys Glu Ala Ala Leu Val Asp Met Val Asn Asp Gly Val Glu Asp
                85                  90                  95

Leu Arg Cys Lys Tyr Ala Thr Leu Ile Tyr Thr Asn Tyr Glu Ala Gly
            100                 105                 110

Lys Glu Lys Tyr Val Lys Glu Leu Pro Glu His Leu Lys Pro Phe Glu
            115                 120                 125

Thr Leu Leu Ser Gln Asn Gln Gly Gly Gln Ala Phe Val Val Gly Ser
    130                 135                 140

Gln Ile Ser Phe Ala Asp Tyr Asn Leu Leu Asp Leu Leu Arg Ile His
145                 150                 155                 160

Gln Val Leu Asn Pro Ser Cys Leu Asp Ala Phe Pro Leu Leu Ser Ala
                165                 170                 175

Tyr Val Ala Arg Leu Ser Ala Arg Pro Lys Ile Lys Ala Phe Leu Ala
                180                 185                 190

Ser Pro Glu His Val Asn Arg Pro Ile Asn Gly Asn Gly Lys Asn
            195                 200                 205

<210> SEQ ID NO 19
<211> LENGTH: 210
<212> TYPE: PRT
<213> ORGANISM: Bos taurus

<400> SEQUENCE: 19

Met Pro Pro Tyr Thr Ile Val Tyr Phe Pro Val Gln Gly Arg Cys Glu
1               5                   10                  15

Ala Met Arg Met Leu Leu Ala Asp Gln Gly Gln Ser Trp Lys Glu Glu
                20                  25                  30

Val Val Ala Met Gln Ser Trp Leu Gln Gly Pro Leu Lys Ala Ser Cys
            35                  40                  45

Leu Tyr Gly Gln Leu Pro Lys Phe Gln Asp Gly Asp Leu Thr Leu Tyr
        50                  55                  60

Gln Ser Asn Ala Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Val Ser Leu Ile Tyr Thr Asn Tyr
            100                 105                 110

Glu Ala Gly Lys Glu Asp Tyr Val Lys Ala Leu Pro Gln His Leu Lys
        115                 120                 125

Pro Phe Glu Thr Leu Leu Ser Gln Asn Lys Gly Gly Gln Ala Phe Ile
    130                 135                 140

Val Gly Asp Gln Ile Ser Phe Ala Asp Tyr Asn Leu Leu Asp Leu Leu
145                 150                 155                 160

Arg Ile His Gln Val Leu Ala Pro Ser Cys Leu Asp Ser Phe Pro Leu
                165                 170                 175

Leu Ser Ala Tyr Val Ala Arg Leu Asn Ser Arg Pro Lys Leu Lys Ala
                180                 185                 190

Phe Leu Ala Ser Pro Glu His Met Asn Arg Pro Ile Asn Gly Asn Gly
            195                 200                 205

Lys Gln
210

<210> SEQ ID NO 20
<211> LENGTH: 218
<212> TYPE: PRT
<213> ORGANISM: Homo sapiens

<400> SEQUENCE: 20

Met Pro Met Ile Leu Gly Tyr Trp Asp Ile Arg Gly Leu Ala His Ala
1               5                   10                  15

Ile Arg Leu Leu Leu Glu Tyr Thr Asp Ser Ser Tyr Glu Glu Lys Lys
                20                  25                  30

Tyr Thr Met Gly Asp Ala Pro Asp Tyr Asp Arg Ser Gln Trp Leu Asn
            35                  40                  45

Glu Lys Phe Lys Leu Gly Leu Asp Phe Pro Asn Leu Pro Tyr Leu Ile
        50                  55                  60

Asp Gly Ala His Lys Ile Thr Gln Ser Asn Ala Ile Leu Cys Tyr Ile
65                  70                  75                  80

Ala Arg Lys His Asn Leu Cys Gly Glu Thr Glu Glu Lys Ile Arg
                85                  90                  95

Val Asp Ile Leu Glu Asn Gln Thr Met Asp Asn His Met Gln Leu Gly
                100                 105                 110

Met Ile Cys Tyr Asn Pro Glu Phe Glu Lys Leu Lys Pro Lys Tyr Leu
            115                 120                 125

Glu Glu Leu Pro Glu Lys Leu Lys Leu Tyr Ser Glu Phe Leu Gly Lys
        130                 135                 140

Arg Pro Trp Phe Ala Gly Asn Lys Ile Thr Phe Val Asp Phe Leu Val
145                 150                 155                 160

Tyr Asp Val Leu Asp Leu His Arg Ile Phe Glu Pro Lys Cys Leu Asp
                165                 170                 175

Ala Phe Pro Asn Leu Lys Asp Phe Ile Ser Arg Phe Glu Gly Leu Glu
            180                 185                 190

Lys Ile Ser Ala Tyr Met Lys Ser Ser Arg Phe Leu Pro Arg Pro Val
            195                 200                 205

Phe Ser Lys Met Ala Val Trp Gly Asn Lys
        210                 215

<210> SEQ ID NO 21
<211> LENGTH: 218
<212> TYPE: PRT
<213> ORGANISM: Rattus norvegicus

<400> SEQUENCE: 21

Met Pro Met Ile Leu Gly Tyr Trp Asn Val Arg Gly Leu Thr His Pro
1               5                   10                  15

Ile Arg Leu Leu Leu Glu Tyr Thr Asp Ser Ser Tyr Glu Glu Lys Arg
                20                  25                  30

Tyr Ala Met Gly Asp Ala Pro Asp Tyr Asp Arg Ser Gln Trp Leu Asn
            35                  40                  45

Glu Lys Phe Lys Leu Gly Leu Asp Phe Pro Asn Leu Pro Tyr Leu Ile
        50                  55                  60

Asp Gly Ser Arg Lys Ile Thr Gln Ser Asn Ala Ile Met Arg Tyr Leu
65                  70                  75                  80

Ala Arg Lys His His Leu Cys Gly Glu Thr Glu Glu Glu Arg Ile Arg
                85                  90                  95

Ala Asp Ile Val Glu Asn Gln Val Met Asp Asn Arg Met Gln Leu Ile
                100                 105                 110

Met Leu Cys Tyr Asn Pro Asp Phe Glu Lys Gln Lys Pro Glu Phe Leu
            115                 120                 125

Lys Thr Ile Pro Glu Lys Met Lys Leu Tyr Ser Glu Phe Leu Gly Lys
        130                 135                 140

Arg Pro Trp Phe Ala Gly Asp Lys Val Thr Tyr Val Asp Phe Leu Ala

```
145                 150                 155                 160

Tyr Asp Ile Leu Asp Gln Tyr His Ile Phe Glu Pro Lys Cys Leu Asp
                165                 170                 175

Ala Phe Pro Asn Leu Lys Asp Phe Leu Ala Arg Phe Glu Gly Leu Lys
                180                 185                 190

Lys Ile Ser Ala Tyr Met Lys Ser Arg Tyr Leu Ser Thr Pro Ile
            195                 200                 205

Phe Ser Lys Leu Ala Gln Trp Ser Asn Lys
        210                 215

<210> SEQ ID NO 22
<211> LENGTH: 218
<212> TYPE: PRT
<213> ORGANISM: Fasciola hepatica

<400> SEQUENCE: 22

Met Pro Ala Lys Leu Gly Tyr Trp Lys Ile Arg Gly Leu Gln Gln Pro
1               5                   10                  15

Val Arg Leu Leu Leu Glu Tyr Leu Gly Glu Glu Tyr Glu Glu His Leu
                20                  25                  30

Tyr Gly Arg Asp Asp Arg Glu Lys Trp Phe Gly Asp Lys Phe Asn Met
            35                  40                  45

Gly Leu Asp Leu Pro Asn Leu Pro Tyr Tyr Ile Asp Asp Lys Cys Lys
        50                  55                  60

Leu Thr Gln Ser Val Ala Ile Met Arg Tyr Ile Ala Asp Lys His Gly
65                  70                  75                  80

Met Leu Gly Thr Thr Pro Glu Glu Arg Ala Arg Ile Ser Met Ile Glu
                85                  90                  95

Gly Ala Ala Met Asp Leu Arg Met Gly Phe Val Arg Val Cys Tyr Asn
                100                 105                 110

Pro Lys Phe Glu Glu Val Lys Gly Asp Tyr Leu Lys Glu Leu Pro Thr
            115                 120                 125

Thr Leu Lys Met Trp Ser Asn Phe Leu Gly Asp Arg His Tyr Leu Thr
        130                 135                 140

Gly Ser Pro Val Ser His Val Asp Phe Met Val Tyr Glu Ala Leu Asp
145                 150                 155                 160

Cys Ile Arg Tyr Leu Ala Pro Gln Cys Leu Glu Asp Phe Pro Lys Leu
                165                 170                 175

Lys Glu Phe Lys Ser Arg Ile Glu Asp Leu Pro Lys Ile Lys Ala Tyr
            180                 185                 190

Met Glu Ser Glu Lys Phe Ile Lys Trp Pro Leu Asn Ser Trp Ile Ala
        195                 200                 205

Ser Phe Gly Gly Asp Ala Ala Pro Ala
    210                 215

<210> SEQ ID NO 23
<211> LENGTH: 218
<212> TYPE: PRT
<213> ORGANISM: Mus musculus

<400> SEQUENCE: 23

Met Pro Met Ile Leu Gly Tyr Trp Asn Val Arg Gly Leu Thr His Pro
1               5                   10                  15

Ile Arg Met Leu Leu Glu Tyr Thr Asp Ser Ser Tyr Asp Glu Lys Arg
                20                  25                  30

Tyr Thr Met Gly Asp Ala Pro Asp Phe Asp Arg Ser Gln Trp Leu Asn
```

```
                35                  40                  45
Glu Lys Phe Lys Leu Gly Leu Asp Phe Pro Asn Leu Pro Tyr Leu Ile
 50                  55                  60

Asp Gly Ser His Lys Ile Thr Gln Ser Asn Ala Ile Leu Arg Tyr Leu
 65                  70                  75                  80

Ala Arg Lys His His Leu Asp Gly Glu Thr Glu Glu Arg Ile Arg
                 85                  90                  95

Ala Asp Ile Val Glu Asn Gln Val Met Asp Thr Arg Met Gln Leu Ile
                100                 105                 110

Met Leu Cys Tyr Asn Pro Asp Phe Glu Lys Gln Lys Pro Glu Phe Leu
            115                 120                 125

Lys Thr Ile Pro Glu Lys Met Lys Leu Tyr Ser Glu Phe Leu Gly Lys
        130                 135                 140

Arg Pro Trp Phe Ala Gly Asp Lys Val Thr Tyr Val Asp Phe Leu Ala
145                 150                 155                 160

Tyr Asp Ile Leu Asp Gln Tyr Arg Met Phe Glu Pro Lys Cys Leu Asp
                165                 170                 175

Ala Phe Pro Asn Leu Arg Asp Phe Leu Ala Arg Phe Glu Gly Leu Lys
            180                 185                 190

Lys Ile Ser Ala Tyr Met Lys Ser Ser Arg Tyr Ile Ala Thr Pro Ile
        195                 200                 205

Phe Ser Lys Met Ala His Trp Ser Asn Lys
210                 215

<210> SEQ ID NO 24
<211> LENGTH: 218
<212> TYPE: PRT
<213> ORGANISM: Oryctolagus cuniculus

<400> SEQUENCE: 24

Met Pro Met Thr Leu Gly Tyr Trp Asp Val Arg Gly Leu Ala Leu Pro
  1               5                  10                  15

Ile Arg Met Leu Leu Glu Tyr Thr Asp Thr Ser Tyr Glu Glu Lys Lys
                 20                  25                  30

Tyr Thr Met Gly Asp Ala Pro Asn Tyr Asp Gln Ser Lys Trp Leu Ser
             35                  40                  45

Glu Lys Phe Thr Leu Gly Leu Asp Phe Pro Asn Leu Pro Tyr Leu Ile
 50                  55                  60

Asp Gly Thr His Lys Leu Thr Gln Ser Asn Ala Ile Leu Arg Tyr Leu
 65                  70                  75                  80

Ala Arg Lys His Gly Leu Cys Gly Glu Thr Glu Glu Glu Arg Ile Arg
                 85                  90                  95

Val Asp Ile Leu Glu Asn Gln Leu Met Asp Asn Arg Phe Gln Leu Val
                100                 105                 110

Asn Val Cys Tyr Ser Pro Asp Phe Glu Lys Leu Lys Pro Glu Tyr Leu
            115                 120                 125

Lys Gly Leu Pro Glu Lys Leu Gln Leu Tyr Ser Gln Phe Leu Gly Ser
        130                 135                 140

Leu Pro Trp Phe Ala Gly Asp Lys Ile Thr Phe Ala Asp Phe Leu Val
145                 150                 155                 160

Tyr Asp Val Leu Asp Gln Asn Arg Ile Phe Val Pro Gly Cys Leu Asp
                165                 170                 175

Ala Phe Pro Asn Leu Lys Asp Phe His Val Arg Phe Glu Gly Leu Pro
            180                 185                 190
```

```
Lys Ile Ser Ala Tyr Met Lys Ser Arg Phe Ile Arg Val Pro Val
            195                 200                 205
Phe Leu Lys Lys Ala Thr Trp Thr Gly Ile
            210                 215

<210> SEQ ID NO 25
<211> LENGTH: 209
<212> TYPE: PRT
<213> ORGANISM: Anopheles gambiae

<400> SEQUENCE: 25

Met Asp Phe Tyr Tyr Leu Pro Gly Ser Ala Pro Cys Arg Ala Val Gln
1               5                   10                  15
Met Thr Ala Ala Ala Val Gly Val Glu Leu Asn Leu Lys Leu Thr Asp
            20                  25                  30
Leu Met Lys Gly Glu His Met Lys Pro Glu Phe Leu Lys Leu Asn Pro
        35                  40                  45
Gln His Cys Ile Pro Thr Leu Val Asp Asn Gly Phe Ala Leu Trp Glu
    50                  55                  60
Ser Arg Ala Ile Gln Ile Tyr Leu Ala Glu Lys Tyr Gly Lys Asp Asp
65                  70                  75                  80
Lys Leu Tyr Pro Lys Asp Pro Gln Lys Arg Ala Val Val Asn Gln Arg
                85                  90                  95
Leu Tyr Phe Asp Met Gly Thr Leu Tyr Gln Arg Phe Ala Asp Tyr His
            100                 105                 110
Tyr Pro Gln Ile Phe Ala Lys Gln Pro Ala Asn Pro Glu Asn Glu Lys
        115                 120                 125
Lys Met Lys Asp Ala Val Gly Phe Leu Asn Thr Phe Leu Glu Gly Gln
    130                 135                 140
Glu Tyr Ala Ala Gly Asn Asp Leu Thr Ile Ala Asp Leu Ser Leu Ala
145                 150                 155                 160
Ala Thr Ile Ala Thr Tyr Glu Val Ala Gly Phe Asp Phe Ala Pro Tyr
                165                 170                 175
Pro Asn Val Ala Ala Trp Phe Ala Arg Cys Lys Ala Asn Ala Pro Gly
            180                 185                 190
Tyr Ala Leu Asn Gln Ala Gly Ala Asp Glu Phe Lys Ala Lys Phe Leu
        195                 200                 205
Ser

<210> SEQ ID NO 26
<211> LENGTH: 210
<212> TYPE: PRT
<213> ORGANISM: Musca domestica

<400> SEQUENCE: 26

Met Asp Phe Tyr Tyr Leu Pro Leu Ser Ala Pro Cys Arg Ser Val Ile
1               5                   10                  15
Met Thr Ala Lys Ala Leu Gly Ile Glu Leu Asn Lys Lys Leu Leu Asn
            20                  25                  30
Leu Phe Glu Gly Glu His Leu Lys Pro Glu Phe Leu Lys Ile Asn Pro
        35                  40                  45
Gln His Thr Ile Pro Thr Leu Val Asp Asn Gly Phe Ala Met Trp Glu
    50                  55                  60
Ser Arg Ala Ile Met Val Tyr Leu Val Glu Lys Tyr Gly Lys Gln Asn
65                  70                  75                  80
Asp Pro Leu Tyr Pro Ser Cys Pro Lys Lys Arg Ala Leu Ile Asn Gln
```

```
                         85                  90                  95
Arg Leu Tyr Phe Asp Met Gly Thr Leu Trp Lys Ser Tyr Ala Asp Tyr
                100                 105                 110

Thr Tyr Pro Gln Phe Arg Glu Asn Lys Pro Ala Asp Pro Glu Leu Phe
            115                 120                 125

Lys Lys Phe Glu Ser Ala Leu Glu Phe Leu Asn Ile Phe Leu Ser Gln
        130                 135                 140

Ser Lys Tyr Ala Ala Gly Glu Thr Met Thr Leu Ala Asp Leu Ala Ile
145                 150                 155                 160

Leu Ala Ser Val Ser Thr Phe Asp Val Val Gln Met Asp Leu Ser Lys
                165                 170                 175

Tyr Glu His Ile Leu Arg Trp Tyr Asn Met Leu Lys Asp Thr Ala Pro
                180                 185                 190

Gly Ala Ala Glu Asn Trp Ala Gly Cys Leu Glu Met Lys Lys Tyr Phe
            195                 200                 205

Lys Lys
    210

<210> SEQ ID NO 27
<211> LENGTH: 210
<212> TYPE: PRT
<213> ORGANISM: Musca domestica

<400> SEQUENCE: 27

Met Asp Phe Tyr Tyr Leu Pro Leu Ser Ala Pro Cys Arg Ser Val Ile
1               5                   10                  15

Met Thr Ala Lys Ala Leu Gly Ile Glu Leu Asn Lys Lys Leu Leu Asn
            20                  25                  30

Leu Phe Glu Gly Glu His Leu Lys Pro Glu Phe Leu Lys Ile Asn Pro
        35                  40                  45

Gln His Thr Ile Pro Thr Leu Val Asp Asn Gly Phe Ala Met Trp Glu
    50                  55                  60

Ser Arg Ala Ile Met Val Tyr Leu Val Glu Lys Tyr Gly Lys Gln Asn
65                  70                  75                  80

Asp Pro Leu Tyr Pro Ser Cys Pro Lys Lys Arg Ala Leu Ile Asn Gln
                85                  90                  95

Arg Leu Tyr Phe Asp Met Gly Thr Leu Trp Lys Ser Tyr Ala Asp Tyr
                100                 105                 110

Thr Tyr Pro Gln Phe Arg Glu Asn Lys Pro Ala Asp Pro Glu Leu Phe
            115                 120                 125

Lys Lys Phe Glu Ser Ala Leu Glu Phe Leu Asn Ile Phe Leu Ser Gln
        130                 135                 140

Ser Lys Tyr Ala Ala Gly Gln Thr Met Thr Leu Ala Asp Leu Ala Ile
145                 150                 155                 160

Leu Ala Ser Val Ser Thr Phe Asp Val Val Gln Met Asp Leu Ser Lys
                165                 170                 175

Tyr Glu His Ile Leu Arg Trp Tyr Asn Met Leu Lys Asp Thr Ala Pro
                180                 185                 190

Gly Ala Ala Glu Asn Trp Ala Gly Cys Leu Glu Met Lys Lys Tyr Phe
            195                 200                 205

Lys Lys
    210

<210> SEQ ID NO 28
<211> LENGTH: 216
```

<212> TYPE: PRT
<213> ORGANISM: Drosophila melanogaster

<400> SEQUENCE: 28

Met Asp Phe Tyr Tyr Ser Pro Arg Gly Ser Gly Cys Arg Thr Val Ile
1               5                   10                  15

Met Val Ala Lys Ala Leu Gly Val Lys Leu Asn Met Lys Leu Leu Asn
            20                  25                  30

Thr Leu Glu Lys Asp Gln Leu Lys Pro Glu Phe Val Lys Leu Asn Pro
        35                  40                  45

Gln His Thr Ile Pro Thr Leu Val Asp Asn Gly Phe Ser Ile Trp Glu
    50                  55                  60

Ser Arg Ala Ile Ala Val Tyr Leu Val Glu Lys Tyr Gly Lys Asp Asp
65                  70                  75                  80

Thr Leu Phe Pro Lys Asp Pro Lys Lys Gln Ala Leu Val Asn Gln Arg
                85                  90                  95

Leu Tyr Phe Asp Met Gly Thr Leu Tyr Asp Ser Phe Ala Lys Tyr Tyr
            100                 105                 110

Tyr Pro Leu Phe His Thr Gly Lys Pro Gly Ser Asp Glu Asp Phe Lys
        115                 120                 125

Lys Ile Glu Ser Ser Phe Glu Tyr Leu Asn Ile Phe Leu Glu Gly Gln
    130                 135                 140

Asn Tyr Val Ala Gly Asp His Leu Thr Val Ala Asp Ile Ala Ile Leu
145                 150                 155                 160

Ser Thr Val Ser Thr Phe Glu Ile Phe Asp Phe Asp Leu Asn Lys Tyr
                165                 170                 175

Pro Asn Val Ala Arg Trp Tyr Ala Asn Ala Lys Lys Val Thr Pro Gly
            180                 185                 190

Trp Glu Glu Asn Trp Lys Gly Ala Val Glu Leu Lys Gly Val Phe Asp
        195                 200                 205

Ala Arg Gln Ala Ala Ala Lys Gln
    210                 215

<210> SEQ ID NO 29
<211> LENGTH: 215
<212> TYPE: PRT
<213> ORGANISM: Drosophila melanogaster

<400> SEQUENCE: 29

Met Asp Phe Tyr Tyr Ser Pro Arg Ser Gly Ser Arg Thr Ile Ile
1               5                   10                  15

Met Val Ala Lys Ala Leu Gly Leu Glu Leu Asn Lys Lys Gln Leu Arg
            20                  25                  30

Ile Thr Glu Gly Glu His Leu Lys Pro Glu Phe Leu Lys Leu Asn Pro
        35                  40                  45

Gln His Thr Ile Pro Thr Leu Val Asp Asn Gly Phe Ala Ile Trp Glu
    50                  55                  60

Ser Arg Ala Ile Ala Val Tyr Leu Val Glu Lys Tyr Gly Lys Asp Asp
65                  70                  75                  80

Ser Leu Phe Pro Asn Asp Pro Gln Lys Arg Ala Leu Ile Asn Gln Arg
                85                  90                  95

Leu Tyr Phe Asp Met Gly Thr Leu His Asp Ser Phe Met Lys Tyr Tyr
            100                 105                 110

Tyr Pro Phe Ile Arg Thr Gly Gln Leu Gly Asn Ala Glu Asn Tyr Lys
        115                 120                 125

Lys Val Glu Ala Ala Phe Glu Phe Leu Asp Ile Phe Leu Glu Gly Gln
            130                 135                 140

Asp Tyr Val Ala Gly Ser Gln Leu Thr Val Ala Asp Ile Ala Ile Leu
145                 150                 155                 160

Ser Ser Val Ser Thr Phe Glu Val Val Glu Phe Asp Ile Ser Lys Tyr
                    165                 170                 175

Pro Asn Val Ala Arg Trp Tyr Ala Asn Ala Lys Lys Ile Thr Pro Gly
                180                 185                 190

Trp Asp Glu Asn Trp Lys Gly Leu Leu Gln Met Lys Thr Met Tyr Glu
            195                 200                 205

Ala Gln Lys Ala Ser Leu Lys
        210                 215

<210> SEQ ID NO 30
<211> LENGTH: 224
<212> TYPE: PRT
<213> ORGANISM: Zea mays

<400> SEQUENCE: 30

Met Ala Glu Glu Lys Lys Gln Gly Leu Gln Leu Leu Asp Phe Trp Val
1               5                   10                  15

Ser Pro Phe Gly Gln Arg Cys Arg Ile Ala Met Asp Glu Lys Gly Leu
                20                  25                  30

Ala Tyr Glu Tyr Leu Glu Gln Asp Leu Gly Asn Lys Ser Glu Leu Leu
            35                  40                  45

Leu Arg Ala Asn Pro Val His Lys Lys Ile Pro Val Leu Leu His Asp
    50                  55                  60

Gly Arg Pro Val Cys Glu Ser Leu Val Ile Val Gln Tyr Leu Asp Glu
65                  70                  75                  80

Ala Phe Pro Ala Ala Pro Ala Leu Leu Pro Ala Asp Pro Tyr Ala
                85                  90                  95

Arg Ala Gln Ala Arg Phe Trp Ala Asp Tyr Val Asp Lys Lys Leu Tyr
            100                 105                 110

Asp Cys Gly Thr Arg Leu Trp Lys Leu Lys Gly Asp Gly Gln Ala Gln
        115                 120                 125

Ala Arg Ala Glu Met Val Glu Ile Leu Arg Thr Leu Glu Gly Ala Leu
    130                 135                 140

Gly Asp Gly Pro Phe Phe Gly Gly Asp Ala Leu Gly Phe Val Asp Val
145                 150                 155                 160

Ala Leu Val Pro Phe Thr Ser Trp Phe Leu Ala Tyr Asp Arg Phe Gly
                165                 170                 175

Gly Val Ser Val Glu Lys Glu Cys Pro Arg Leu Ala Ala Trp Ala Lys
            180                 185                 190

Arg Cys Ala Glu Arg Pro Ser Val Ala Lys Asn Leu Tyr Pro Pro Glu
        195                 200                 205

Lys Val Tyr Asp Phe Val Cys Gly Met Lys Lys Arg Leu Gly Ile Glu
    210                 215                 220

<210> SEQ ID NO 31
<211> LENGTH: 224
<212> TYPE: PRT
<213> ORGANISM: Mesembryanthemum crystallinum

<400> SEQUENCE: 31

Met Gly Glu Glu Val Ile Leu Leu Asp Phe Trp Pro Ser Met Phe Gly
1               5                   10                  15

Met Arg Leu Arg Ile Ala Leu Ala Glu Lys Gly Val Lys His Glu Arg
            20                  25                  30

Lys Glu Glu Asp Leu Leu Ile Gly Lys Ser Pro Leu Leu Leu Gln Leu
        35                  40                  45

Asn Pro Val His Lys Lys Ile Pro Val Leu Val His Asn Gly Lys Pro
50                  55                  60

Ile Asn Glu Ser Met Ile Ala Val Gln Tyr Ile Asp Glu Val Trp Asn
65                  70                  75                  80

Glu Lys Ser Pro Ser Leu Leu Pro Ser Asp Pro Tyr Gln Arg Ala Gln
                85                  90                  95

Ala Arg Phe Trp Ala Asp Phe Ile Asp Lys Lys Leu Tyr Asp Glu Cys
            100                 105                 110

Arg Lys Ile Tyr Thr Thr Lys Glu Ala Glu Ile Gly Glu Glu Thr Tyr
        115                 120                 125

Lys Gly Phe Leu Glu Ile Ile Lys Val Leu Glu Ala Glu Val Gly Glu
130                 135                 140

Lys Ser Tyr Phe Gly Gly Asp Thr Phe Gly Phe Val Asp Val Ala Leu
145                 150                 155                 160

Ile Pro Phe Tyr Ser Trp Phe Tyr Ala Leu Glu Met Leu Gly Lys Phe
                165                 170                 175

Asn Ile Glu Thr Glu Cys Pro Lys Leu Ile Ala Trp Ala Lys Arg Cys
            180                 185                 190

Met Glu Arg Glu Ser Val Ser Lys Ser Leu Pro Asp Arg His Lys Ile
        195                 200                 205

Tyr Asp Phe Ile Thr Leu Gln Leu Arg Lys Ala Leu Gly Val Asp Gln
210                 215                 220

<210> SEQ ID NO 32
<211> LENGTH: 219
<212> TYPE: PRT
<213> ORGANISM: Arabidopsis thaliana

<400> SEQUENCE: 32

Met Ala Asn Glu Val Ile Leu Leu Asp Phe Trp Pro Ser Met Phe Gly
1               5                   10                  15

Met Arg Thr Arg Ile Ala Leu Arg Glu Lys Gly Val Glu Phe Glu Tyr
            20                  25                  30

Arg Glu Glu Asp Leu Arg Asn Lys Ser Pro Leu Leu Leu Gln Met Asn
        35                  40                  45

Pro Ile His Lys Lys Ile Pro Val Leu Ile His Asn Gly Lys Pro Val
50                  55                  60

Asn Glu Ser Ile Ile Gln Val Gln Tyr Ile Asp Glu Val Trp Ser His
65                  70                  75                  80

Lys Asn Pro Ile Leu Pro Ser Asp Pro Tyr Leu Arg Ala Gln Ala Arg
                85                  90                  95

Phe Trp Ala Asp Phe Ile Asp Lys Lys Leu Tyr Asp Ala Gln Arg Lys
            100                 105                 110

Val Trp Ala Thr Lys Gly Glu Glu Gln Glu Ala Gly Lys Lys Asp Phe
        115                 120                 125

Ile Glu Ile Leu Lys Thr Leu Glu Ser Glu Leu Gly Asp Lys Pro Tyr
130                 135                 140

Phe Ser Gly Asp Asp Phe Gly Tyr Val Asp Ile Ala Leu Ile Gly Phe
145                 150                 155                 160

Tyr Thr Trp Phe Pro Ala Tyr Glu Lys Phe Ala Asn Phe Ser Ile Glu
                165                 170                 175

```
Ser Glu Val Pro Lys Leu Ile Ala Trp Val Lys Lys Cys Leu Gln Arg
            180                 185                 190

Glu Ser Val Ala Lys Ser Leu Pro Asp Pro Glu Lys Val Thr Glu Phe
            195                 200                 205

Val Ser Glu Leu Arg Lys Lys Phe Val Pro Glu
    210                 215

<210> SEQ ID NO 33
<211> LENGTH: 230
<212> TYPE: PRT
<213> ORGANISM: Vigna radiate

<400> SEQUENCE: 33

Glu Leu Lys Cys Phe Asp Gly Phe Lys Ser Gly Arg Ser Asp Pro Ser
1               5                   10                  15

Gly Ile Ile Gly Ser Pro Phe Val Cys Arg Val Lys Ile Ala Leu Lys
            20                  25                  30

Leu Lys Gly Val Glu Tyr Lys Tyr Val Glu Glu Asn Phe Arg Asn Lys
        35                  40                  45

Ser Glu Gln Leu Leu Lys Tyr Asn Pro Val His Lys Lys Val Pro Val
    50                  55                  60

Phe Val His Gly Asp Lys Pro Leu Pro Glu Ser Leu Val Ile Val Glu
65                  70                  75                  80

Tyr Ile Asp Glu Thr Trp Asn Asn Pro Ile Leu Ala Ser Asp Pro
                85                  90                  95

Tyr Gln Arg Ala Leu Ala Arg Phe Trp Ser Lys Phe Ile Asp Asp Lys
            100                 105                 110

Ile Val Gly Ala Ser Trp Lys Ser Val Phe Thr Val Asp Glu Lys Glu
        115                 120                 125

Arg Glu Lys Asn Ile Ala Glu Thr Tyr Glu Ser Leu Gln Phe Leu Glu
    130                 135                 140

Asn Glu Ile Lys Glu Lys Lys Phe Phe Gly Gly Glu Glu Leu Gly Leu
145                 150                 155                 160

Val Asp Ile Ala Ala Val Tyr Val Ala Phe Trp Ile Pro Leu Ile Gln
                165                 170                 175

Glu Ile Ala Gly Leu Glu Leu Leu Thr Ser Glu Lys Phe Pro Asn Leu
            180                 185                 190

Tyr Arg Trp Ser Gln Glu Phe Leu Asn His Pro Ile Val Lys Glu Ser
        195                 200                 205

Leu Pro Pro Arg Asp Pro Val Phe Ala Phe Lys Gly Arg Tyr Glu
    210                 215                 220

Gly Leu Phe Ser Ser Lys
225                 230

<210> SEQ ID NO 34
<211> LENGTH: 218
<212> TYPE: PRT
<213> ORGANISM: Carica papaya

<400> SEQUENCE: 34

Met Ala Asp Glu Val Val Leu Leu Asp Phe Trp Pro Ser Pro Phe Gly
1               5                   10                  15

Met Arg Ile Arg Ile Ala Leu Ala Glu Lys Gly Ile His Tyr Glu Tyr
            20                  25                  30

Lys Glu Glu Asn Leu Arg Asn Lys Ser Pro Leu Leu Leu Gln Met Asn
        35                  40                  45
```

Pro Val His Lys Lys Ile Pro Val Leu Ile His Asn Gly Lys Pro Ile
    50                  55                  60

Cys Glu Ser Leu Ile Gln Ile Gln Tyr Ile Asp Glu Val Trp Ser Asp
 65                  70                  75                  80

Lys Ala Pro Leu Leu Pro Ser Asp Pro Tyr Gln Arg Ala Gln Ala Arg
                 85                  90                  95

Phe Trp Ala Asp Tyr Val Asp Lys Lys Met Tyr Glu Ala Gly Arg Arg
            100                 105                 110

Val Trp Thr Thr Lys Gly Glu Gln Glu Gly Ala Lys Lys Glu Phe
        115                 120                 125

Ile Glu Ile Leu Lys Thr Leu Glu Gly Glu Leu Gly Glu Lys Pro Tyr
    130                 135                 140

Phe Gly Glu Ser Phe Gly Tyr Val Asp Leu Thr Phe Ile Pro Phe
145                 150                 155                 160

Tyr Thr Trp Phe Ser Val Tyr Glu Ser Phe Gly Lys Met Ser Ile Glu
                165                 170                 175

Ala Glu Cys Pro Lys Leu Phe Ser Trp Val Lys Arg Cys Leu Glu Lys
            180                 185                 190

Glu Ser Val Ser Lys Ser Leu Pro Asp Gln Asp Lys Val Tyr Gly Phe
        195                 200                 205

Val Leu Glu Leu Arg Lys Ala Leu Gly Ile
    210                 215

<210> SEQ ID NO 35
<211> LENGTH: 213
<212> TYPE: PRT
<213> ORGANISM: Triticum aestivum

<400> SEQUENCE: 35

Met Ala Thr Ala Lys Pro Ile Leu Tyr Gly Ala Trp Ile Ser Ser Cys
 1                   5                  10                  15

Ser His Arg Val Arg Ile Ala Leu Asn Leu Lys Gly Val Asp Tyr Glu
            20                  25                  30

Tyr Lys Ala Val Asn Pro Arg Thr Asp Pro Asp Tyr Glu Lys Ile Asn
        35                  40                  45

Pro Ile Lys Tyr Ile Pro Ala Leu Val Asp Gly Asp Phe Val Leu Ser
    50                  55                  60

Asp Ser Leu Ala Ile Met Leu Tyr Leu Glu Asp Lys Tyr Pro Gln His
 65                  70                  75                  80

Pro Leu Val Pro Lys Asp Ile Lys Thr Lys Gly Leu Asp Leu Gln Ile
                 85                  90                  95

Ala Asn Ile Val Cys Ser Ser Ile Gln Pro Leu Gln Gly Tyr Gly Val
            100                 105                 110

Ile Gly Leu His Glu Gly Arg Leu Ser Pro Asp Glu Ser Leu Glu Val
        115                 120                 125

Val Gln Arg Tyr Ile Asp Lys Gly Phe Arg Ala Ile Glu Lys Leu Leu
    130                 135                 140

Asp Gly Cys Asp Ser Lys Tyr Cys Val Gly Asp Glu Val His Leu Gly
145                 150                 155                 160

Asp Val Cys Leu Ala Pro Gln Ile His Ala Ala Ile Asn Arg Phe Gln
                165                 170                 175

Ile Asp Met Thr Lys Tyr Pro Ile Leu Ser Arg Leu His Asp Ala Tyr
            180                 185                 190

Met Lys Ile Pro Ala Phe Gln Ala Ala Leu Pro Gln Asn Gln Pro Asp

```
                195                 200                 205
Ala Pro Ser Ala Lys
    210

<210> SEQ ID NO 36
<211> LENGTH: 221
<212> TYPE: PRT
<213> ORGANISM: Dianthus caryophyllus

<400> SEQUENCE: 36

Met Ser Ser Ser Glu Thr Gln Lys Met Gln Leu Tyr Ser Phe Ser Leu
1               5                   10                  15

Ser Ser Cys Ala Trp Arg Val Arg Ile Ala Leu His Leu Lys Gly Leu
            20                  25                  30

Asp Phe Glu Tyr Lys Ala Val Asp Leu Phe Lys Gly Glu His Leu Thr
        35                  40                  45

Pro Glu Phe Leu Lys Leu Asn Pro Leu Gly Tyr Val Pro Val Leu Val
    50                  55                  60

His Gly Asp Ile Val Ile Ala Asp Ser Leu Ala Ile Ile Met Tyr Leu
65                  70                  75                  80

Glu Glu Lys Phe Pro Glu Asn Pro Leu Leu Pro Gln Asp Leu Gln Lys
                85                  90                  95

Arg Ala Leu Asn Tyr Gln Ala Ala Asn Ile Val Thr Ser Asn Ile Gln
            100                 105                 110

Pro Leu Gln Asn Leu Ala Val Leu Asn Tyr Ile Glu Glu Lys Leu Gly
        115                 120                 125

Ser Asp Glu Lys Leu Ser Trp Ala Lys His His Ile Lys Lys Gly Phe
    130                 135                 140

Ser Ala Leu Glu Lys Leu Leu Lys Gly His Ala Gly Lys Tyr Ala Thr
145                 150                 155                 160

Gly Asp Glu Val Gly Leu Ala Asp Leu Phe Leu Ala Pro Gln Ile Ile
                165                 170                 175

Ala Ser Ile Thr Gly Phe Gly Met Asp Met Ala Glu Phe Pro Leu Leu
            180                 185                 190

Lys Ser Leu Asn Asp Ala Tyr Leu Lys Tyr Gln His Phe Arg Met Arg
        195                 200                 205

Cys Gln Arg Ile Ser Pro Met Leu Asp Glu Ala Lys Ser
    210                 215                 220

<210> SEQ ID NO 37
<211> LENGTH: 225
<212> TYPE: PRT
<213> ORGANISM: Euphorbia esula

<400> SEQUENCE: 37

Met Ala Ser Val Glu Gln Pro Asn Lys Pro Lys Leu Lys Leu Tyr Ser
1               5                   10                  15

Tyr Phe Arg Ser Ser Cys Ser Phe Arg Val Arg Ile Ala Leu Asn Leu
            20                  25                  30

Lys Gly Leu Asp Tyr Glu Tyr Val Pro Val Asn Leu Leu Lys Gly Glu
        35                  40                  45

Gln Phe Thr Pro Glu Phe Leu Lys Ile Asn Pro Ile Gly Tyr Val Pro
    50                  55                  60

Ala Leu Val Asp Gly Glu Asp Val Ile Ser Asp Ser Phe Ala Ile Leu
65                  70                  75                  80

Met Tyr Leu Glu Glu Lys Tyr Pro Glu His Pro Ile Leu Pro Ala Asp
```

```
                        85                  90                  95
Ile His Lys Lys Ala Ile Asn Tyr Gln Ala Asn Ile Val Ser Ser
                100                 105                 110

Ser Ile Gln Pro Leu Gln Asn Leu Ala Val Leu Asn Phe Ile Gly Glu
            115                 120                 125

Lys Val Ser Pro Asp Glu Lys Val Pro Trp Val Gln Arg His Ile Ser
130                 135                 140

Lys Gly Phe Ala Ala Leu Glu Lys Leu Gln Gly His Ala Gly Arg
145                 150                 155                 160

Phe Ala Thr Gly Asp Glu Val Tyr Leu Ala Asp Leu Phe Leu Glu Pro
                165                 170                 175

Gln Ile His Ala Ala Ile Thr Arg Phe Asn Val Asp Met Thr Gln Phe
                180                 185                 190

Pro Leu Leu Leu Arg Leu His Glu Ala Tyr Ser Gln Leu Pro Glu Phe
                195                 200                 205

Gln Asn Ala Met Pro Asp Lys Gln Pro Asp Ser Thr Ser Pro Thr Ala
210                 215                 220

Ser
225

<210> SEQ ID NO 38
<211> LENGTH: 240
<212> TYPE: PRT
<213> ORGANISM: Mus musculus

<400> SEQUENCE: 38

Met Val Leu Glu Leu Tyr Leu Asp Leu Leu Ser Gln Pro Cys Arg Ala
1               5                   10                  15

Ile Tyr Ile Phe Ala Lys Lys Asn Asn Ile Pro Phe Gln Met His Thr
                20                  25                  30

Val Glu Leu Arg Lys Gly Glu His Leu Ser Asp Ala Phe Ala Arg Val
            35                  40                  45

Asn Pro Met Lys Arg Val Pro Ala Met Met Asp Gly Gly Phe Thr Leu
50                  55                  60

Cys Glu Ser Val Ala Ile Leu Leu Tyr Leu Ala His Lys Tyr Lys Val
65                  70                  75                  80

Pro Asp His Trp Tyr Pro Gln Asp Leu Gln Ala Arg Ala Arg Val Asp
                85                  90                  95

Glu Tyr Leu Ala Trp Gln His Thr Gly Leu Arg Arg Ser Cys Leu Arg
                100                 105                 110

Ala Leu Trp His Lys Val Met Phe Pro Val Phe Leu Gly Glu Gln Ile
            115                 120                 125

Pro Pro Glu Thr Leu Ala Ala Thr Leu Ala Glu Leu Asp Val Asn Leu
130                 135                 140

Gln Val Leu Glu Asp Lys Phe Leu Gln Asp Lys Asp Phe Leu Val Gly
145                 150                 155                 160

Pro His Ile Ser Leu Ala Asp Leu Val Ala Ile Thr Glu Leu Met His
                165                 170                 175

Pro Val Gly Gly Gly Cys Pro Val Phe Glu Gly His Pro Arg Leu Ala
                180                 185                 190

Ala Trp Tyr Gln Arg Val Glu Ala Val Gly Lys Asp Leu Phe Arg
            195                 200                 205

Glu Ala His Glu Val Ile Leu Lys Val Lys Asp Cys Pro Pro Ala Asp
210                 215                 220
```

Leu Ile Ile Lys Gln Lys Leu Met Pro Arg Val Leu Ala Met Ile Gln
225                 230                 235                 240

<210> SEQ ID NO 39
<211> LENGTH: 244
<212> TYPE: PRT
<213> ORGANISM: Mus musculus

<400> SEQUENCE: 39

Met Gly Leu Glu Leu Tyr Leu Asp Leu Leu Ser Gln Pro Ser Arg Ala
1               5                   10                  15

Val Tyr Ile Phe Ala Lys Lys Asn Gly Ile Pro Phe Gln Thr Arg Thr
            20                  25                  30

Val Asp Ile Leu Lys Gly Gln His Met Ser Glu Gln Phe Ser Gln Val
        35                  40                  45

Asn Cys Leu Asn Lys Val Pro Val Leu Lys Asp Gly Ser Phe Val Leu
50                  55                  60

Thr Glu Ser Thr Ala Ile Leu Ile Tyr Leu Ser Ser Lys Tyr Gln Val
65                  70                  75                  80

Ala Asp His Trp Tyr Pro Ala Asp Leu Gln Ala Arg Ala Gln Val His
                85                  90                  95

Glu Tyr Leu Gly Trp His Ala Asp Asn Ile Arg Gly Thr Phe Gly Val
            100                 105                 110

Leu Leu Trp Thr Lys Val Leu Gly Pro Leu Ile Gly Val Gln Val Pro
        115                 120                 125

Gln Glu Lys Val Glu Arg Asn Arg Asp Arg Met Val Leu Val Leu Gln
130                 135                 140

Gln Leu Glu Asp Lys Phe Leu Arg Asp Arg Ala Phe Leu Val Gly Gln
145                 150                 155                 160

Gln Val Thr Leu Ala Asp Leu Met Ser Leu Glu Glu Leu Met Gln Pro
                165                 170                 175

Val Ala Leu Gly Tyr Asn Leu Phe Glu Gly Arg Pro Gln Leu Thr Ala
            180                 185                 190

Trp Arg Glu Arg Val Glu Ala Phe Leu Gly Ala Glu Leu Cys Gln Glu
        195                 200                 205

Ala His Ser Thr Ile Leu Ser Ile Leu Gly Gln Ala Ala Lys Lys Met
210                 215                 220

Leu Pro Val Pro Pro Glu Val His Ala Ser Met Gln Leu Arg Ile
225                 230                 235                 240

Ala Arg Ile Pro

<210> SEQ ID NO 40
<211> LENGTH: 240
<212> TYPE: PRT
<213> ORGANISM: Rattus norvegicus

<400> SEQUENCE: 40

Met Val Leu Glu Leu Tyr Leu Asp Leu Leu Ser Gln Pro Cys Arg Ala
1               5                   10                  15

Ile Tyr Ile Phe Ala Lys Lys Asn Asn Ile Pro Phe Gln Met His Thr
            20                  25                  30

Val Glu Leu Arg Lys Gly Glu His Leu Ser Asp Ala Phe Ala Gln Val
        35                  40                  45

Asn Pro Met Lys Lys Val Pro Ala Met Lys Asp Gly Gly Phe Thr Leu
50                  55                  60

Cys Glu Ser Val Ala Ile Leu Leu Tyr Leu Ala His Lys Tyr Lys Val

```
                65                  70                  75                  80
Pro Asp His Trp Tyr Pro Gln Asp Leu Gln Ala Arg Ala Arg Val Asp
                    85                  90                  95

Glu Tyr Leu Ala Trp Gln His Thr Thr Leu Arg Arg Ser Cys Leu Arg
                100                 105                 110

Thr Leu Trp His Lys Val Met Phe Pro Val Phe Leu Gly Glu Gln Ile
                115                 120                 125

Arg Pro Glu Met Leu Ala Ala Thr Leu Ala Asp Leu Asp Val Asn Val
130                 135                 140

Gln Val Leu Glu Asp Gln Phe Leu Gln Asp Lys Asp Phe Leu Val Gly
145                 150                 155                 160

Pro His Ile Ser Leu Ala Asp Val Val Ala Ile Thr Glu Leu Met His
                165                 170                 175

Pro Val Gly Gly Gly Cys Pro Val Phe Glu Gly Arg Pro Arg Leu Ala
                180                 185                 190

Ala Trp Tyr Arg Arg Val Glu Ala Val Gly Lys Asp Leu Phe Leu
                195                 200                 205

Glu Ala His Glu Val Ile Leu Lys Val Arg Asp Cys Pro Pro Ala Asp
                210                 215                 220

Pro Val Ile Lys Gln Lys Leu Met Pro Arg Val Leu Thr Met Ile Gln
225                 230                 235                 240

<210> SEQ ID NO 41
<211> LENGTH: 261
<212> TYPE: PRT
<213> ORGANISM: Gallus gallus

<400> SEQUENCE: 41

Met Gly Leu Glu Leu Tyr Leu Asp Leu Leu Ser Gln Pro Cys Arg Ser
1               5                   10                  15

Ile Tyr Ile Phe Ala Arg Thr Asn Asn Ile Pro Phe Glu Phe Lys His
                20                  25                  30

Val Glu Leu Phe Lys Asp Ser Val Leu Gly Lys Lys Pro Ala Ala Ala
                35                  40                  45

Ser Gly Ala Glu Arg Pro Arg Thr Gly Pro Ser Asn Ser Glu Gly Asp
        50                  55                  60

Gly Lys Ile Ser Leu Leu Lys Lys Val Pro Val Leu Lys Asp Gly Asp
65                  70                  75                  80

Phe Thr Leu Ala Glu Cys Thr Ala Ile Leu Leu Tyr Leu Ser Arg Lys
                85                  90                  95

Tyr Asn Thr Pro Asp His Trp Tyr Pro Ser Asp Ile Lys Lys Arg Ala
                100                 105                 110

Gln Val Asp Glu Tyr Leu Ser Trp His His Ala Asn Ile Arg Ala Asn
                115                 120                 125

Ala Pro Lys Thr Met Trp Ile Lys Val Leu Ile Pro Leu Phe Thr Gly
130                 135                 140

Gln Pro Gln Pro Ser Glu Lys Leu Gln Glu Val Met Glu Gly Leu Ser
145                 150                 155                 160

Thr Ser Leu Lys Gln Phe Glu Glu Arg Phe Leu Gln Asp Lys Ala Phe
                165                 170                 175

Ile Ile Gly Ser Glu Ile Ser Leu Ala Asp Leu Val Ala Ile Val Glu
                180                 185                 190

Leu Met Gln Pro Val Gly Val Gly Cys Asp Ile Phe Glu Asp Arg Pro
                195                 200                 205
```

-continued

```
Arg Leu Met Glu Trp Arg Arg Val Glu Glu Val Gly Lys Glu
    210             215             220
Leu Phe Phe Gln Ala His Glu Met Ile Leu Asn Ile Lys Glu Leu Ser
225                 230                 235                 240
Asn Ile Gln Ile Asp Pro Gln Leu Lys Glu His Leu Ala Pro Val Leu
            245                 250                 255
Met Lys Met Leu Lys
            260

<210> SEQ ID NO 42
<211> LENGTH: 244
<212> TYPE: PRT
<213> ORGANISM: Homo sapiens

<400> SEQUENCE: 42

Met Gly Leu Glu Leu Phe Leu Asp Leu Val Ser Gln Pro Ser Arg Ala
1               5                   10                  15
Val Tyr Ile Phe Ala Lys Lys Asn Gly Ile Pro Leu Glu Leu Arg Thr
            20                  25                  30
Val Asp Leu Val Lys Gly Gln His Lys Ser Lys Glu Phe Leu Gln Ile
        35                  40                  45
Asn Ser Leu Gly Lys Leu Pro Thr Leu Lys Asp Gly Asp Phe Ile Leu
    50                  55                  60
Thr Glu Ser Ser Ala Ile Leu Ile Tyr Leu Ser Cys Lys Tyr Gln Thr
65                  70                  75                  80
Pro Asp His Trp Tyr Pro Ser Asp Leu Gln Ala Arg Ala Arg Val His
                85                  90                  95
Glu Tyr Leu Gly Trp His Ala Asp Cys Ile Arg Gly Thr Phe Gly Ile
            100                 105                 110
Pro Leu Trp Val Gln Val Leu Gly Pro Leu Ile Gly Val Gln Val Pro
        115                 120                 125
Lys Glu Lys Val Glu Arg Asn Arg Thr Ala Met Asp Gln Ala Leu Gln
    130                 135                 140
Trp Leu Glu Asp Lys Phe Leu Gly Asp Arg Pro Phe Leu Ala Gly Gln
145                 150                 155                 160
Gln Val Thr Leu Ala Asp Leu Met Ala Leu Glu Glu Leu Met Gln Pro
                165                 170                 175
Val Ala Leu Gly Tyr Glu Leu Phe Glu Gly Arg Pro Arg Leu Ala Ala
            180                 185                 190
Trp Arg Gly Arg Val Glu Ala Phe Leu Gly Ala Glu Leu Cys Gln Glu
        195                 200                 205
Ala His Ser Ile Ile Leu Ser Ile Leu Glu Gln Ala Ala Lys Lys Thr
    210                 215                 220
Leu Pro Thr Pro Ser Pro Glu Ala Tyr Gln Ala Met Leu Leu Arg Ile
225                 230                 235                 240
Ala Arg Ile Pro

<210> SEQ ID NO 43
<211> LENGTH: 211
<212> TYPE: PRT
<213> ORGANISM: Plasmodium falciparum

<400> SEQUENCE: 43

Met Gly Asp Asn Ile Val Leu Tyr Tyr Phe Asp Ala Arg Gly Lys Ala
1               5                   10                  15
Glu Leu Ile Arg Leu Ile Phe Ala Tyr Leu Gly Ile Glu Tyr Thr Asp
```

```
            20                  25                  30
Lys Arg Phe Gly Val Asn Gly Asp Ala Phe Val Glu Phe Lys Asn Phe
         35                  40                  45

Lys Lys Glu Lys Asp Thr Pro Phe Glu Gln Val Pro Ile Leu Gln Ile
 50                  55                  60

Gly Asp Leu Ile Leu Ala Gln Ser Gln Ala Ile Val Arg Tyr Leu Ser
 65                  70                  75                  80

Lys Lys Tyr Asn Ile Cys Gly Glu Ser Glu Leu Asn Glu Phe Tyr Ala
                 85                  90                  95

Asp Met Ile Phe Cys Gly Val Gln Asp Ile His Tyr Lys Phe Asn Asn
             100                 105                 110

Thr Asn Leu Phe Lys Gln Asn Glu Thr Thr Phe Leu Asn Glu Asp Leu
         115                 120                 125

Pro Lys Trp Ser Gly Tyr Phe Glu Lys Leu Leu Lys Lys Asn His Thr
     130                 135                 140

Asn Asn Asn Asn Asp Lys Tyr Tyr Phe Val Gly Asn Asn Leu Thr Tyr
145                 150                 155                 160

Ala Asp Leu Ala Val Phe Asn Leu Tyr Asp Asp Ile Glu Thr Lys Tyr
                 165                 170                 175

Pro Ser Ser Leu Lys Asn Phe Pro Leu Leu Lys Ala His Asn Glu Phe
             180                 185                 190

Ile Ser Asn Leu Pro Asn Ile Lys Asn Tyr Ile Thr Asn Arg Lys Glu
         195                 200                 205

Ser Val Tyr
     210

<210> SEQ ID NO 44
<211> LENGTH: 225
<212> TYPE: PRT
<213> ORGANISM: Oncocherca volvulus

<400> SEQUENCE: 44

Ala Ser Ser Asn Ala Asn Gln Ala Ile Thr Ser Glu Asn Ser Ile Lys
 1               5                  10                  15

Pro Lys Gly Lys Leu Gln Pro Gln Met Glu Lys Tyr Thr Leu Thr Tyr
             20                  25                  30

Phe Asn Gly Arg Gly Arg Ala Glu Val Ile Arg Leu Leu Phe Ala Leu
         35                  40                  45

Ala Asn Val Ser Tyr Glu Asp Asn Arg Ile Thr Arg Asp Glu Trp Lys
 50                  55                  60

Tyr Leu Lys Pro Arg Thr Pro Phe Gly His Val Pro Met Leu Asn Val
 65                  70                  75                  80

Ser Gly Asn Val Leu Gly Glu Ser His Ala Ile Glu Leu Leu Leu Gly
                 85                  90                  95

Gly Arg Phe Gly Leu Leu Gly Thr Asn Asp Trp Glu Glu Ala Lys Ile
             100                 105                 110

Met Ala Val Val Leu Asn Ile Asp Glu Leu Phe Gln Lys Leu Ile Pro
         115                 120                 125

Trp Thr His Glu Lys Asn Thr Thr Lys Lys Ala Glu Leu Phe Arg Asn
     130                 135                 140

Leu Ser Glu Ser Asp Val Met Pro Phe Leu Gly Arg Tyr Glu Lys Phe
145                 150                 155                 160

Leu Lys Glu Ser Thr Thr Gly His Ile Val Gly Asn Lys Val Ser Val
                 165                 170                 175
```

Ala Asp Leu Thr Val Phe Asn Met Leu Met Thr Leu Asp Asp Glu Val
            180                 185                 190

Lys Leu Glu Glu Tyr Pro Gln Leu Ala Ser Phe Val Asn Lys Ile Gly
        195                 200                 205

Gln Met Pro Gly Ile Lys Glu Trp Ile Lys Lys Arg Pro Lys Thr Tyr
    210                 215                 220

Phe
225

<210> SEQ ID NO 45
<211> LENGTH: 221
<212> TYPE: PRT
<213> ORGANISM: Drosophila melanogaster

<400> SEQUENCE: 45

Gly Gly Val Ile Ala Thr Gln Met Thr Tyr Lys Val Tyr Met Ser Gly
1               5                   10                  15

Thr Val Asn Gly His Tyr Phe Glu Val Glu Gly Asp Gly Lys Gly Arg
            20                  25                  30

Pro Tyr Glu Gly Glu Gln Thr Val Lys Leu Thr Val Thr Lys Gly Gly
        35                  40                  45

Pro Leu Pro Phe Ala Trp Asp Ile Leu Ser Pro Gln Cys Gln Tyr Gly
    50                  55                  60

Ser Ile Pro Phe Thr Lys Tyr Pro Glu Asp Ile Pro Asp Tyr Val Lys
65                  70                  75                  80

Gln Ser Phe Pro Glu Gly Phe Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Thr Tyr His Val Lys Phe Ser Gly Leu Asn Phe Pro Pro Asn
        115                 120                 125

Gly Pro Val Met Gln Lys Lys Thr Gln Gly Trp Glu Pro His Ser Glu
    130                 135                 140

Arg Leu Phe Ala Arg Gly Gly Met Leu Ile Gly Asn Asn Phe Met Ala
145                 150                 155                 160

Leu Lys Leu Glu Gly Gly Gly His Tyr Leu Cys Glu Phe Lys Thr Thr
                165                 170                 175

Tyr Lys Ala Lys Lys Pro Val Lys Met Pro Gly Tyr His Tyr Val Asp
            180                 185                 190

Arg Lys Leu Asp Val Thr Asn His Asn Lys Asp Tyr Thr Ser Val Glu
        195                 200                 205

Gln Cys Glu Ile Ser Ile Ala Arg Lys Pro Val Val Ala
    210                 215                 220

<210> SEQ ID NO 46
<211> LENGTH: 222
<212> TYPE: PRT
<213> ORGANISM: Homo sapiens

<400> SEQUENCE: 46

Met Ala Glu Lys Pro Lys Leu His Tyr Phe Asn Ala Arg Gly Arg Met
1               5                   10                  15

Glu Ser Thr Arg Trp Leu Leu Ala Ala Ala Gly Val Glu Phe Glu Glu
            20                  25                  30

Lys Phe Ile Lys Ser Ala Glu Asp Leu Asp Lys Leu Arg Asn Asp Gly
        35                  40                  45

```
Tyr Leu Met Phe Gln Gln Val Pro Met Val Glu Ile Asp Gly Met Lys
 50                  55                  60

Leu Val Gln Thr Arg Ala Ile Leu Asn Tyr Ile Ala Ser Lys Tyr Asn
 65                  70                  75                  80

Leu Tyr Gly Lys Asp Ile Lys Glu Arg Ala Leu Ile Asp Met Tyr Ile
                 85                  90                  95

Glu Gly Ile Ala Asp Leu Gly Glu Met Ile Leu Leu Pro Val Cys
                100                 105                 110

Pro Pro Glu Glu Lys Asp Ala Lys Leu Ala Leu Ile Lys Glu Lys Ile
                115                 120                 125

Lys Asn Arg Tyr Phe Pro Ala Phe Glu Lys Val Leu Lys Ser His Gly
        130                 135                 140

Gln Asp Tyr Leu Val Gly Asn Lys Leu Ser Arg Ala Asp Ile His Leu
145                 150                 155                 160

Val Glu Leu Leu Tyr Tyr Val Glu Glu Leu Asp Ser Ser Leu Ile Ser
                165                 170                 175

Ser Phe Pro Leu Leu Lys Ala Leu Lys Thr Arg Ile Ser Asn Leu Pro
                180                 185                 190

Thr Val Lys Lys Phe Leu Gln Pro Gly Ser Pro Arg Lys Pro Pro Met
                195                 200                 205

Asp Glu Lys Ser Leu Glu Glu Ala Arg Lys Ile Phe Arg Phe
                210                 215                 220

<210> SEQ ID NO 47
<211> LENGTH: 217
<212> TYPE: PRT
<213> ORGANISM: Homo sapiens

<400> SEQUENCE: 47

Pro Met Ile Leu Gly Tyr Trp Asp Ile Arg Gly Leu Ala His Ala Ile
 1               5                  10                  15

Arg Leu Leu Leu Glu Tyr Thr Asp Ser Ser Tyr Glu Glu Lys Lys Tyr
                 20                  25                  30

Thr Met Gly Asp Ala Pro Asp Tyr Asp Arg Ser Gln Trp Leu Asn Glu
             35                  40                  45

Lys Phe Lys Leu Gly Leu Asp Phe Pro Asn Leu Pro Tyr Leu Ile Asp
 50                  55                  60

Gly Ala His Lys Ile Thr Gln Ser Asn Ala Ile Leu Cys Tyr Ile Ala
 65                  70                  75                  80

Arg Lys His Asn Leu Cys Gly Glu Thr Glu Glu Lys Ile Arg Val
                 85                  90                  95

Asp Ile Leu Glu Asn Gln Thr Met Asp Asn His Met Gln Leu Gly Met
                100                 105                 110

Ile Cys Tyr Asn Pro Glu Phe Glu Lys Leu Lys Pro Lys Tyr Leu Glu
        115                 120                 125

Glu Leu Pro Glu Lys Leu Lys Leu Tyr Ser Glu Phe Leu Gly Lys Arg
        130                 135                 140

Pro Trp Phe Ala Gly Asn Lys Ile Thr Phe Val Asp Phe Leu Val Tyr
145                 150                 155                 160

Asp Val Leu Asp Leu His Arg Ile Phe Glu Pro Lys Cys Leu Asp Ala
                165                 170                 175

Phe Pro Asn Leu Lys Asp Phe Ile Ser Arg Phe Glu Gly Leu Glu Lys
                180                 185                 190

Ile Ser Ala Tyr Met Lys Ser Ser Arg Phe Leu Pro Arg Pro Val Phe
                195                 200                 205
```

```
Ser Lys Met Ala Val Trp Gly Asn Lys
    210                 215
```

<210> SEQ ID NO 48
<211> LENGTH: 209
<212> TYPE: PRT
<213> ORGANISM: Homo sapiens

<400> SEQUENCE: 48

```
Pro Pro Tyr Thr Val Val Tyr Phe Pro Val Arg Gly Arg Cys Ala Ala
1               5                   10                  15

Leu Arg Met Leu Leu Ala Asp Gln Gly Gln Ser Trp Lys Glu Glu Val
            20                  25                  30

Val Thr Val Glu Thr Trp Gln Glu Gly Ser Leu Lys Ala Ser Cys Leu
        35                  40                  45

Tyr Gly Gln Leu Pro Lys Phe Gln Asp Gly Asp Leu Thr Leu Tyr Gln
    50                  55                  60

Ser Asn Thr Ile Leu Arg His Leu Gly Arg Thr Leu Gly Leu Tyr Gly
65                  70                  75                  80

Lys Asp Gln Gln Glu Ala Ala Leu Val Asp Met Val Asn Asp Gly Val
                85                  90                  95

Glu Asp Leu Arg Cys Lys Tyr Ile Ser Leu Ile Tyr Thr Asn Tyr Glu
            100                 105                 110

Ala Gly Lys Asp Asp Tyr Val Lys Ala Leu Pro Gly Gln Leu Lys Pro
        115                 120                 125

Phe Glu Thr Leu Leu Ser Gln Asn Gln Gly Gly Lys Thr Phe Ile Val
    130                 135                 140

Gly Asp Gln Ile Ser Phe Ala Asp Tyr Asn Leu Leu Asp Leu Leu
145                 150                 155                 160

Ile His Glu Val Leu Ala Pro Gly Cys Leu Asp Ala Phe Pro Leu Leu
                165                 170                 175

Ser Ala Tyr Val Gly Arg Leu Ser Ala Arg Pro Lys Leu Lys Ala Phe
            180                 185                 190

Leu Ala Ser Pro Glu Tyr Val Asn Leu Pro Ile Asn Gly Asn Gly Lys
        195                 200                 205

Gln
```

<210> SEQ ID NO 49
<211> LENGTH: 24
<212> TYPE: DNA
<213> ORGANISM: Plasmodium falciparum

<400> SEQUENCE: 49
gggatgatgg acaacatagt gctg     24

<210> SEQ ID NO 50
<211> LENGTH: 21
<212> TYPE: DNA
<213> ORGANISM: Plasmodium falciparum

<400> SEQUENCE: 50
cccgaatatc ttgtacacca c     21

<210> SEQ ID NO 51
<211> LENGTH: 27
<212> TYPE: DNA
<213> ORGANISM: Plasmodium falciparum

```
<400> SEQUENCE: 51
cccggtgatg catttgcaga atttaac                                    27

<210> SEQ ID NO 52
<211> LENGTH: 30
<212> TYPE: DNA
<213> ORGANISM: Plasmodium falciparum

<400> SEQUENCE: 52
cccttaatag acgctttctt ttctattagc                                 30

<210> SEQ ID NO 53
<211> LENGTH: 24
<212> TYPE: DNA
<213> ORGANISM: Plasmodium falciparum

<400> SEQUENCE: 53 cccccttaata gacgctttct tttc                                      24

<210> SEQ ID NO 54
<211> LENGTH: 21
<212> TYPE: DNA
<213> ORGANISM: Plasmodium yoelii

<400> SEQUENCE: 54
atcttttctc tttgccttgt t                                          21

<210> SEQ ID NO 55
<211> LENGTH: 21
<212> TYPE: DNA
<213> ORGANISM: Plasmodium yoelii

<400> SEQUENCE: 55
gcgtcttccc ttttcagtat t                                          21

<210> SEQ ID NO 56
<211> LENGTH: 30
<212> TYPE: DNA
<213> ORGANISM: Plasmodium falciparum

<400> SEQUENCE: 56
acatagtgct gtattatttt gacgcaagag                                 30

<210> SEQ ID NO 57
<211> LENGTH: 24
<212> TYPE: DNA
<213> ORGANISM: Plasmodium falciparum

<400> SEQUENCE: 57
caaatgcatc accatttact ccaa                                       24

<210> SEQ ID NO 58
<211> LENGTH: 19
<212> TYPE: DNA
<213> ORGANISM: Plasmodium falciparum

<400> SEQUENCE: 58
gaatcttggc tccgcctcg                                             19

<210> SEQ ID NO 59
<211> LENGTH: 31
<212> TYPE: DNA
<213> ORGANISM: Plasmodium falciparum
```

```
<400> SEQUENCE: 59
gggctctcaa agggtctgta attaaaagaa c                              31

<210> SEQ ID NO 60
<211> LENGTH: 27
<212> TYPE: DNA
<213> ORGANISM: Plasmodium falciparum

<400> SEQUENCE: 60
cgggatccat gcataaaccg gtgtgtc                                   27

<210> SEQ ID NO 61
<211> LENGTH: 26
<212> TYPE: DNA
<213> ORGANISM: Plasmodium falciparum

<400> SEQUENCE: 61
cgggatccaa gcttctgtat ttccgc                                    26

<210> SEQ ID NO 62
<211> LENGTH: 46
<212> TYPE: DNA
<213> ORGANISM: Plasmodium falciparum

<400> SEQUENCE: 62
gggggtacca gatctgctat acttaaaatg atggacaaca tagtgc              46

<210> SEQ ID NO 63
<211> LENGTH: 46
<212> TYPE: DNA
<213> ORGANISM: Plasmodium falciparum

<400> SEQUENCE: 63
gggaggccta agcttcaaaa taacctgacc atttaggtaa ttcttc              46

<210> SEQ ID NO 64
<211> LENGTH: 46
<212> TYPE: DNA
<213> ORGANISM: Plasmodium falciparum

<400> SEQUENCE: 64
gggggtaccg gatccgggga tactataaca tatgcagatt tagcag              46

<210> SEQ ID NO 65
<211> LENGTH: 49
<212> TYPE: DNA
<213> ORGANISM: Plasmodium falciparum

<400> SEQUENCE: 65
ggggatatct ctagagcaca tattatatat gtatgtatat acaatgctc           49

<210> SEQ ID NO 66
<211> LENGTH: 40
<212> TYPE: DNA
<213> ORGANISM: Plasmodium falciparum

<400> SEQUENCE: 66
gggggtaccc ttagttaatc tgaaagtata tgttaataac                     40

<210> SEQ ID NO 67
<211> LENGTH: 38
<212> TYPE: DNA
```

<213> ORGANISM: Plasmodium falciparum

<400> SEQUENCE: 67
gggaagcttg cggaaataaa attacataac acacaatg					38

<210> SEQ ID NO 68
<211> LENGTH: 39
<212> TYPE: DNA
<213> ORGANISM: Plasmodium falciparum

<400> SEQUENCE: 68
gggggatcct agcaaaatag tatagtatta ttctgtttg					39

<210> SEQ ID NO 69
<211> LENGTH: 38
<212> TYPE: DNA
<213> ORGANISM: Plasmodium falciparum

<400> SEQUENCE: 69
gggtctagat cataatgaca cacattcaaa aataaggc					38

<210> SEQ ID NO 70
<211> LENGTH: 38
<212> TYPE: DNA
<213> ORGANISM: Plasmodium falciparum

<400> SEQUENCE: 70
gggggtaccg ttaatctgaa agtatatgtt aataacag					38

<210> SEQ ID NO 71
<211> LENGTH: 36
<212> TYPE: DNA
<213> ORGANISM: Plasmodium falciparum

<400> SEQUENCE: 71
gggaagcttc tttataaata tggcaaagaa attgac					36

<210> SEQ ID NO 72
<211> LENGTH: 36
<212> TYPE: DNA
<213> ORGANISM: Plasmodium falciparum

<400> SEQUENCE: 72
gggggatccc tgctatttac tgactgtttg taattc					36

<210> SEQ ID NO 73
<211> LENGTH: 36
<212> TYPE: DNA
<213> ORGANISM: Plasmodium falciparum

<400> SEQUENCE: 73
gggtctagac actattttca ttgttaacac atttgc					36

<210> SEQ ID NO 74
<211> LENGTH: 28
<212> TYPE: DNA
<213> ORGANISM: Plasmodium falciparum

<400> SEQUENCE: 74
ccgcgggtta ccattaccca gagttcac					28

<210> SEQ ID NO 75
<211> LENGTH: 25

```
<212> TYPE: DNA
<213> ORGANISM: Plasmodium falciparum

<400> SEQUENCE: 75
ctgcagcagc actatgttgt ccatc                                        25

<210> SEQ ID NO 76
<211> LENGTH: 28
<212> TYPE: DNA
<213> ORGANISM: Plasmodium falciparum

<400> SEQUENCE: 76
gatatcccat tattaaaagc ccatactg                                     28

<210> SEQ ID NO 77
<211> LENGTH: 28
<212> TYPE: DNA
<213> ORGANISM: Plasmodium falciparum

<400> SEQUENCE: 77
gaattcgtgt gcgcagatat gtataagc                                     28

<210> SEQ ID NO 78
<211> LENGTH: 34
<212> TYPE: DNA
<213> ORGANISM: Plasmodium falciparum

<400> SEQUENCE: 78
ccgcggccca cgttatttaa tagttttagt tacc                              34

<210> SEQ ID NO 79
<211> LENGTH: 31
<212> TYPE: DNA
<213> ORGANISM: Plasmodium falciparum

<400> SEQUENCE: 79
ctgcaggcac tatgttgtcc atcatttta g                                  31

<210> SEQ ID NO 80
<211> LENGTH: 36
<212> TYPE: DNA
<213> ORGANISM: Plasmodium falciparum

<400> SEQUENCE: 80
gatatccatt atattgctaa tagaaaagaa agcgtc                            36

<210> SEQ ID NO 81
<211> LENGTH: 32
<212> TYPE: DNA
<213> ORGANISM: Plasmodium falciparum

<400> SEQUENCE: 81
gaattcgttt actataaatc acttattttc tg                                32

<210> SEQ ID NO 82
<211> LENGTH: 211
<212> TYPE: PRT
<213> ORGANISM: Plasmodium falciparum

<400> SEQUENCE: 82

Met Gly Asp Asn Ile Val Leu Tyr Tyr Phe Asp Ala Arg Gly Lys Ala
1               5                   10                  15

Glu Leu Ile Arg Leu Ile Phe Ala Tyr Leu Gly Ile Glu Tyr Thr Asp
```

```
            20                  25                  30
Lys Arg Phe Gly Val Asn Gly Asp Ala Phe Val Glu Phe Lys Asn Phe
            35                  40                  45

Lys Lys Glu Lys Asp Thr Pro Phe Glu Gln Val Pro Ile Leu Gln Ile
 50                  55                  60

Gly Asp Leu Ile Leu Ala Gln Ser Gln Ala Ile Val Arg Tyr Leu Ser
 65                  70                  75                  80

Lys Lys Tyr Asn Ile Cys Gly Glu Ser Glu Leu Asn Glu Phe Tyr Ala
                 85                  90                  95

Asp Met Ile Phe Cys Gly Val Gln Asp Ile His Tyr Lys Phe Asn Asn
            100                 105                 110

Thr Asn Leu Phe Lys Gln Asn Glu Thr Thr Phe Leu Asn Glu Asp Leu
            115                 120                 125

Pro Lys Trp Ser Gly Tyr Phe Glu Lys Leu Leu Lys Lys Asn His Thr
        130                 135                 140

Asn Asn Asn Asn Asp Lys Tyr Tyr Phe Val Gly Asn Asn Leu Thr Tyr
145                 150                 155                 160

Ala Asp Leu Ala Val Phe Asn Leu Tyr Asp Asp Ile Glu Thr Lys Tyr
                165                 170                 175

Pro Ser Ser Leu Lys Asn Phe Pro Leu Leu Lys Ala His Asn Glu Phe
            180                 185                 190

Ile Ser Asn Leu Pro Asn Ile Lys Asn Tyr Ile Thr Asn Arg Lys Glu
            195                 200                 205

Ser Val Tyr
        210

<210> SEQ ID NO 83
<211> LENGTH: 205
<212> TYPE: PRT
<213> ORGANISM: Plasmodium vivax

<400> SEQUENCE: 83

Met Ala Glu Glu Ile Val Leu Tyr Tyr Phe Asp Ala Arg Gly Lys Ala
  1               5                  10                  15

Glu Leu Ile Arg Leu Ile Phe Ala Tyr Leu Gly Ile Gln Tyr Thr Asp
             20                  25                  30

Lys Arg Phe Gly Glu Asn Gly Asp Ala Phe Ile Glu Phe Lys Asn Phe
            35                  40                  45

Lys Lys Glu Lys Glu Thr Pro Phe Asn Gln Val Pro Ile Leu Glu Met
 50                  55                  60

Asp Asn Ile Ile Phe Ala Gln Ser Gln Ala Ile Val Arg Tyr Leu Ser
 65                  70                  75                  80

Lys Lys Tyr Lys Ile Ser Gly Asn Ser Glu Leu Asn Glu Phe Tyr Ala
                 85                  90                  95

Asp Met Ile Phe Cys Gly Val Gln Asp Ile His Tyr Lys Phe Asn Asn
            100                 105                 110

Thr Asn Leu Phe Lys Gln Asn Glu Thr Thr Phe Leu Asn Glu Glu Leu
            115                 120                 125

Pro Lys Trp Ser Gly Tyr Phe Glu Asn Ile Leu Lys Lys Asn Asn Cys
        130                 135                 140

Asn Tyr Phe Val Gly Asp Asp Leu Thr Tyr Ala Asp Leu Ala Val Phe
145                 150                 155                 160

Asn Leu Tyr Asp Asp Ile Glu Thr Lys Tyr Pro Asn Ser Leu Lys Asn
                165                 170                 175
```

```
Phe Pro Leu Leu Lys Ala His Asn Glu Phe Ile Ser Asn Leu Pro Asn
            180                 185                 190

Ile Lys Asn Tyr Ile Ser Asn Arg Lys Glu Ser Val Tyr
        195                 200                 205

<210> SEQ ID NO 84
<211> LENGTH: 205
<212> TYPE: PRT
<213> ORGANISM: Plasmodium knowlesi

<400> SEQUENCE: 84

Met Ala Glu Glu Ile Val Leu Tyr Tyr Phe Asp Ala Arg Gly Lys Ala
1               5                   10                  15

Glu Leu Ile Arg Leu Ile Phe Ala Tyr Leu Gly Ile Lys Tyr Thr Asp
            20                  25                  30

Lys Arg Phe Gly Glu Lys Gly Asp Ala Phe Ile Glu Phe Lys Asn Phe
        35                  40                  45

Lys Lys Glu Lys Lys Thr Pro Phe Glu Gln Val Pro Ile Leu Glu Met
    50                  55                  60

Asp Asn Ile Ile Phe Ala Gln Ser Gln Ala Ile Val Arg Tyr Leu Ser
65                  70                  75                  80

Lys Lys Tyr Lys Ile Gly Gly Asp Thr Asp Leu Asp Glu Phe Tyr Ala
                85                  90                  95

Asp Met Ile Phe Cys Gly Val Gln Asp Ile His Tyr Lys Phe Asn Asn
            100                 105                 110

Thr Asn Leu Phe Lys Gln Asn Glu Thr Thr Phe Leu Asn Glu Glu Leu
        115                 120                 125

Pro Lys Trp Ser Gly Tyr Phe Glu Asn Ile Leu Lys Lys Asn Lys Cys
    130                 135                 140

His Tyr Phe Val Gly Asp Asn Leu Thr Tyr Ala Asp Leu Ala Val Phe
145                 150                 155                 160

Asn Leu Tyr Asp Asp Ile Glu Thr Lys Tyr Pro Asn Ser Leu Lys Asn
                165                 170                 175

Phe Pro Leu Leu Lys Ala His Asn Glu Phe Ile Ser Asn Leu Pro Asn
            180                 185                 190

Ile Lys Asn Tyr Ile Ser Asn Arg Lys Glu Ser Val Tyr
        195                 200                 205

<210> SEQ ID NO 85
<211> LENGTH: 209
<212> TYPE: PRT
<213> ORGANISM: Plasmodium yoelii

<400> SEQUENCE: 85

Met Thr Tyr Leu Tyr Asn Phe Phe Phe Phe Phe Phe Phe Phe Phe Ser
1               5                   10                  15

Arg Gly Lys Ala Glu Leu Ile Arg Leu Ile Phe Ala Tyr Leu Gln Val
            20                  25                  30

Lys Tyr Thr Asp Ile Arg Phe Gly Val Asn Gly Asp Ala Phe Ala Glu
        35                  40                  45

Phe Asn Asn Phe Lys Lys Glu Lys Glu Ile Pro Phe Asn Gln Val Pro
    50                  55                  60

Ile Leu Glu Ile Gly Gly Leu Ile Leu Ala Gln Ser Gln Ala Ile Val
65                  70                  75                  80

Arg Tyr Leu Ser Lys Lys Tyr Asn Ile Ser Gly Asn Gly Glu Leu Asn
                85                  90                  95
```

| Glu | Phe | Tyr | Ala | Asp | Met | Ile | Phe | Cys | Gly | Val | Gln | Asp | Ile | His | Tyr |
|-----|-----|-----|-----|-----|-----|-----|-----|-----|-----|-----|-----|-----|-----|-----|-----|
|     |     |     |     | 100 |     |     |     | 105 |     |     |     |     | 110 |     |     |

| Lys | Phe | Asn | Asn | Thr | Asn | Leu | Phe | Lys | Gln | Asn | Glu | Thr | Thr | Phe | Leu |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Asn | Glu | Glu | Leu | Pro | Lys | Trp | Ser | Gly | Tyr | Phe | Glu | Lys | Leu | Leu | Gln |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Lys | Asn | Asn | Thr | Asn | Tyr | Phe | Val | Gly | Asp | Thr | Ile | Thr | Tyr | Ala | Asp |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Leu | Ala | Val | Phe | Asn | Leu | Tyr | Asp | Asp | Ile | Glu | Ser | Lys | Tyr | Pro | Asn |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Cys | Leu | Lys | Asn | Phe | Pro | Leu | Leu | Lys | Ala | His | Ile | Glu | Leu | Ile | Ser |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Asn | Ile | Pro | Asn | Ile | Lys | His | Tyr | Ile | Ala | Asn | Arg | Lys | Glu | Ser | Val |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

Tyr

<210> SEQ ID NO 86
<211> LENGTH: 808
<212> TYPE: DNA
<213> ORGANISM: Plasmodium berghei

<400> SEQUENCE: 86

```
atgatggaca acatagtgct gtattatttt gacgcaaggt aaaaaaaaat taataaataa     60
aataattaat ctgaaaagtt agaaataaat atatgggttt gtgattgtca atttctttgc    120
catatttata aagacacttt gtaaatacat ggatatacat acattgtgtg ttatgtaatt    180
ttatttccgc atggatatat atatatatat atatatttt ttttaagag gtaaagctga      240
actgatcaga cttattttg catatttaca agttaaatat acagatataa gatttggagt    300
aaatggtgat gcatttgcag aatttaacaa ttttaaaaaa gaaaagaaa ttccttttaa     360
tcaagttcct atattggaaa taggaggttt aatattagct caaagccaat ctatagttcg    420
atatttatca aaaaaatata atattagtgg aaatggcgaa ttaatgaat tttatgctga     480
tatgatattt tgtggtgtac aagatattca ttataaattt aataacaaa atttatttaa    540
acaaaatgaa actactttt taaatgaaga attacctaaa tggtcaggtt attttgaaaa    600
acttttacaa aaaaataata ctaattattt tgtaggggat actataacat atgcagattt    660
agcagttttt aatttatatt atgatattga atcaaaatat ccaattgtt taaaaaaatt     720
tccattatta aaagcccata ctgaacttat aagtaatatt ccaaatataa aacattatat    780
tgctaataga aaagaaagcg tctattaa                                        808
```

<210> SEQ ID NO 87
<211> LENGTH: 205
<212> TYPE: PRT
<213> ORGANISM: Plasmodium berghei

<400> SEQUENCE: 87

| Met | Met | Asp | Asn | Ile | Val | Leu | Tyr | Tyr | Phe | Asp | Ala | Arg | Gly | Lys | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Leu | Ile | Arg | Leu | Ile | Phe | Ala | Tyr | Leu | Gln | Val | Lys | Tyr | Thr | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ile | Arg | Phe | Gly | Val | Asn | Gly | Asp | Ala | Phe | Ala | Glu | Phe | Asn | Asn | Phe |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Lys | Lys | Glu | Lys | Glu | Ile | Pro | Phe | Asn | Gln | Val | Pro | Ile | Leu | Glu | Ile |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

```
Gly Gly Leu Ile Leu Ala Gln Ser Gln Ser Ile Val Arg Tyr Leu Ser
65                  70                  75                  80

Lys Lys Tyr Asn Ile Ser Gly Asn Gly Glu Leu Asn Glu Phe Tyr Ala
                85                  90                  95

Asp Met Ile Phe Cys Gly Val Gln Asp Ile His Tyr Lys Phe Asn Asn
            100                 105                 110

Thr Asn Leu Phe Lys Gln Asn Glu Thr Thr Phe Leu Asn Glu Glu Leu
        115                 120                 125

Pro Lys Trp Ser Gly Tyr Phe Glu Lys Leu Leu Gln Lys Asn Asn Thr
    130                 135                 140

Asn Tyr Phe Val Gly Asp Thr Ile Thr Tyr Ala Asp Leu Ala Val Phe
145                 150                 155                 160

Asn Leu Tyr Tyr Asp Ile Glu Ser Lys Tyr Pro Asn Cys Leu Lys Lys
                165                 170                 175

Phe Pro Leu Leu Lys Ala His Thr Glu Leu Ile Ser Asn Ile Pro Asn
            180                 185                 190

Ile Lys His Tyr Ile Ala Asn Arg Lys Glu Ser Val Tyr
        195                 200                 205

<210> SEQ ID NO 88
<211> LENGTH: 205
<212> TYPE: PRT
<213> ORGANISM: Plasmodium berghei

<400> SEQUENCE: 88

Met Met Asp Asn Ile Val Leu Tyr Tyr Phe Asp Ala Arg Gly Lys Ala
1               5                   10                  15

Glu Leu Ile Arg Leu Ile Phe Ala Tyr Leu Gln Val Lys Tyr Thr Asp
                20                  25                  30

Ile Arg Phe Gly Val Asn Gly Asp Ala Phe Ala Glu Asn Asn Phe
            35                  40                  45

Lys Lys Glu Lys Glu Ile Pro Phe Asn Gln Val Pro Ile Leu Glu Ile
        50                  55                  60

Gly Gly Leu Ile Leu Ala Gln Ser Gln Ser Ile Val Arg Tyr Leu Ser
65                  70                  75                  80

Lys Lys Tyr Asn Ile Ser Gly Asn Gly Glu Leu Asn Glu Phe Tyr Ala
                85                  90                  95

Asp Met Ile Phe Cys Gly Val Gln Asp Ile His Tyr Lys Phe Asn Asn
            100                 105                 110

Thr Asn Leu Phe Lys Gln Asn Glu Thr Thr Phe Leu Asn Glu Glu Leu
        115                 120                 125

Pro Lys Trp Ser Gly Tyr Phe Glu Lys Leu Leu Gln Lys Asn Asn Thr
    130                 135                 140

Asn Tyr Phe Val Gly Asp Thr Ile Thr Tyr Ala Asp Leu Ala Val Phe
145                 150                 155                 160

Asn Leu Tyr Tyr Asp Ile Glu Ser Lys Tyr Pro Asn Cys Leu Lys Lys
                165                 170                 175

Phe Pro Leu Leu Lys Ala His Thr Glu Leu Ile Ser Asn Ile Pro Asn
            180                 185                 190

Ile Lys His Tyr Ile Ala Asn Arg Lys Glu Ser Val Tyr
        195                 200                 205

<210> SEQ ID NO 89
<211> LENGTH: 211
<212> TYPE: PRT
<213> ORGANISM: Plasmodium falciparum
```

<400> SEQUENCE: 89

```
Met Gly Asp Asn Ile Val Leu Tyr Tyr Phe Asp Ala Arg Gly Lys Ala
1               5                   10                  15

Glu Leu Ile Arg Leu Ile Phe Ala Tyr Leu Gly Ile Glu Tyr Thr Asp
            20                  25                  30

Lys Arg Phe Gly Val Asn Gly Asp Ala Phe Val Glu Phe Lys Asn Phe
        35                  40                  45

Lys Lys Glu Lys Asp Thr Pro Phe Glu Gln Val Pro Ile Leu Gln Ile
50                  55                  60

Gly Asp Leu Ile Leu Ala Gln Ser Gln Ala Ile Val Arg Tyr Leu Ser
65                  70                  75                  80

Lys Lys Tyr Asn Ile Cys Gly Glu Ser Glu Leu Asn Glu Phe Tyr Ala
                85                  90                  95

Asp Met Ile Phe Cys Gly Val Gln Asp Ile His Tyr Lys Phe Asn Asn
            100                 105                 110

Thr Asn Leu Phe Lys Gln Asn Glu Thr Thr Phe Leu Asn Glu Asp Leu
        115                 120                 125

Pro Lys Trp Ser Gly Tyr Phe Glu Lys Leu Leu Lys Lys Asn His Thr
130                 135                 140

Asn Asn Asn Asn Asp Lys Tyr Tyr Phe Val Gly Asn Asn Leu Thr Tyr
145                 150                 155                 160

Ala Asp Leu Ala Val Phe Asn Leu Tyr Asp Asp Ile Glu Thr Lys Tyr
                165                 170                 175

Pro Ser Ser Leu Lys Asn Phe Pro Leu Leu Lys Ala His Asn Glu Phe
            180                 185                 190

Ile Ser Asn Leu Pro Asn Ile Lys Asn Tyr Ile Thr Asn Arg Lys Glu
        195                 200                 205

Ser Val Tyr
        210
```

<210> SEQ ID NO 90
<211> LENGTH: 222
<212> TYPE: PRT
<213> ORGANISM: Homo sapiens

<400> SEQUENCE: 90

```
Met Ala Glu Lys Pro Lys Leu His Tyr Phe Asn Ala Arg Gly Arg Met
1               5                   10                  15

Glu Ser Thr Arg Trp Leu Leu Ala Ala Ala Gly Val Glu Phe Glu Glu
            20                  25                  30

Lys Phe Ile Lys Ser Ala Glu Asp Leu Asp Lys Leu Arg Asn Asp Gly
        35                  40                  45

Tyr Leu Met Phe Gln Gln Val Pro Met Val Glu Ile Asp Gly Met Lys
50                  55                  60

Leu Val Gln Thr Arg Ala Ile Leu Asn Tyr Ile Ala Ser Lys Tyr Asn
65                  70                  75                  80

Leu Tyr Gly Lys Asp Ile Lys Glu Arg Ala Leu Ile Asp Met Tyr Ile
                85                  90                  95

Glu Gly Ile Ala Asp Leu Gly Glu Met Ile Leu Leu Pro Val Cys
            100                 105                 110

Pro Pro Glu Glu Lys Asp Ala Lys Leu Ala Leu Ile Lys Glu Lys Ile
        115                 120                 125

Lys Asn Arg Tyr Phe Pro Ala Phe Glu Lys Val Leu Lys Ser His Gly
130                 135                 140
```

```
Gln Asp Tyr Leu Val Gly Asn Lys Leu Ser Arg Ala Asp Ile His Leu
145                 150                 155                 160

Val Glu Leu Leu Tyr Tyr Val Glu Glu Leu Asp Ser Ser Leu Ile Ser
                165                 170                 175

Ser Phe Pro Leu Leu Lys Ala Leu Lys Thr Arg Ile Ser Asn Leu Pro
            180                 185                 190

Thr Val Lys Lys Phe Leu Gln Pro Gly Ser Pro Arg Lys Pro Pro Met
        195                 200                 205

Asp Glu Lys Ser Leu Glu Glu Ala Arg Lys Ile Phe Arg Phe
    210                 215                 220
```

INHIBITORS OF THE MALARIAL GST

GOVERNMENT INTEREST

The claimed invention was made with U.S. Government support under grant number P41 RR006009 awarded by the National Institutes of Health (NIH). The government has certain rights in this invention.

SEQUENCE LISTING

The instant application contains a Sequence Listing which has been filed electronically in ASCII format and is hereby incorporated by reference in its entirety. Said ASCII copy, created on Mar. 12, 2018, is named UPR-14236_SL.txt and is 113 Kbytes in size.

TECHNICAL FIELD

The present invention generally relates to a drug. More specifically, the present invention relates to a compound for treating malaria.

BACKGROUND OF THE INVENTION

Malaria afflicts 300-500 million people globally and 2-3 minutes die every year. More than a million children die in Africa. The problem is also serious in South East Asia followed by the Indian subcontinent and South America, where economic loss due to morbidity and loss of man-hours is high. The two major parasite species causing malaria are *Plasmodium falciparum* and *Plasmodium vivax*, although *P. ovale* and *P. malariae* are also involved, but to a minor extent. The *P. falciparum* parasite causes the most severe form of malaria and is responsible for the majority of cases resulting in death. The other three species, *P. vivax*, *P. ovale* and *P. malariae*, causes milder forms of malaria that are rarely fatal.

Prevention and proper use of treatment is very important in order to constrain malaria infections. The principles of antimalarial treatment policy rely on reducing morbidity and mortality, restricting the transmission of the malaria, reducing the parasites reservoir in the human; and avoiding the appearance and spread of drug resistance (World Malaria Report 2013). The antimalarial treatment should begin right away once the symptoms appear and the infection is confirmed. The type of treatment depends on the severity of the disease, the infecting *Plasmodium* spp., and the geographical area where the infection takes place (taking in consideration the drug resistance reported in the region). In addition, the treatment differs due to the patient's status including age, weight, other illness and pregnancy, all of these must be taken into account since they may influence treatment to be applied.

Resistance to antimalarial drug is one of the highest problem to control and eradicate malaria. According to "The World Malaria Report 2013, it is extremely important to monitor the drug resistance in order to develop treatment policy and early detection of shift patterns of resistance. Several factors contribute to the development of the drug resistance, for example poor treatment practices, inadequate patient adherence to prescribed antimalarial regimens, and the widespread availability of artemisinin-based monotherapies and substandard forms of antimalarial medicines"

Chloroquine, Sulfadoxine-Pyrimethamine, Mefloquine, Atovaquone-Proguanil, Quinine, Doxycycline and Artemisinin derivatives are drugs commonly used for treating malaria. *P. vivax* infection is treatable by antimalarial drugs, but the *P. falciparum* parasites are resistant to the first line and second line antimalarial drugs. The first line of treatment for *P. falciparum* includes artemisinin-based combination therapy (ACT) to improve the method of treatment and overcome resistance to single drug component (Kokwaro, 2009; World Malaria Report 2013). Combination therapy comprises the use of two or more antimalarials with different mechanisms of action and their objective is to eliminate the infection and prevent the development of drug resistance (Guidelines for the treatment of malaria, 2010). Currently, five ACTs are recommended by World Health Organization (WHO), these include: artemether plus lumefantrine, artesunate plus amodiaquine, artesunate plus mefloquine, artesunate plus sulfadoxine-pyrimethamine, and dihydroartemisinin plus piperaquine (Guidelines for the treatment of malaria, 2010). Severe malaria is an acute infection with high complications, signs of organ dysfunction and high level of parasitemia. Artesunate is the treatment of severe malaria infections in children and adults (Sinclair et al., 2012) followed with a complete course of ACT (Guidelines for the treatment of malaria, 2010). According to the Guidelines for the treatment of malaria 2010, two classes of antimalarial are indicated to treat severe malaria including: the cinchona alkaloids (quinine and quinidine) and the artemisinin derivatives (artesunate, artemether and artemotil). Recently, ART resistance was reported in Thailand (Phyo et al., 2012) and in Northern Cambodia, Vietnam, and Eastern Myanmar (Ashley et al., 2014). ART monotherapy is not recommended due to the reported recrudescence— appearance of parasites after clearance was accomplished during drug treatment—(White 1998) and the chance of selecting resistant parasites as reported in South East Asia (Noedl et al., 2008; Noedl et al., 2009; Dondorp et al., 2009). The WHO stopped the use of artemisinin-based monotherapies in order to help in restraining the resistance.

From the above, there is an urgent need to develop novel antimalarial drug that has a potential to cure the disease, prevent infection and block the transmission. Further there is need of the drug that could destroy drug resistant malaria parasites.

SUMMARY OF THE INVENTION

In an embodiment, a compound to inhibit a glutathione S-transferase (GST) enzyme activity having formula (I) is disclosed. The compound having formula (I) is an antimalarial compound that inhibits the growth of the *Plasmodium* spp parasites. The compound of the present invention inhibits the growth of a malarial parasite by 50%.

The *Plasmodium* spp. GST was characterized and classified into a sigma class of GST. A *P. berghei* gst gene was characterized and reverse genetic approaches showed that this gene is essential during blood stages. This result confirms that GST is a good target for the development of novel antimalarials and reveals the importance of this detoxification enzyme for the survival of *P. berghei* erythrocytic stages. The *P. berghei* gst gene was sequenced and partially characterized. The pbgst gene has an open reading frame of 808 nucleotides.

In an embodiment, the *P. berghei* GST is used as a drug target. The specificity of three GSK TCAMS compounds (TCMDC-134945, TCMDC-124132, and TCMDC-141151/TCMDC-141221) was tested in a GST enzymatic assay. During the study it was found that TCMDC-124132 compound presented inhibititory activity in pbGST and hGST.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

FIG. 1 shows an alignment of a *Plasmodium* spp. GST protein sequences;

FIG. 4A-4D are structural alignment of the *P. falciparum* GST with sigma GST from *O. volvulus* and alpha GST from human;

FIG. 5A-5D is a structural comparison of the GST structures from *P. falciparum* GST with a sigma GST from *O. volvulus* and an alpha GST from human;

FIG. 6A-6B is a *Plasmodium berghei* glutathione S-transferase gene structure of a coding region;

FIG. 7 is a nucleotide and predicted amino acid sequences of the *Plasmodium berghei* glutathione S-transferase;

FIG. 8A-8B is a diagrammatic representation of the coding region of the human and the rodent *Plasmodium* spp. glutathione S-transferase gene;

FIG. 10 shows a sequence alignment of the *P. berghei*, *P. falciparum* and human GST homologues;

FIG. 11A-11C is an expression analysis of the *Plasmodium berghei* glutathione S-transferase;

FIG. 12A-12E is a diagrammatic representation of a pbgst-ko construct 1 and analysis of potential integration;

FIG. 13A-13D is a diagrammatic representation of a pbgst-ko construct 2 and analysis of potential integration;

FIG. 23A-23E shows the GSK TCAMS compounds showing in vitro antimalarial activity;

FIG. 24A-24B shows a growth inhibition curves of the compounds TCMDC-132196 and TCMDC-132198;

FIG. 25A-25D shows a proposed binding mode and interaction of GSK TCAMS compounds in the G and H binding pockets of the *P. berghei* glutathione S-transferase enzyme;

FIG. 26A-26D shows the glutathione S-transferase enzymatic activity in the presence of S-hexylglutathione;

FIG. 27A-27C shows the *Plasmodium berghei* Glutathione S-transferase potential inhibitory activity of the GSK TCAMS compounds; and FIG. 28A-28B is a comparison of the effect of TCMDC-124132 compound in the Glutathione S-transferase activity of *Plasmodium berghei* and human.

DETAILED DESCRIPTION OF INVENTION

Figure 2:
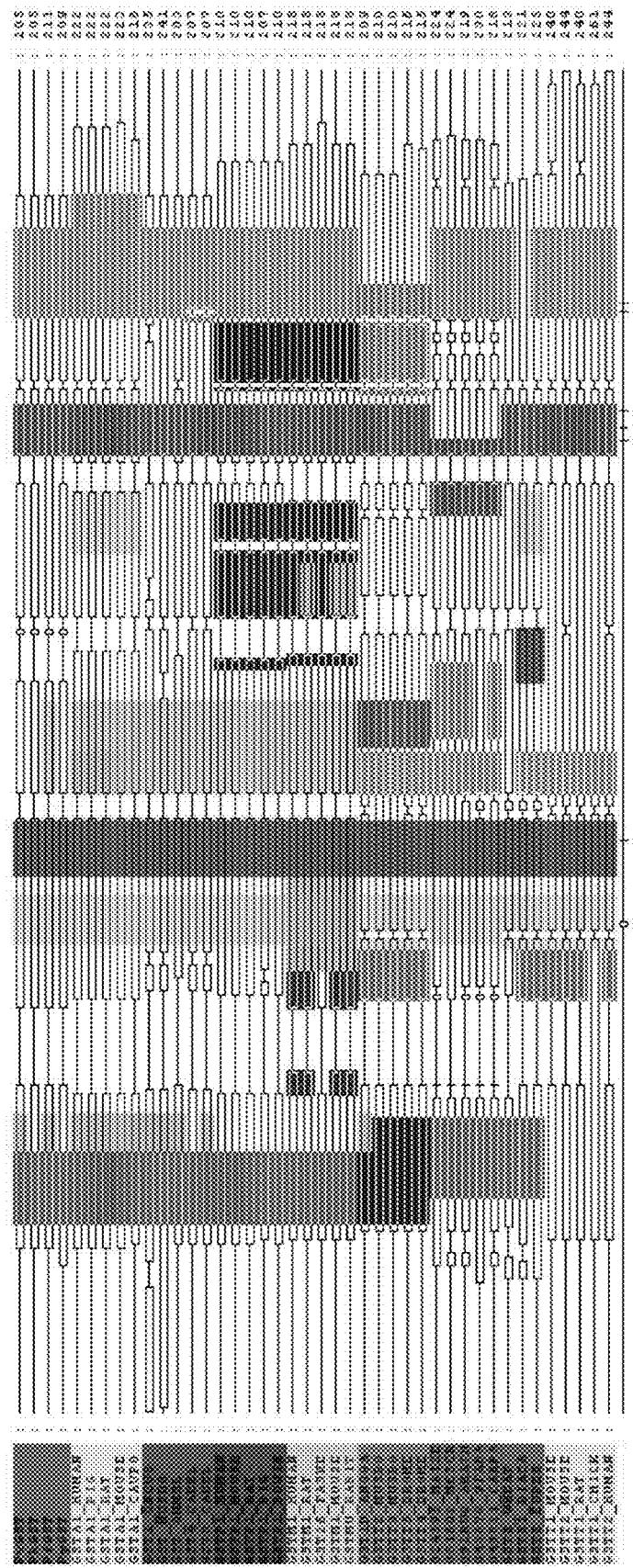
FIG. 2 is a schematic sequence alignment of the four *Plasmodium* spp.

A description of embodiments of the present invention will now be given with reference to the Figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The present invention relates to antimalarial compounds. The compound of the present invention is used to treat malaria by preventing infection and blocking the transmission of the disease. In an embodiment, several compounds were tested to compare their efficacy to inhibit Glutathione S-transferase (GST) activity. Glutathione S-transferase is a detoxification enzyme found in most organisms. The GST enzyme is involved in the cellular detoxification of endobiotic and xenobiotic compounds by conjugating to glutathione and turning them into water-soluble compounds to promoting their excretion from the cell. Glutathione S-transferase is plays a major role in development of the *Plasmodium* parasites and therefore, it is a potential drug target site. In an embodiment, the compound of the present invention were tested in cultures of mice infected with *P. berghei*.

In an embodiment, homologous sequences of *Plasmodium* spp. GST were retrieved and used for sequence analysis. The predicted sequences of *Plasmodium* spp. GSTs protein were aligned using ClustalW program with the default parameters. The GeneDoc program was used to visualize the protein alignment. The PfGST having an accession number Q8MU52 was used as the query sequence to perform the sequence similarity searches using the BLAST search tool at the iProClass database. The BLAST search was carried out using the default parameters. GSTs sequences from seven GST classes (alpha, sigma, pi, mu, delta, tau and theta) were selected. For each GST class, five sequences were selected except for the zeta class in which the three sequences were chosen. The *Plasmodium* is an eukaryotic organism, therefore sequences from mammals, plants and insects were retrieved excluding the prokaryotic GSTs. A total of 38 GST sequences (Table 1) were obtained and used to perform a multiple sequence alignment using the ClustalW program. The Multiple Entropy for Motif Elicitation (MEME) program was used to identify 20 conserved motifs using 'zero or more occurrences per sequence' pattern. The alignment and motifs were visualized using the program GeneDoc. The multiple sequence alignment was trimmed manually and then used to perform the phylogenetic analysis. The phylogenetic analysis was performed by MEGA4 (Molecular Evolutionary Genetics Analysis, Version 4) program using the neighbor-joining algorithm and a bootstrapped data set of 100 replicates. The program FigTree was used to visualize the consensus tree from the bootstrap analysis.

Molecular Dynamics (VMD). The three-dimensional (3D) structures of the alpha, sigma, pi and mu GSTs were obtained from the Protein Data Bank (PDB) and are listed in Table 2. The sigma GST from *Onchocerca volvulus* (PDB code 2HNL) and the human alpha GST (PDB code 1PKZ) were used to perform the structural alignments with PfGST (PDB code 1Q4J). The detailed structural superpositions were carried out with VMD program, specifically in the N-terminal domain (G-site), C-terminal domain (H-site), and α-helix at the C-terminus of the proteins. Close-up views of the H-site, G-site and α-helix in the C-terminus were done to facilitate the analysis of the 3D structure of the proteins. The *P. berghei* ANKA 507clone1 (ANKA-GFP) line was used for all experiments that involved wild type parasites. The ANKA-GFP line has been genetically modified to express the green fluorescent protein (GFP) under the control of the constitutive eukaryotic elongation factor 1A (eef1a) promoter and was selected by Fluorescence Activated Cell Sorter (FACS) based on GFP expression. The description of this parasite line is available at the Rodent Malaria genetically modified Parasites Database (RMg-

| SEQ ID NO: | Protein name | Organism | Family class | Accession number | Protein length (aa) |
|---|---|---|---|---|---|
| 1 | PfGST | *Plasmodium falciparum* | sigma | Q8MU52 | 211 |
| 2 | PvGST | *Plasmodium vivax* | sigma | Q0ZS46 | 205 |
| 3 | PkGST | *Plasmodium knowlesi* | sigma | B3LAI5 | 205 |
| 4 | PyG ST | *Plasmodium yoelii* | sigma | Q7REH6 | 209 |
| 5 | GSTA1_HUMAN | *Homo sapiens* | alpha | P08263 | 222 |
| 6 | GSTA1_RAT | *Rattus norvegicus* | alpha | P00502 | 222 |
| 7 | GSTA1_MOUSE | *Mus musculus* | alpha | P13745 | 223 |
| 8 | GSTA1_PIG | *Sus scrofa* | alpha | P51781 | 222 |
| 9 | GSTA1_CAVPO | *Cavia porcellus* | alpha | P81706 | 218 |
| 10 | GST1_ONCVO | *Oncocherca volvulus* | sigma | P46434 | 235 |
| 11 | GST_MUSDO | *Musca domestica* | sigma | P46437 | 241 |
| 12 | GST_OMMSL | *Ommastrephes sloanei* | sigma | P46088 | 203 |
| 13 | GST4_CAEEL | *Caenorhabditis elegans* | sigma | Q21355 | 207 |
| 14 | GST3_CAEEL | *Caenorhabditis elegans* | sigma | O16116 | 207 |
| 15 | GSTP1_HUMAN | *Homo sapiens* | pi | P09211 | 210 |
| 16 | GSTP1_MOUSE | *Mus musculus* | pi | P19157 | 210 |
| 17 | GSTP1_RAT | *Rattus norvegicus* | pi | P04906 | 210 |
| 18 | GSTP1_PIG | *Sus scrofa* | pi | P80031 | 207 |
| 19 | GSTP1_BOVIN | *Bos taurus* | pi | P28801 | 210 |
| 20 | GSTM1_HUMAN | *Homo sapiens* | mu | P09488 | 218 |
| 21 | GSTM1_RAT | *Rattus norvegicus* | mu | P04905 | 218 |
| 22 | GST26_FASHE | *Fasciola hepatica* | mu | P30112 | 218 |
| 23 | GSTM1_MOUSE | *Mus musculus* | mu | P10649 | 218 |
| 24 | GSTMU_RABIT | *Oryctolagus cuniculus* | mu | P46409 | 218 |
| 25 | GST1D_ANOGA | *Anopheles gambiae* | delta | Q93113 | 209 |
| 26 | GSTT2_MUSDO | *Musca domestica* | delta | P46431 | 210 |
| 27 | GSTT3_MUSDO | *Musca domestica* | delta | P46432 | 210 |
| 28 | GSTT5_DROME | *Drosophila melanogaster* | delta | Q9VG95 | 216 |
| 29 | GSTT4_DROME | *Drosophila melanogaster* | delta | Q9VG96 | 215 |
| 30 | O24595_MAIZE | *Zea mays* | tau | O24595 | 224 |
| 31 | O81602_MESCR | *Mesembryanthemum crystallinum* | tau | O81602 | 224 |
| 32 | Q9ZRW8_ARATH | *Arabidopsis thaliana* | tau | Q9ZRW8 | 219 |
| 33 | Q43678_9FABA | *Vigna radiate* | tau | Q43678 | 230 |
| 34 | O49821_CARPA | *Carica papaya* | tau | O49821 | 218 |
| 35 | GSTZ-WHEAT | *Triticum aestivum* | zeta | O04437 | 213 |
| 36 | GSTZ1_DIACA | *Dianthus caryophyllus* | zeta | P28342 | 221 |
| 37 | GSTZ_EUPES | *Euphorbia esula* | zeta | P57108 | 225 |
| 38 | GSTT1_MOUSE | *Mus musculus* | theta | Q64471 | 240 |
| 39 | GSTT2_MOUSE | *Mus musculus* | theta | Q61133 | 244 |
| 40 | GSTT1_RAT | *Rattus norvegicus* | theta | Q01579 | 240 |
| 41 | GSTT1_CHICK | *Gallus gallus* | theta | P20135 | 261 |
| 42 | GSTT2_HUMAN | *Homo sapiens* | theta | P30712 | 244 |

In an embodiment, the structural alignment of the *P. falciparum* GST (PDB code 1Q4J) was performed. The *P. falciparum* GST (PDB code 1Q4J) with a representative member of each of the GST classes (alpha, sigma, pi and mu) was done using the MultiSeq feature in the Visual mDB) as RMgm-7. The *P. berghei* GFP-Lucama1 (PbGFP-Lucama1, also standard as 1037c11) line, is an ANKA mutant parasite line which express GFP and the firefly luciferase (luc) gene under the control of a schizont-specific ama-1 promoter (Spaccapelo et al., 2010). The GFP-luc gene was integrated into the "phenotypically neutral" 230p genomic locus by double crossover integration. Both the parasite lines, ANKA 507cl1 and 1037cl1, were provided by the Leiden University Malaria Research Group at the Department of Parasitology, Leiden University Medical Center (LUMC), The Netherlands.

TABLE 2

Glutathione S-transferase sequences used for the structural alignments

| SEQ. ID NO | Protein name | Organism | Family class | PDB code | Protein length |
|---|---|---|---|---|---|
| 43 | PfGST | Plasmodium falciparum | sigma | 1Q4J | 211 |
| 44 | GST1_ONCVO | Oncocherca volvulus | sigma | 2HNL | 225 |
| 45 | DmGST | Drosophila melanogaster | sigma | 1MOU | 221 |
| 46 | GSTA1_HUMAN | Homo sapiens | alpha | 1PKZ | |
| 47 | GSTM1_HUMAN | Homo sapiens | mu | 1GTU | |
| 48 | GSTP1_HUMAN | Homo sapiens | pi | 10GS | |

The compounds of the present invention were tested in the mice infected by the *Plasmodium berghei*. Animal experiments were done using 4-6 weeks old Swiss-CD1 female mice from Charles River Laboratories, Wilmington, Mass., USA. The mice used for the study were maintained and housed according to NIH guidelines and were allowed to acclimatize for 1 week prior to the beginning of the studies.

*Plasmodium berghei* Infections and Maintenance:

The Cryopreserved *P. berghei* parasites were removed from liquid nitrogen, slowly thawed at room temperature, diluted in sterile phosphate buffered saline (1×PBS pH 7.4) in a ratio of 1:2. An amount of 200 µL of above preparation were intravenously (IV) injected into each of the mouse (donor mice). The parasitemia was monitored after five days of inoculation and on daily basis thereafter by microscopic examination of Diff-Quick stained thin tail blood smears. When parasitemia levels reached 5-20% the infection was passed intravenously IV to new mice. The Mice were anesthetized with a cocktail of Ketamine (150 mg/kg) and Xylazine (12 mg/kg) injected intraperitoneal (IP). The blood was collected by a cardiac puncture using a syringe containing 100 µL of 50 U/mL heparin solution. Infected blood was used to cryopreserved parasites, diluted in 1:2 ratio in 30% glycerol prior to quick freeze in liquid nitrogen. The *P. berghei* infected blood was either pooled and/or processed individually depending on further experimental procedures.

In the next step, the *P. berghei* infected blood was harvested by heart puncture from the mice with parasitemia between 5-20%. Glass beads and cellulose columns were made to remove the blood platelets and white blood cells (WBCs). The cellulose column was equilibrated with three volumes of cold 1×PBS pH 7.4 prior to loading of the infected blood. To remove the platelets, the *P. berghei* infected blood was passed through a glass bead column. The column was washed with two volumes of 1×PBS pH 7.4 and the eluted blood was further passed through a Whatman® CF 11 cellulose columns to remove the WBCs. In the next step the column was washed with three volumes of PBS and kept in buffer (never be allowed to dry). All the procedures were carried out at 4° C. temperature. Alternatively, the WBCs were removed using a Plasmodipur filter, which was equilibrated with 20 mL of the PBS prior to applying the infected blood, previously diluted in 1:2 ratio in 1×PBS maintaining the pH at 7.4. Subsequently, 10 mL of 1×PBS having the pH 7.4 was added to the filter in order to wash the remaining blood if any attached to the membrane. The eluted blood was then centrifuged at 805×g for 5 minutes at 4° C. The supernatant was removed and the pellet was washed twice with 1×PBS maintaining pH 7.4. Ethylenediaminetetraacetic acid (EDTA) and saponin was added to the infected blood to lyse the RBCs. In an embodiment, 100 µL of 0.5M EDTA and 20 µL of 15% saponin were added to the infected blood which was then incubated for 15 minutes at 37° C. The blood was centrifuged at a speed of 1,811×g for 5 minutes at 4° C. to collect the free parasites. The supernatant was removed and the parasite pellet was washed twice with 1×PBS pH 7.4 as previously described. The parasite pellets were collected and used either for extraction of nucleic acids (DNA or RNA), preparation of chromosomes or parasite proteins. The parasite pellet was stored at −80° C. for further use for example—DNA or protein extraction.

Nucleic Acids Extraction: DNA. Chromosome Blocks and RNA

Genomic DNA Extraction:

The parasite pellet obtained in the above step is used for extraction of DNA. The parasite pellets were thawed on ice and resuspended in 700 µL of TNE buffer (10 mM Tris pH 8.0, 100 mM NaCl, 5 mM EDTA pH 8.0) supplemented with 200 µg ribonuclease (RNase, 20 µL of a 10 mg/ml solution), 1% (v/v) sodium dodecyl sulfate (SDS, 100 µL of a 10% solution) and demineralized water to a final volume of 1 mL. The solution was THEN incubated for 10 minutes at a temperature 37° C., to which 200 µg of Proteinase K (20 µL of a 10 mg/ml solution) was added followed by 1 hour incubation at 37° C. The parasite genomic DNA (gDNA) was isolated from the lysate by organic extraction. The organic extraction was carried out using phenol, phenol:chloroform:isoamylalcohol in the ratio 25:24:1, and chloroform:isoamylalcohol in the ratio 24:1. The organic extraction process is carried out, by adding equal volume (500 µL) of each of the reagent to the sample. The reagent is mixed properly by inversion technique prior to the centrifugation. The centrifugation was carried out at maximum speed of (20,817×g) for 5 minutes at room temperature. After the chloroform:isoamylalcohol extraction, the aqueous upper phase was collected and the gDNA was precipitated by adding 0.1 volume of 3M Sodium acetate (NaAc, pH 5.2) and 2 volumes of 96% ethanol. The samples were stored at −20° C. (for a couple of hours to overnight) to precipitate the DNA followed by the centrifugation process for 10 minutes at maximum speed (20,817×g) at 4° C. The supernatant was removed and the pellet was washed with 70% ethanol, and further centrifuged for 5 minutes at maximum speed (20, 817×g) at 4° C. The supernatant was discarded again and the pellet was air-dried in a laminar flow hood maintaining the room temperature. The DNA pellet was resuspended in demineralized water (~300 µL, depending on the pellet size); and the DNA concentration and quality was determined by agarose gel electrophoresis and/or spectrophotometrically.

Chromosome Blocks:

The *P. berghei* parasites were collected from infected blood as previously described in the Parasite isolation section. The *P. berghei* chromosome blocks were prepared by a prior art method. The parasite pellet obtained previously was mixed with an equal volume of 1.5-2% (w/v) low melting agarose at 37° C. and transferred to a chromosome block mould. These blocks are left at room temperature to allow agarose polymerization. The chromosome blocks were incubated overnight at 37° C. in 10 mL of Sarcosyl/EDTA (SE) buffer (1% sarcosyl, 0.5M EDTA pH 8.0) supplemented with 50 µl of a 20 mg/ml Proteinase-K solution. After overnight incubation, the solution was replaced with SE buffer and the chromosome blocks were stored at 4° C. until needed.

Parasite RNA Extraction:

In an embodiment, total parasite RNA from asexual blood stages was extracted using RNA Stat-60™ (Tel-Test Inc.). Ten volumes of RNA Stat-60™ were added to one volume of the pack cell volume (PCV) of the infected blood and gently mixed by vortex until homogeneous. Samples were used or stored at −80° C. until ready for further processing. Two volumes of chloroform per volume of PCV were added, mixed by inversion for 2 minutes and then incubated for 1 minute without shaking. The samples were centrifuged at 9,400×g for 20 minutes at room temperature and the aqueous phase was recovered. The precipitation of the total RNA was done by adding 5 mL of isopropanol and then incubated at −20° C. for at least 30 minutes or overnight. Subsequently, the samples were centrifuged at 9,400×g for 15 minutes at 4° C. The RNA pellet was washed with 80% ethanol and centrifuged at 9,400×g for 15 minutes at 4° C. The RNA pellet was air-dried in a laminar flow hood at room temperature and resuspended in RNase free water.

DNA Sequencing of the *Plasmodium berghei* Glutathione S-Transferase Gene:

The *P. berghei* gDNA and cDNA from the ANKA-GFP strain was PCR amplified using primers based on the *P. falciparum* and *P. yoelii* gst genes available in GenBank, AYO14840 and XM_720396, respectively. Amplification of pbgst gene fragments was carried out using a high-fidelity polymerase (USB® FideliTaq™) with the following primers pairs.

Sequencing Inc., CA to be sequenced using the Applied Biosystems Big Dye Terminator V3.0 sequencing chemistry. The open reading frame of the pbgst gene was sequenced at least twice in each direction. A sequence assembly tool such as "The Clone Manager Professional" (Version 9.1 for Windows, Scientific & Educational Software) was used to assemble the gDNA and cDNA. The predicted amino acid sequence was obtained using the ExPASy Translate tool.

Reverse Transcriptase PCR:

In an embodiment, complementary DNA (cDNA) from total RNA (asexual mixed blood stages) was synthesized using SuperScript® II Reverse Transcriptase (Invitrogen™). The PCR reaction was carried out using specific primers for the pbgst gene; the primer set was 211/214

(SEQ ID NO: 49
(5'-GGGATGATGGACAACATAGTGCTG-3' and (SEQ ID NO: 52)
5'-CCCTTAATAGACGCTTTCTTTTCTATTAGC-3')

(Table 3). The PCR reactions were done using 2 μL of cDNA, also in the presence or absence of reverse tran-

TABLE 3

Plasmodium berghei specific primers

| SEQ ID NO | Primer Name | Nucleotide Sequence (5'-3') | Mers | Sence (S)/ Antisense (AS) | Target Gene | Restriction Site | Purpose |
| --- | --- | --- | --- | --- | --- | --- | --- |
| 49 | 211 | GGGATGATGGACAACATAGTGCTG | 24 | S | pbgst | — | pbgst sequencing |
| 50 | 212 | CCCGAATATCTTGTACACCAC | 21 | AS | pbgst | — | pbgst sequencing |
| 51 | 213 | CCCGGTGATGCATTTGCAGAATTTAAC | 27 | S | pbgst | — | pbgst sequencing |
| 52 | 214 | CCCTTAATAGACGCTTTCTTTTCTATTAGC | 30 | AS | pbgst | — | pbgst sequencing |
| 53 | 215 | CCCCTTAATAGACGCTTTCTTTTC | 24 | AS | pbgst | — | pbgst sequencing |
| 54 | hep17F | ATCTTTTCTCTTTGCCTTGTT | 21 | S | pbhep17 | — | PCR and RT-PCR control |
| 55 | hep17R | GCGTCTTCCCTTTTCAGTATT | 21 | AS | pbhep17 | — | PCR and RT-PCR control |
| 56 | 128 | ACATAGTGCTGTATTATTTTGACGCAAGAG | 30 | S | pbgst | — | RT-qPCR |
| 57 | 129 | CAAATGCATCACCATTTACTCCAA | 24 | AS | pbgst | — | RT-qPCR |
| 58 | 348 | GAATCTTGGCTCCGCCTCG | 19 | S | 18s rRNA | — | RT-qPCR |
| 59 | 349 | GGGCTCTCAAAGGGTCTGTAATTAAAAGAAC | 31 | AS | 18s rRNA | — | RT-qPCR |
| 60 | 190 | CGGGATCCATGCATAAACCGGTGTGTC | 27 | S | tgdhfrlls | — | confirm plasmid integration |
| 61 | 191 | CGGGATCCAAGCTTCTGTATTTCCGC | 26 | AS | tgd/Jfrlls | — | confirm plasmid integration |

The PCR-amplified products were gel-purified using a gel extraction kit (Promega), and ligated into the TOPO TA Cloning vector, which are transformed into *Escherichia coli* PMC 103 competent cells according to the manufacturer's instructions. The purified clones were sent to Davis scriptase to rule out gDNA contamination in the samples. The primers based on the *P. yoelii* hepatocyte erythrocyte protein 17, and directed to the two exons were designed to amplify the *P. berghei* hepatocyte erythrocyte protein 17 (pbhep 17) gene homologue in order to exclude potential gDNA contamination.

Quantitative Real-Time PCR:

The Relative expression of the pbgst transcript was determined by Quantitative Real-Time PCR (RT-qPCR). The total RNA was isolated from *P. berghei* erythrocytic stages using Tri-Reagent (MRC). The total RNA was quantified using Thermo Scientific™ NanoDrop™ 8000 Spectrophotometer. The quality and integrity of the RNA was determined by 1% agarose gel electrophoresis. The cDNA was generated from 2 μg of the parasite RNA using the SuperScript® VILO™ cDNA Synthesis Kit. RT-qPCR was done in triplicate using the StepOnePlus™ Real-Time PCR System (Applied Biosystems®) for all the assays. The reactions were done with 1 μL of cDNA sample, 600 nM of gene specific primers and 9 μL of Fast SYBR® Green PCR Master Mix (Applied Biosystems®) for a total reaction volume of 10 μL. The primers were designed to amplify 117 bp of GST and 71 bp of 18s rRNA as a housekeeping gene. The primer pairs used were (Table 3): GST (128/129)

```
        (sense)                         (SEQ ID NO: 56)
    5'-ACATAGTGCTGTATTATTTTGACGCAAGAG-3'
``` and

```
        (anti-sense)                    (SEQ ID NO: 57)
    5'-CAAATGCATCACCATTTACTCCAA-3';
``` and 18s rRNA (348/349):

```
        (sense)                         (SEQ ID NO: 58)
        5'-GAATCTTGGCTCCGCCTCG-3'
``` and

```
        (anti sense)                    (SEQ ID NO: 59)
    5'-GGGCTCTCAAAGGGTCTGTAATTAAAAGAAC-3'.
```

The PCR cycling conditions were an initial denaturation cycle at 95° C. for 20 seconds, 40 cycles of 95° C. for 3 seconds and 60° C. for 30 seconds, and melting curve of 95° C. for 15 seconds, 60° C. for 1 minute, and 95° C. for 15 seconds increasing temperature by 0.5° C. The *P. berghei* cDNA samples were at concentration of 50 ng/μL. The primer concentrations were optimized and dissociation curves were generated to verify the amplification of a single PCR product. The melting curves were analyzed to ensure specificity of the amplification. The expression data was analyzed using the StepOne™ Software v2.2 from Applied Biosystems®. The relative expression of the pbgst gene transcript was normalized to 18s rRNA A-type expression. Expression analysis was confirmed in two independent biological replicates. The RT-qPCR data was generated in collaboration with the doctoral student Vivian Padin.

Analyses of *Plasmodium berghei* Glutathione S-Transferase:

The following *Plasmodium* spp. gst gene sequences were retrieved from PlasmoDB: *P. falciparum* GST (PF3D7_1419300), *P. vivax* GST (PVX_085515), *P. knowlesi* GST (PKH_132970), *P. yoelii* GST (PY17X_1025800) and *P. chabaudi* GST (PCHAS_102470). The gst sequences from the *Plasmodium* spp. mentioned above were compared with the *P. berghei* gst sequence in order to identify differences in the architecture of the intron-exon boundaries. The predicted protein sequence of *P. berghei* GST was analyzed to identify conserved domains using the Conserved Domain Database (CDD) from the National Center for Biotechnology Information (NCBI). Protein expression data of the life cycle of the *P. berghei* ANKA parasite line are available at PlasmoDB. A search into the expression data was performed using the *P. berghei* gst gene (PBANKA_102390) in order to obtain protein expression evidence of this gene across the different life cycle stages.

The GST sequence of *P. berghei*, *P. falciparum* and human GST (PDB code 1PKZ) were used for sequence analysis. The predicted protein sequences were aligned using the ClustalW program hosted at the European Bioinformatics Institute (using the default parameters). The alignment was visualized in the GeneDoc program (provided by the Pittsburgh Supercomputing Center) and some manual editing was made to produce the final alignment.

DNA Amplification by Polymerase Chain Reaction:

The DNA amplification were done by Polymerase Chain Reactions (PCRs) technique. The Polymerase Chain Reactions (PCRs) technique were carried out in a total reaction volume of 50 μL. Either high fidelity polymerase (USB® FideliTaq™) or Taq DNA polymerase (Invitrogen) were used for amplification. In order to avoid errors, high fidelity polymerase was used to amplify the pbgst fragments used for sequencing the gene and the targeting regions to be cloned into the knockout plasmids. PCR reactions using USB® FideliTaq™ contained the following: 25 μL FideliTaq PCR Master Mix (2×), 100 ng gDNA, 20 pmol of each primer and ultrapure water up to 50 μL. PCR amplification conditions using the USB® FideliTaq™ were carried out by following method: initial denaturation at 92° C. for 2 minutes, followed by 15 cycles of 92° C. for 30 seconds, 45° C. for 30 seconds (primer annealing), extension of 62° C. for 1 minute and final extension at 62° C. for 5 minutes. Further, the Taq DNA polymerase was used to amplify short segments of DNA and for the detection of PCR products. The PCR reactions using Taq DNA polymerase contained the following: 1.25 U of Taq DNA polymerase, 50 ng gDNA, 10 pmol of each primer and 200 μM deoxynucleotide triphosphates (dNTPs). The PCR amplification cycling conditions were: initial denaturation at 92° C. for 5 minutes, followed by 30 cycles of 92° C. for 30 seconds, 45° C. for 30 seconds (primer annealing), extension of 62° C. for 30 seconds and final extension at 62° C. for 7 minutes. The annealing temperatures varied depending on the primers used. The PCR amplified products were evaluated by agarose gel electrophoresis with ethidium bromide staining and visualized using the Gel Doc™ XR System (Bio-Rad).

Protein Isolation: Enzymatic Activity and Antigen

A) Protein for Enzymatic Activity Blood was collected by heart puncture from *P. berghei* infected mice with approximately 20% parasitemia. White blood cells were removed using Plasmodipur filter (Euro-Diagnostica). The infected RBCs were washed (1×PBS pH 7.4/6 mM EDTA) and lysed with 0.15% saponin. The Parasites were resuspended in buffer (3.5 mM MgCl2, 110 mM KCl, 40 mM NaCl, 20 mM HEPES, 6 mM EDTA, pH 7.4) containing protease inhibitors (0.01 mg of leupeptin A, 0.001 mg of pepstatin A, 0.35 mg of phenylmethylsulfonyl fluoride [PMSF]). The parasite pellets were lysed by three freeze/thaw cycles (liquid nitrogen and 37° C. water bath). The supernatant was collected and used for the GST enzymatic assay. The remaining proteins were stored at −20° C. until further used. The concentration of protein in the parasite extracts was determined by Bio-Rad DC Protein Assay and bovine serum albumin (BSA) for the standard curve.

B) Protein Antigen: The infected blood from mixed asexual blood stages were obtained from infected mice as previously described (Parasite Isolation Section). The parasite pellet was stored at −80° C. until used. For protein extraction, the parasite pellet was resuspended in 0.5-1 mL of 1×PBS pH 7.4 and 6 mM EDTA pH 8.0 supplemented with an antiprotease cocktail containing 1 µg/mL pepstatin A, 2 mM PMSF, and 10 µg/mL leupeptin A. Subsequently, the parasites were lysed by three freeze and thaw cycles (liquid nitrogen and 37° C. water bath) and the parasite extracts were centrifuged at 12,000×g for 20 minutes at 10° C. The supernatant was collected and stored at −80° C. until used. The protein concentration was determined with the Bio-Rad DC Protein Assay using a BSA standard curve.

Western Blot Analysis:

The western blotting technique was performed to detect the parasitic proteins. The parasite proteins were isolated as previously described above (Parasite Isolation Section) and stored at −80° C. The protein samples were thawed on ice to avoid protease degradation. The protein extracts from *P. berghei* erythrocytic stages were electrophoresed in 12% acrylamide gels on a Bio-Rad apparatus under reducing (denatured) and non-reducing (native) conditions. The running buffer was prepared as a 10× stock as follows: 30 g Tris base, 144 g Glycine, 10 g SDS and reverse osmosis water (RO water) up to 1 L. This buffer was diluted to 1× with RO water. The gel was electrophoresed at 100 volt (V) through the stacking gel and then the voltage was increased to 200V until proteins migrate through the resolving gel. The migration was allowed to continue until the dye is near the end of the gel. After running the gel it was transferred to a polyvinyl difluoride (PVDF) membrane. The PVDF membranes were hydrated with methanol for 30 seconds and then equilibrated in transfer buffer for 30 minutes. The blot was assembled and the transfer was done using the Mini Trans-Blot® Electrophoretic Transfer Cell (Bio-Rad) at 4° C., overnight at 12V. A 25× transfer buffer was prepared as follows: 18.2 g Tris base, 90 g Glycine and Milli-Q water up to 1 L. The transfer buffer was prepared fresh for each experiment containing 40 mL of 25× transfer buffer, 200 mL methanol and completed with RO water. After transfer, the gel was verified to assure that the pre-stained ladder was transferred to the membrane. Membranes were blocked with 3% milk solution containing 1M Tris pH 7.5, 5M NaCl, 50 µL Tween 20 for two hours at room temperature with continuous shaking. To detect expression of the GST protein a rabbit polyclonal PfGST-antibody was used. The anti-PfGST was diluted 1:500 in blocking solution. The membrane was incubated at room temperature for one hour and subsequently washed three times with blocking solution. The secondary antibody (anti-rabbit IgG) was used in a dilution of 1:100,000 in blocking solution and the blot was incubated for an hour at room temperature. The secondary antibody was removed by washing the membrane with PBS. As a loading control, a monoclonal antibody (diluted 1:100) directed to *P. berghei* 75-kDa heat-shock protein was used (HSP70). The secondary antibody was an anti-mouse IgG-HRP at a dilution of 1:20,000 and incubated at room temperature for 1 hour. The SuperSignal® West Femto Kit from Pierce, Thermo Scientific was used for detection according to the manufacturer's recommendation. The membranes were incubated for 5 minutes with the chemiluminescent substrate and exposed to the film. The film was developed using Kodak fixer and developer prepared according to the manufacturer's instructions.

*Plasmodium berghei* GST Knockout Plasmids:

Two different strategies were used to attempt disruption of the pbgst gene and a total of five replacement constructs were made. One strategy includes in using the pL0001 plasmid (BEI Resources—Malaria Research and Reference Reagent Resource Center: MR4), which contains the *Toxoplasma gondii* dihydrofolate reductase-thymidylate synthase (tgdhfr/ts) selection cassette. This plasmid drives a double crossover recombination strategy. The second strategy uses the pL0034 plasmid (BEI Resources~Malaria Research and Reference Reagent Resource Center: MR4), which contains the positive-negative selectable marker cassette (human dihydrofolate reductase/yeast cytosine deaminase and uridyl phosphoribosyl transferase: hdhfr/yfcu) selectable marker under the control of the constitutive eukaryotic elongation factor 1A (eef1a) promoter. This plasmid is a knockout vector with negative selectable marker, which permits restoration of the gene. The *P. berghei* glutathione S-transferase (pbgst) DNA sequence (gene identifier in PlasmoDB as PB301263.00.0) was retrieved from PlasmoDB. The DNA fragments from the 5' region and the 3' region of the pbgst gene were cloned flanking the tgdhfr/ts selection cassette of the plasmid pL0001. Three different knockout plasmids (pbgst-ko construct 1A, pbgst-ko construct 1B and pbgst-ko construct 1C) were generated using different 5' and 3' regions of the pbgst gene. The pbgst-ko construct 1A was previously designed and created by Joel Vega and Shirley Valentin. The 5' targeting region of the pbgst gene was PCR amplified using the primers 64

```
KpnI site is
underlined)                          (SEQ ID NO: 62)
(5'-gggGGTACCAGATCTGCTATACTTAAAATGA

TGGACAACATAGTGC-3';
``` and 65

```
                                     (SEQ ID NO: 63)
(5'-gggAGGCCTAAGCTTCAAAATAACC

TGACCATTTAGGTAATTCTTC-3';
```

HindIII site is underlined) obtaining a 638 bp DNA fragment. To generate the 3' targeting region (553 bp), the primers 68

```
                                     (SEQ ID NO: 64)
(5'-gggGGTACCGGATCCGGGGATACTA

TAACATATGCAGATTTAGCAG-3';
```

BamHI site is underlined) and 69

```
                                     (SEQ ID NO: 65)
(5'-gggGATATCTCTAGAGCACATATTATATA

TGTATGTATATACAATGCTC-3';
```

XbaI site is underlined) was used. The 5' targeting region was cloned into the pL0001 plasmid using KpnI and HindIII while the 3' targeting region was cloned using BamHI and XbaI. The pbgst-ko construct 1B was created using a 586 bp DNA fragment from the 5' region of the pbgst gene which was PCR amplified using the primers 193

```
                                     (SEQ ID NO: 66)
(5'-gggGGTACCCTTAGTTAATCTGAAAGTATATGTTAATAA3';
```

KpnI site is underlined) and 194

(SEQ ID NO: 67)
(5' gggAAGCTTGCGGAAATAAAATTACATAACAC ACAATG-3';

HindIII site is underlined) and then cloned into the KpnI/HindIII digested pL0001 vector to obtain pL0001-5' pbgst. To generate the 3' targeting region, a pbgst gene fragment of 700 bp was PCR amplified with primers 195

(SEQ ID NO: 68)
(5'-gggGGATCCTAGCAAAATAGTATAGTATTATTCTGTTTG-3';

BamHI site is underlined) and 196

(SEQ ID NO: 69)
(5'-gggTCTAGATCATAATGACACACATTCAAAAATAAGGC-3';

XbaI site is underlined) and cloned into BamHI/XbaI pL0001-5' pbgst digested plasmid to create the disruption vector, pbgst-ko construct 1B. The pbgst-ko construct 1C was generated by amplifying a 525 bp DNA fragment from the 5' region of the pbgst gene using the primers 197

(SEQ ID NO: 70)
(5'gggGGTACCGTTAATCTGAAAGTATATGTTAATAACAG-3';

KpnI site is underlined) and 198

(SEQ ID NO: 71)
(5'-gggAAGCTTCTTTATAAATATGGCAAAGAA ATTGAC-3';

HindIII site is underlined), which was cloned into the KpnI/HindIII digested pL0001 vector to obtain pL0001-5' pbgst. To generate the 3' targeting region, a fragment of 718 bp was PCR amplified with primers 199

(SEQ ID NO: 72)
(5'-gggGGATCCC TGCTATTTACTGACTGTTTGTAATTC-3';

BamHI site is underlined) and 200

(SEQ ID NO: 73)
(5'-gggTCTAGACACTATTTTCATTGTTAACACATTTGC-3';

XbaI site is underlined) and cloned into BamHI/XbaI pL0001-5' pbgst digested plasmid to create the disruption vector, pbgst-ko construct 1C. Restriction digestion of all knockout constructs and agarose gel analysis were done in order to confirm a successful cloning of the pbgst 5' and 3' targeting regions flanking the tgdhfr/ts selection cassette into the pL0001 plasmid. The knockout constructs, pbgst-ko construct 1B and pbgst-ko construct 1C, were verified by DNA sequencing of the plasmids. The knockout plasmids (pbgst-ko construct 1A and pbgst-ko construct 1B) were linearized using KpnI/XbaI restriction enzymes and transfected independently into purified schizonts of the *P. berghei* ANKA-GFP line. Table 4 represents primers used for the *Plasmodium berghei* glutathione S-transferase knockout construct using the plasmid backbone pL0001.

TABLE 4

Primers used for the Plasmodium berghei glutathione S-transferase knockout construct using the plasmid backbone pL0001

| SEQ. ID. NO. | Primer Name | Nucleotide Sequence (5'-3') | Mere | Sense (S)/ Antisense (AS) | Target Gene | Restriction Site | Purpose |
|---|---|---|---|---|---|---|---|
| 62 | 64 | GGGGGTACC/AGATGTGCTATACTTAAAATGATGGACAACATAGTGC | 46 | S | pbgst | KpnI/BgII | 5' pbgst targeting region for pbgst-ko construct 1A |
| 63 | 65 | CGGACCCCT/AACCTTCAAAATAACCTGACCATTTAGGTAATCTTC | 46 | AS | pbgst | StuI/HindIII | 5' pbgst targeting region for pbgst-ko construct 1A |
| 64 | 68 | GGGGGTACC/GGATCCGGGGATACTATAACATATGCAGATTTAGCAG | 46 | S | pbgst | KpnI/HindIII | 3' pbgst targeting region for pbgst-ko construct 1A |
| 65 | 69 | GGGGATATC/TCTAGAGCACATATTATATATGTATGTATATACAATGCTC | 49 | AS | pbgst | EcoRV/XbaI | 3' pbgst targeting region for pbgst-ko construct 1A |
| 66 | 190 | GGGGGTACCCTTAGTTAATCTGAAAGTATATGTTAATAAC | 40 | S | pbgst | KpnI | 5' pbgst targeting region for pbgst-ko construct 1B |
| 67 | 194 | GGGAAGCTTGCGGAAATAAAATTACATAACACACAATG | 38 | AS | pbgst | HindIII | 5' pbgst targeting region for pbgst-ko construct 1B |
| 68 | 195 | GGGGGATCCTAGCAAAATAGTATAGTATTATTCTGTTTG | 39 | S | pbgst | BamHI | 3' pbgst targeting region for pbgst-ko construct 1B |
| 69 | 196 | GGGTCTAGATCATAATGACACACATTCAAAAATAAGGC | 38 | AS | pbgst | XbaI | 3' pbgst targeting region for pbgst-ko construct 1B |
| 70 | 197 | GGGGGTACCGTTAATCTGAAAGTATATGTTAATAACAG | 38 | S | pbgst | KpnI | 5' pbgst targeting region for pbgst-ko construct 1C |
| 71 | 198 | GGGAAGCTTCTTTATAAATATGGCAAAGAAATTGAC | 36 | AS | pbgst | HindIII | 5' pbgst targeting region for pbgst-ko construct 1C |

TABLE 4-continued

Primers used for the Plasmodium berghei glutathione S-transferase knockout construct using the plasmid backbone pL0001

| SEQ. ID. NO. | Primer Name | Nucleotide Sequence (5'-3') | Mere | Sense (S)/ Antisense (AS) | Target Gene | Restriction Site | Purpose |
|---|---|---|---|---|---|---|---|
| 72 | 199 | GGGGGATCCCTGCTATTTACTGACTGTTTGT AATTC | 36 | S | pbgst | BamHI | 3' pbgst targeting region for pbgst-ko construct 1C |
| 73 | 200 | GGGTCTAGACACTATTTTGATTGTTAACACAT TTGC | 36 | AS | pbgst | XbaI | 3' pbgst targeting region for pbgst-ko construct 1C |

A second knockout strategy was done to verify the need of the pbgst gene for parasite development in the vertebrate host. The plasmid used in this strategy contains a negative selectable marker that allows restoration of gene to confirm the obtained phenotype. In order to make this plasmid, the pbgst gene was sequenced as described above. The two different knockout plasmids (pbgst-ko construct 2A and pbgst-ko construct 2B) were generated using different 5' and 3' pbgst targeting regions into the pL0034 plasmid. To generate the pbgst-ko construct 2A, the 5' and 3' targeting regions of the pbgst gene were PCR amplified using primer sets 270/271

(SEQ ID NO: 74)
(5'-CCGCGGGTTACCATTACCCAGAGTTCAC-3' and (SEQ ID NO: 75)
5'-CTGCAGCA GCACTATGTTGTCCATC-3')

and 272/273

(SEQ ID NO: 76)
(5'-GATATCCCATTATTAAAAGCCCATA CTG-3' and (SEQ ID NO: 77)
5'-GAATTCGTGTGCGCAGATATGTATAAGC-3').

The PCR-amplified DNA fragments of 556 bp and 654 bp corresponding to 5' and 3' regions respectively were cloned using SacII/PstI and EcoRV/EcoRI (restriction sites underlined into the primer sequence) into pL0034 plasmid. The pbgst-ko construct 2B was generated using primer sets 274/275

(SEQ ID NO: 78)
(5'-CCGCGGCCCACGTTATTTAATAGTTTTAGTTACC-3' and (SEQ ID NO: 79)
5'-CTGCAGGCACTATGTTGTCCATCATTTTAAG-3')

and 276/277

(SEQ ID NO: 80)
(5'-GATA TCCATTATATTGCTAATAGAAAAGAAAGCGTC-3' and (SEQ ID NO: 81)
5'-GAATTCGTTTACTATAA ATCACTTATTTTCTG-3')

to amplify a DNA fragment of 576 bp and 486 bp respectively, which correspond to the 5' and 3' targeting regions. The 5' and 3' regions were cloned using SacII/PstI and EcoRV/EcoRI (restriction sites underlined into the primer sequence) into the pL0034 plasmid. Both knockout plasmids (pbgst-ko construct 2A and pbgst-ko construct 2B) were verified by restriction digestion and agarose gel analyses and DNA sequencing. The knockout plasmids were linearized with SacII, EcoRI and ScaI enzymes and transfected into purified schizonts of the *P. berghei* ANKA-GFP line as described in the *Plasmodium berghei* Transfection section. Table 5 represents primers used for the *Plasmodium berghei* glutathione S-transferase knockout construct using the plasmid backbone pL0034.

TABLE 5

Primers used for the Plasmodium berghei glutathione S-transferase knockout construct using the plasmid backbone pL0034

| SEQ. ID. NO. | Primer Name | Nucleotide Sequence (5'-3') | Mere | Sense (S)/ Antisense (AS) | Target Gene | Restriction Site | Purpose |
|---|---|---|---|---|---|---|---|
| 74 | 270 | CCGCGGGTTACCATTACCCAGAGTTCAC | 28 | S | pbgst | SacII | 5' pbgst targeting region for pbgst-ko construct 2A |
| 75 | 271 | CTGCAGCAGCACTATGTTGTCCATC | 25 | AS | pbgst | PstI | 5' pbgst targeting region for pbgst-ko construct 2A |
| 76 | 272 | GATATCCCATTATTAAAAGCCCATACTG | 28 | S | pbgst | EcoRV | 3' pbgst targeting region for pbgst-ko construct 2A |

TABLE 5-continued

Primers used for the Plasmodium berghei glutathione S-transferase knockout construct using the plasmid backbone pL0034

| SEQ. ID. NO. | Primer Name | Nucleotide Sequence (5'-3') | Mere | Sense (S)/ Antisense (AS) | Target Gene | Restriction Site | Purpose |
|---|---|---|---|---|---|---|---|
| 77 | 273 | GATTCGTGTCCGCAGATATGTATAAGC | 28 | AS | pbgst | EcoRI | 3' pbgst targeting region for pbgst-ko construct 2A |
| 78 | 274 | CCGCGGCCCACGTTATTTAATAGTTTTAGTTACC | 34 | S | pbgst | SacII | 5' pbgst targeting region for pbgst-ko construct 2B |
| 79 | 275 | CTGCAGGCACTATGTTGTCCATCATTTTAAG | 31 | AS | pbgst | PstI | 5' pbgst targeting region for pbgst-ko construct 2B |
| 80 | 276 | GATATCCATTATATTGCTAATAGAAAAGAAAGCGTC | 35 | S | pbgst | EcoRV | 3' pbgst targeting region for pbgst-ko construct 2B |
| 81 | 277 | GAATTCGTTTACTATAAATCACTTATTTTCTG | 32 | AS | pbgst | EcoRI | 3' pbgst targeting region for pbgst-ko construct 2B |

Cloning of PCR Amplified Products and Transformation:

The PCR amplified products to be used for sequencing the pbgst gene and for the construction of the knockout plasmids were ligated into the pCR®2.1-TOPO® (Invitrogen™), which has single overhanging 3' deoxythymidine residues allowing binding to the single overhanging 3' deoxyadenosine present in the PCR products. The ligation of the PCR products was done using Topoisomerase I which is covalently bound to the vector. The ligation reactions were set up as described in the following table:

| Reagent | Volume (μL) |
|---|---|
| PCR Product | 4-8 |
| Salt Solution | 1 |
| Water | Add to a total volume of 9.5 |
| TOPO ® vector | 0.5 |
| Final Volume | 10 |

Cloning of the DNA fragments (targeting regions) into the vector backbone of the designed disruption plasmids was done using T4 DNA ligase (New England BioLabs® Inc.). Ligation reactions were set up as follows:

| Reagent | Negative Control | Ligation |
|---|---|---|
| 10X T4 DNA Ligase Buffer | 1 μL | 1 μL |
| Vector DNA | 25-50 ng | 25-50 ng |
| Insert DNA | — | 10-25 ng |
| T4 DNA Ligase | 1 μL | 1 μL |
| Nuclease-free water | Up to 10 μL | Up to 10 μL |
| Final Volume | 10 μL | 10 μL |

All the reagents were mixed gently and incubated overnight maintaining a temperature of 16° C. Subsequently, ligation reactions were used to transformed competent cells. The E. coli PMC 103 competent cells were used for all transformations. The PMC 103 competent cells (200 L) were thawed on ice and the ligation reaction (5 μL) was added to the cells, and gently mixed, incubated on ice for 30 minutes. The cells were transformed by heat-shocked at 42° C. for 45 seconds in a water bath and immediately transferred to ice for 3 minutes, followed by addition of 800 μL of Luria-Bertani (LB) broth and incubated for 1 hour at 37° C. with moderate agitation. Dilutions of the transformed bacteria were plated on LB agar plates supplemented with 100 μg/mL Ampicillin antibiotic and incubated overnight at 37° C.

Plasmodium berghei Transfection:

The transfection of the Plasmodium berhei is accomplished by electroporation of purified schizonts using the Amaxa® Nucleofector® Technology (Lonza). The transfection protocol includes in vitro culture, purification and electroporation of schizonts followed by the selection of transfectant parasites using the appropriate drug. For in vitro culture of the P. berghei schizonts, the infected blood was collected from the infected mice and transferred to a complete culture medium (RPMI1640 medium with L-glutamine, 25 mM HEPES, without $NaHCO_3$ from Gibco® pH 7.3 supplemented with 25% fetal bovine serum (FBS) from Gibco® heat-inactivated and 50,000 IU of Neomycin stock solution of 10,000 IU/mL from Sigma-Aldrich®) in a Corning® 75 cm2 cell culture flask. The culture was aerated with a gas mixture (5% $CO_2$, 5% $O_2$, 90% $N_2$) for 2 minutes, tightly closed and incubated at 37° C. with gentle shaking for 22 hours to allow the development of the schizonts.

The purification of the mature schizonts was carried out using a 55% Nycodenz/PBS solution (v/v). The method for purification is described as follows: 30 mL of the parasites culture were transferred to a 50 mL centrifuge tube and 10 mL of 55% Nycodenz/PBS solution (v/v) was gently added to the bottom of the cultured blood suspension using a 10 mL pipette (creating a gradient). The gradient was centrifuged at 234×g for 30 minutes at room temperature using a swinging bucket rotor without brake. The mature schizonts were carefully removed from the gradient interface (brown layer) using a Pasteur pipette. The purified schizonts were then transferred to a 50 mL tube, and 20 mL of the culture medium from the top of the gradient were added to wash the schizonts. The schizonts were centrifuged at 234×g for 8 minutes at room temperature. The supernatant was discarded and the schizont pellet was resuspended in culture medium for a final concentration ranging between 1.107-3.107 schizonts per milliliter. The schizont suspension was transferred to 1.5 mL tubes (1 mL per tube) and spin down for 5 seconds. The supernatant was removed and the schizont pellet was resuspended in 100 μL of Basic Parasite Nucleofector® Solution 2 plus Supplement, and 5-10 μg of the DNA construct in 5-10 μL of water. The mixture containing the schizonts, DNA and buffer solution; was transferred to a cuvette and transfection was done by electroporation using the protocol U33 in the Amaxa® Gene Pulser (Lonza). Subsequently, 50 µL of culture medium was added to the cuvette. Transfected parasites were immediately injected (IV) into the mice.

The transfected parasites were selected through drug specific screening dependent of the selectable marker present in the knockout plasmid used for transfection. Pyrimethamine treatment was used to select transfectant parasites (pbgst-ko construct 1A and 1B) harboring the tgdhfr/ts gene as selectable marker. Pyrimethamine was administered in the drinking water. The stock solution containing the pyrimethamine was dissolved in dimethyl sulfoxide (DMSO) to make a final concentration of 7 mg/ml. The stock solution was diluted 100 times with tap water. The pH was maintained to about 3.5-5.0 using 1M hydrochloric acid (HCl). The mice were given the pyrimethamine in their water for a period of 4-7 days, starting one day after infection with the transfectant parasites using the pbgst-ko construct 1A and 1B. The WR99210 (Jacobus Pharmaceutical Company, Inc.) treatment was used to select transfectant parasites (pbgst-ko construct 2A and 2B) that have the hdhfr gene as selectable marker. The WR99210 stock solution was dissolved in DMSO and then diluted with water to make a final 70%/30% DMSO/water solution. The WR99210 treatment consists of a dose of 16 mg/kg body weight and was administered by subcutaneous injection into the mice during four consecutive days.

Southern Blot of *P. berghei* Chromosomes:

The *P. berghei* chromosomes were separated by Contour Clamped Homogeneous Electric Field (CHEF) electrophoresis using the CHEF-DR® III Pulsed Field Electrophoresis System (Bio-Rad). Chromosomes from *H. wingei* (M1) and *S. cerevisiae* (M2) were used as standard markers. The chromosome blocks prepared previously were washed with MilliQ water and were fixed on the teeth of the comb with 0.8% low melting agarose. The comb was placed in a vertical position on the gel casting, and the 0.8% TAE 1× agarose was poured in the gel chamber. After the gel polymerize, the comb was removed and the wells were covered with 0.85% low melting agarose. The gel chamber was dismantled and the gel was placed into the frame of the gel tank. The gel was run in 1×TAE at 14° C. using the following parameters:

| Block | I | II |
| --- | --- | --- |
| Buffer | 14° C. | 14° C. |
| Field Angle | 106° | 106° |
| Volts | 4.5 | 4.5 |
| Start switch | 120 | 120 |
| Final switch | 240 | 240 |
| Run Time | 16 | 36 |

The chromosomal DNA was stained by incubating the gel for 10 minutes in a 5 µg/ml ethidium bromide solution with shaking. The gel was de-stained 10 minutes in demineralized water with shaking, visualized using the Gel Doc™ XR System (Bio-Rad). An image of the gel was taken with a ruler laid alongside which allowed to later identifying the band position on the membrane. The chromosomal DNA was transferred to a membrane by capillary blotting. The gel was rinsed with demineralized water, placed in a clean dish and further treated twice with 0.25 M HCl for 15 minutes with slow shake at room temperature. In the next step, it was rinsed with the demineralized water and then covered with denaturation buffer (0.5 M NaOH, 1.5 M NaCl) for 30 minutes with moderate shaking. After denaturation of the gel, it was incubated with 20× Saline Sodium Citrate (SSC) buffer for 30 minutes at room temperature with moderate shaking. The chromosomes were transferred overnight by capillarity to a Nylon GeneScreen Plus® Hybridization Transfer Membrane (PerkinElmer Inc.) using 10×SSC buffer. The membrane was incubated at 80° C. for at least 2 hours in order to fix the chromosomes. The membrane was stored at room temperature until hybridized.

To confirm integration of the knockout construct into the endogenous gst gene, the resultant parasites from the transfections were analyzed by Chromosome blot analysis of separated chromosomes by CHEF or Field Inverted Gel Electrophoresis (FIGE). The chromosomes from parasites transfected with the pbgst-ko construct 1 (pL0001 used as backbone plasmid) were hybridized to a tgdhfr/ts probe to confirm plasmid integration into the endogenous chromosome. The 921 bp tgdhfr/ts probe was obtained by digestion of the pL0001 with SalI enzyme. The chromosomes from the parasites transfected with the pbgst-ko construct 2 (pL0034 used as backbone plasmid) were hybridized with a hdhfr probe. The 774 bp hdhfr probe was obtained by digestion with BamHI enzyme. Both fragments, 921 bp tgdhfr/ts and 774 bp hdhfr, were gel extracted and purified using the Wizard® SV Gel and PCR Clean-Up System (Promega). The probes were labeled with $\alpha$-$^{32}$P dATP using the NEBlot® Kit. The procedure is as follows: 25 ng of DNA template were labeled by a random primer labeling reaction with 1 µL DNA Polymerase I–Klenow Fragment (3'→5' exo-) using 50 Ci of $\alpha$-$^{32}$P dATP. The mixture was incubated at 37° C. for 1 hour. Unincorporated $\alpha$-$^{32}$P dATP nucleotides were removed by purifying the probes using Micro Bio-Spin® P-30 Tris Chromatography Columns (Bio-Rad) as indicated by the manufacturer.

The membranes were pre-hybridized by incubation in hybridization buffer (6×SSC, 5×Denhardt's, 0.5% (v/v) SDS, 0.1% (v/v) disodium pyrophosphate, 15 µg/ml tRNA) for 1 hour at 65° C. The denaturation of the probes were attained by boiling for 5 minutes at 100° C., and then adding to the pre-hybridization solution containing the membrane. Hybridization was done overnight at 60° C. with gentle shaking. The membranes were washed 3 times with a solution containing 3×SSC and 0.1% (v/v) SDS; followed by one wash with 1×SSC, 0.1% (v/v) SDS. The washes were done for 15 minutes at 60° C. in order to remove non-specific binding of the probe. The membranes were exposed to Kodak Omat X-ray films with an intensifying screen at −80° C. The membranes were stripped by incubating 2 times with a 0.1×SSC, 0.5% SDS (v/v) solution for 15 minutes at 90° C.

Structural Homology Model of *Plasmodium berghei* Glutathione S-Transferase:

The tertiary structure of the monomer of the *P. berghei* GST was obtained using the I-TASSER server. The *P. falciparum* GST structure with PDB code 1Q4J was used as a template molecule to generate the homology model. The default values were used to generate the pbGST model. The *P. berghei* gst sequence that was obtained by a PCR sequencing strategy was translated to a protein sequence and used to generate the homology model. The pbGST predicted protein sequence is identical to the reported sequence available at PlasmoDB (PBANKA_102390). Subsequent analysis and visualization of the 3D structural model was performed using PyMOL (DeLano, 2002). The pbGST protein model was superimposed with the PfGST-GSH bound structure (PDB code 3FR9) and the binding sites (G and H sites) were analyzed and compared.

ChEMBL-Neglected Tropical Disease Archive 21 and 22:

The ChEMBL is a chemical database and contains datasets of thousands of compounds and is based on compound screening campaign from various sources including: whole *Plasmodium* and *Trypanosoma* organisms. The datasets used in this study were downloaded from the ChEMBL-NTD web-interface. The compounds from each dataset were divided into active and inactive compounds, filtered for duplicates. All the compounds were pooled and re-filtered for duplicates. The compounds were selected based on their ADMET properties by using the FILTER tool from OpenEye Scientific Software. The resulting compounds were used to perform the virtual library screening (VLS) against the pbGST protein.

Tres Cantos Antimalarial TCAMS Dataset: The Tres Cantos Antimalarial Set (TCAMS) is a dataset that contains the small molecule structures and screening results for over 13,500 compounds, confirmed to inhibit *P. falciparum* blood stage parasite growth by more than 80% at 2 µM concentration. Additionally, this dataset has data for selectivity screening of human cell cytotoxicity. The compounds from this dataset were filtered using the FILTER tool (OpenEye Scientific Software) and ADMET properties. The compounds that fulfilled these requirements were used for the VLS against the two binding sites (G-site and H-site) of the pbGST protein.

ChemBridge Library: ChemBridge Corporation is a provider of screening compounds and libraries for small molecule drug discovery. The compounds from this database have a diverse chemical structure in terms of new scaffolds and high quality standard of 100% by nuclear magnetic resonance (NMR) identification with at least 90% of purity. The compounds from this database were filtered out for ADMET properties before running the VLS and further used to perform the in silico screening against one of the binding site of the pbGST, the G-site.

Structure Based Virtual Library Screening (VLS):

The VLS were conducted for the G-site and H-site binding site of the pbGST protein using the ChEMBL-NTD, and the ChemBridge library. The VLS used for each database was a structure-based method that applies docking scoring computations and uses a 3D structural model of the pbGST as target protein. The ChemBridge library was used only for G-site. Each dataset was screened independently using identical procedures. The VLS protocol start with the removal of inappropriate and undesirable compounds from the compound databases to be screened. The OpenEye tool FILTER was used with the default parameters to filter the compounds based on the following criteria: physical properties; atomic and functional group content; and molecular topology. The FILTER tool includes a filter-drug that identifies the compounds that could be suitable as drugs; and a filter-lead that identify compounds that could be lead molecules. In addition, the FILTER tool was used to eliminate duplicate compounds. Moreover, The OMEGA2 tool from OpenEye was used to generate conformers of each molecule. The produced conformers were low in energy to ensure that the conformers are diverse and possess a low-energy conformational space. A maximum of 2,000 conformers for each compound were prepared using OMEGA2. Once all the conformers were generated, they were used to perform the docking analysis.

The docking analyses were done using FRED (Fast Rigid Exhaustive Docking) with the standard parameters (McGann, 2012). Prior to the docking analysis, a receptor for the pbGST was made using the make receptor function from OEDocking toolkit covering the entire molecule to detect the potential binding sites in the surface conformation without constraints. The two binding sites were detected corresponding to the G-site and H-site; and the docking was conducted for these two binding sites. The molecules that positioned outside the defined region for docking were discarded. The docking analyses are scored by the exhaustive scoring function and generate a FRED Chemgauss4 score that is reported for each compound. This means that each pose is scored with Chemgauss4 and the best scoring poses were retained. The Chemgauss4 score of the molecule was used to rank the molecule versus other molecules in the docking. Therefore, the docking was set up to the best scoring pose's score. The docking analyses derived virtual library hits that were subjected to visual inspection.

The docking results were visualized using the OpenEye visualization software, (VIDA). The molecules were examined one at a time and analyzed on the 3D surface structure, which allows to obtain information about the relative position and potential interactions in the binding site. The docking poses were analyzed visually for the following parameters before submitting for biological evaluation: formation of hydrogen bonds by ligand atoms with residues of the pbGST binding sites, reasonable ligand conformation and energetically favorable interaction. Molecular visualization of the selected compounds from the docking analyses was done using PyMOL for visualizing the predicted interactions and to produce images. The compounds with the best conformational and energetic values were selected for further analysis using the *Plasmodium berghei* in vitro drug luminescence assay.

Tres Cantos Antimalarial TCAMS Compounds:

The compounds were received as 10 mM stocks dissolved in 100% DMSO. These stocks were stored at −20° C. The DMSO stock compounds were diluted in complete culture medium (RPMI1640 medium supplemented with 20% FBS from Gibco® heat-inactivated and Neomycin stock solution of 10,000 IU/mL from Sigma-Aldrich®) for use in the *Plasmodium berghei* in vitro drug luminescence assay. For initial testing, the compounds were used at the following concentration: 0.01 µM, 0.1 µM, 1 µM and 10 µM; in triplicate point to determine the inhibition curve for each compound. The compounds that did not show activity against schizont development were excluded and not taken into further consideration. The compounds that demonstrated an inhibition at the tested range of concentrations were chosen for accurate half maximal effective concentration (EC50) value determination against the *Plasmodium berghei* in vitro drug luminescence assay at three independent experiments each one in triplicate point.

Antimalarial Activity using the In vitro Drug Luminescence Assay: To assess the antimalarial activity and the effective concentration (50% of the maximal inhibition; $EC_{50}$ values) of the potential pbGST inhibitors, the in vitro drug luminescence (ITDL) assay was done by the method disclosed in the prior art. This assay measures the in vitro development of *P. berghei* ring stage into mature schizonts in the presence of inhibitors/drugs. The Swiss-CD1 female mice were infected with the GFP-luc parasite line. The GFP-luc parasite line allows determination of the luciferase activity in the cultured mature schizonts, which is directly proportional to the number of schizonts. When the parasitemia reaches 1-3%, the RBCs were collected from the infected mice and used to perform the assay. The susceptibility of blood stages parasites was determined in the presence of standard GST inhibitors and the TCAMS compounds identified from the VLS. The following previously described standard GST inhibitors were used: S-hexylglutathione, ellagic acid, ethacrynic acid and curcumin; all purchased from Sigma-Aldrich®. The standard GST inhibitors were weighed and dissolved in 100% DMSO to prepare the stock solution. Dilutions of the standard GST inhibitors were freshly prepared in complete culture medium (RPMI1640 medium supplemented with 20% FBS from Gibco® heat-inactivated and Neomycin stock solution of 10,000 IU/mL from Sigma-Aldrich®) for each assay. The dilutions of the inhibitors were added to the wells in triplicates, 50 µL per well. Chloroquine diphosphate salt from Sigma-Aldrich® was used as a control (at a concentration of 100 nM) for complete inhibition of blood stage development. Further, infected blood was collected from one mouse by cardiac puncture under anesthesia early in the morning (between 9:00-10:00 µm). The blood was added to a 50 mL tube containing 5 mL complete culture medium supplemented with 300 µL heparin stock solution (25,000 U/mL). The blood was centrifuged for 8 min at 450×g and the supernatant was removed. The blood was resuspended in a complete culture medium comprising a concentration of 2% (v/v). In the next step, 50 µL of the blood suspension was added in each well containing the inhibitors dilutions. The 96-well black culture plates containing the infected blood solution were placed into a candle jar. The candle jar was carefully flushed with a gas mixture of 5% $CO_2$, 5% $O_2$, 90% $N_2$ using a 0.22 µm filter unit connected to the gas hose for 2 minutes. The lid was tightly closed immediately after gassing. The infected blood suspension was incubated at 37° C. with continuous agitation (enough to keep the cells suspended) for 24 hours allowing the ring stages to develop into the mature schizonts. After the culture period, the schizonts were evaluated by microscopic examination of Diff Quick-stained thin blood smears. The 96-well plate was centrifuged at 1,000×g for 5 minutes. The supernatant was removed using a syringe needle on those sides of the wells without red blood cell after spinning. The luciferase activity was measured in cultured mature schizonts using the Luciferase Assay System Kit from Promega (Cat. No. E1500). The RBCs were lysed by adding 50 µL of 1× cell culture lysis reagent into each well. The plate was shaken for 5 minutes to assure complete lysis. Afterward, 50 µL of the luciferase assay reagent was added. The luminescence was measured using the SpectraMax® M3 Microplate Reader (Molecular Devices). The luciferase activities are reported as relative luminescence units (RLU) for each sample and the RLU for each inhibitor/drug concentration was calculated from the same experiment performed in triplicate. The data was analyzed and used to generate standard in vitro inhibition curves, and EC50 values of each compound were calculated. Preliminary data analyses were performed using Microsoft Excel and the effective concentration (50% of the maximal inhibition; $EC_{50}$ values) were calculated using GraphPad Prism software (Graph-Pad software, Inc., US, Mac Version 6). The data analysis was performed which consists of the following: (1) The mean RLU value of "complete inhibition control" (i.e., the maximum concentration of the drug) is subtracted from the mean RLU values of all the other wells/concentrations. (2) The mean RLU value of wells without drug ("no inhibition control=control no drug") is taken as the maximal RLU value and given to indicate normal parasite development. (3) All RLU values of experimental wells (i.e., parasites in the presence of inhibitors) are divided by the mean value of the "no inhibition control" in order to calculate the percentage of inhibition. The growth inhibitory curves were plotted as parasite growth (%) in the Y axis versus log of compound concentration in the X axis on a semi-log graph. To calculate the $EC_{50}$ values the non-linear regression function for sigmoidal dose-response (variable slope) was used. For each compound, the inhibition curves of at least three independent experiments were reported.

Glutathione S-transferase Activity in Blood Stage Parasites: The parasite extracts were prepared as the method described in the Protein for Enzymatic Activity. The enzymatic activity was determined spectroscopically using the chromogenic substrate 1-chloro-2,4-dinitrobenzene (CDNB) from Sigma-Aldrich®. The GST activity was assayed at 25° C. in P. berghei protein extracts by monitoring the increase in absorbance at 340 nm on the basis of the extinction coefficient for the product S-(2,4-dinitrophenyl) glutathione ($\varepsilon_{340\ nm}$=9.6 mM$^{-1}$ cm$^{-1}$). The absorbance was measured in a 96-well plate (UV flat bottom Microtiter®, from Thermo Scientific) using the SpectraMax® M3 Microplate Reader (Molecular Devices). The parasite extract (0.65 mg/mL) and 1 mM CDNB were added to a 100 mM potassium phosphate (pH 6.5) buffer. The reaction was started by adding 1 mM GSH. To detect any residual GST activity associated with the parasite extract, blank reactions as controls (no GSH) were included. The Enzyme activity is reported as units (micromole of GSH/min)/mg of protein. This assay was standardized using the human placenta GST from Sigma-Aldrich® (Cat No. G8642) and used as positive control.

Inhibition of *Plasmodium berghei* Glutathione S-Transferase:

The compounds stock solutions were prepared in 100% DMSO. Dilutions of S-hexylglutathione (Sigma-Aldrich®) were prepared using a 25% DMSO solution and the final concentration of DMSO in the assay was 2.5%. For S-hexylglutathione, inhibition curve was plotted as GST activity (%) in the Y axis versus log of compound concentration in the X axis on a semi-log graph. The half maximal inhibitory concentration ($IC_{50}$) values were calculated using the non-linear regression function for sigmoidal dose-response (variable slope). Inhibition curves of pbGST was done in two independent experiments with one replicate each (n=2) whereas the inhibition curves of hGST was determined in three independent experiments in triplicate (n=9). In addition, the data obtained by varying the S-hexylglutathione concentration was analyzed using a column bar graph. GraphPad Prism software (Graph-Pad software, Inc., US, Mac Version 6) was used to make the graph and to perform the statistical analyses. Inhibition of pbGST by the S-hexylglutathione was done in duplicate, whereas the inhibition of hGST was done in three independent experiments, each in triplicate. Statistical analysis was done for the inhibition of hGST by S-hexylglutathione. A one-way analysis of variance was used to compare the GST activity in the presence of S-hexylglutathione using a 0.05 confidence level for significance. The Bonferroni's correction for multiple comparisons was used to test for differences between the control (no compound added) and the effect of S-hexylglutathione dilutions against the human placenta GST.

The GSK TCAMS compounds dilutions were prepared in DMSO and the final concentration of DMSO in the assay was 0.5%. Inhibition of pbGST by the GSK TCAMS compounds were determined by adding variable concentration of compounds (1, 10 and 50 µM) with a fixed *P. berghei* protein extracts concentration (0.65 mg/mL) in a total volume of 200 µL containing 1 mM CDNB and 100 mM potassium phosphate buffer (pH 6.5) at 25° C. The reaction was started by adding 1 mM GSH and activity was measured spectroscopically at 340 nm absorbance. The data obtained by varying compound concentration was analyzed using a column bar graph. Inhibition of pbGST by the GSK TCAMS compounds was done in duplicate. One GSK TCAMS compound, TCMDC-124132, was analyzed against the hGST in two independent experiments in triplicate (n=6). A statistical analysis was done using the GraphPad Prism software (Graph-Pad software, Inc., US, Mac Version 6). A one-way analysis of variance was used to compare the hGST activity in the presence of the TCMDC-124132 compound using a 0.05 confidence level for significance. The Bonferroni's correction for multiple comparisons was used to test for differences between the control (no compound added) and the effect of TCMDC-124132 compound dilutions against the hGST.

Results

Figure 1:
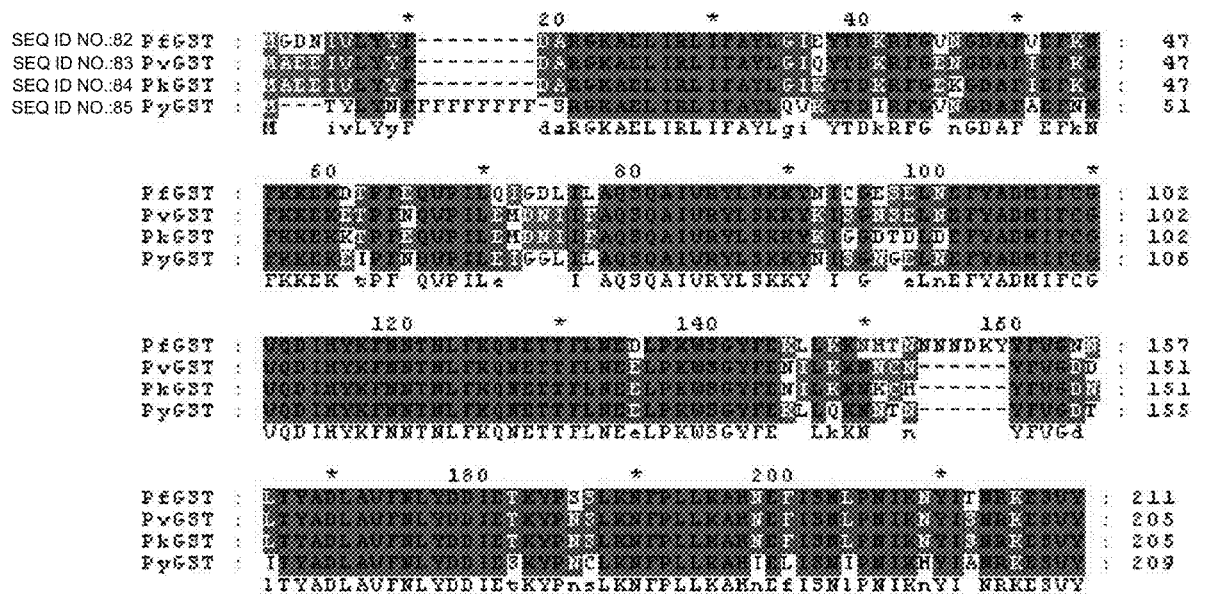

Referring to FIG. 1 shows an alignment of the *Plasmodium* spp. GST protein sequences. The multiple sequence alignment of predicted protein sequences from four *Plasmodium* spp. GST including *P. falciparum* GST (PfGST), *P. vivax* GST (PvGST), *P. knowlesi* GST (PkGST) and *P. yoelii* GST (PyGST) are shown in FIG. 1. The predicted protein sequences used in the alignment are listed in Table 1. The multiple sequence alignment of the *Plasmodium* spp. GST protein sequences show that PfGST has an insertion of six amino acids (NNNDKY) that are not present in the other *Plasmodium* spp. In addition, PyGST is characterized for an insertion of eight phenylalanine (F) residues. Multiple sequence alignment of *Plasmodium* spp. GSTs sequences revealed a significant degree of sequence identity ranging from 80% to 87%. Results revealed that the GST sequences are highly conserved in all four species of *Plasmodium*.

Figure 3:
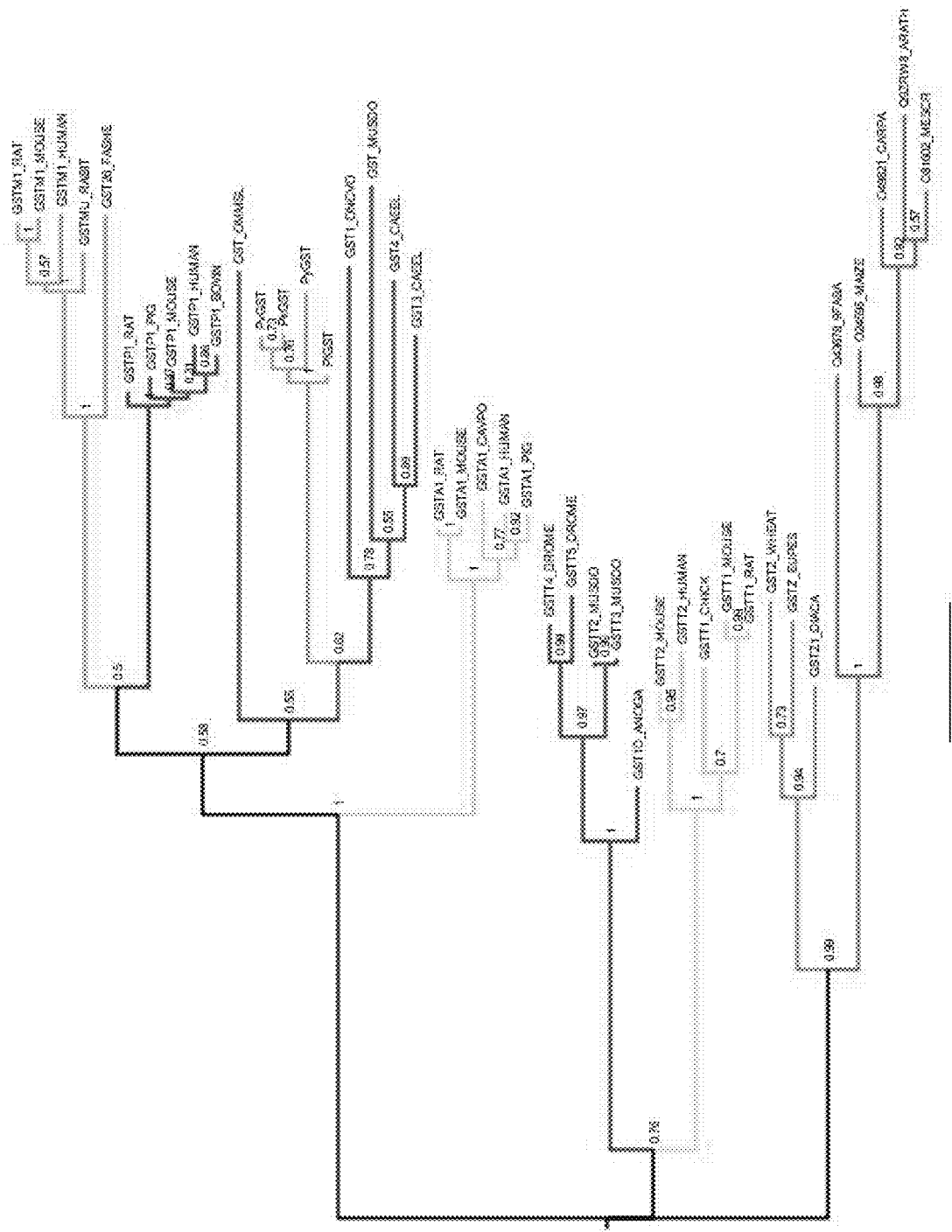
FIG. 3 is phylogenetic tree for the *Plasmodium* spp. glutathione S-transferase proteins

The *P. falciparum* GST (Q8MU52) was used to perform sequence similarity searches using a BLAST search in iProClass. Referring to FIG. 2 is a schematic sequence alignment of four *Plasmodium* spp. GSTs and 38 GST sequences from eight GST classes. Result from the sequence alignment and motif analyses show that the *Plasmodium* GSTs are highly related to the alpha and sigma families of GST (FIG. 2). Referring to FIG. 3 is phylogenetic tree for *Plasmodium* spp. glutathione S-transferase proteins. The *Plasmodium* spp. GSTs are grouped as separate cluster within the sigma class of GSTs. The bootstrap values of the branches support the clades on the phylogenetic tree. The phylogenetic tree indicates that *Plasmodium* spp. GSTs analyzed are members of the sigma class of GSTs. The three-dimensional structures of GST enzymes from various classes (alpha and sigma) were compared to the PfGST 3D structure (1Q4J) by structural alignment. The 3D structures used in the structural alignments are listed in Table 2.

Referring to FIG. 4A-4D are structural alignment of *P. falciparum* GST with sigma GST from *O. volvulus* and alpha GST from human. The structural alignments of PfGST 3D structure (1Q4J) with alpha and sigma 3D structures are presented in FIG. 4A-4D. FIG. 4A shows the structural alignment of PfGST (1Q4J) with sigma GST from *Oncocherca volvulus* (2HNL). A close-up view showing the α-helix of the C-terminus is represented in FIG. 4B. FIG. 4C shows the structural alignment of PfGST (1Q4J) with the alpha GST from human (1PKZ). A close-up view showing the C-terminus is represented in the FIG. 4D. Analysis of the 3D structural alignment of PfGST with the sigma GST from *O. volvulus* shows high structural similarity in the C-terminus (FIG. 4B). The 3D structural alignment of PfGST and the human alpha GST demonstrates a good alignment, but the C-terminus shows low similarity (FIG. 4C). In addition, our results show that PfGST does not have the extended helix in the C-terminus that is distinctive of the alpha class of GST (FIG. 4D).

Referring to FIG. 5A-5D is a structural comparison of GST structures from *P. falciparum* GST with a sigma GST from *O. volvulus* and an alpha GST from human. Furthermore, analysis of the 3D structure of PfGST in the N-terminal domain (G-site) and C terminal domain (H-site) was performed. Structural alignment of the N-terminal domain, that contains the G-site, reveals that PfGST shares a common backbone fold with the sigma (2HNL) GST from *O. volvulus* and alpha (1PKZ) GST from human (FIGS. 5A and 5C). Both structure alignments show a similar binding mode for S-hexylglutathione (GSH derivative). Close views of the N-terminal domain of PfGST against the sigma (2HNL) GST from *O. volvulus* and alpha (1PKZ) GST from human are shown in FIGS. 5A and 5C, respectively. Structural alignment of the C-terminal domain, that contains the H-site, shows that PfGST shares a common backbone with *O. volvulus* sigma GST (2HNL), while human alpha GST (1PKZ) is different, specifically in the C-terminus shown in FIGS. 5B and 5D, respectively. A comprehensive analysis of the 3D structure of PfGST in the H-site, G-site and C-terminus of the proteins was done revealing that these regions have high similarity with the sigma class GST from *O. volvulus* (2HNL). The structural alignments support the results obtained with the phylogenetic tree. The three-dimensional structure superimposition results allowed the classification of *Plasmodium* GSTs as members of the sigma class of GSTs.

Analysis of the *Plasmodium berghei* Glutathione S-Transferase (pbgst) Gene:

An analysis of the PlasmoDB and Sanger Institute databases show an incomplete sequence (partial coding region) of the pbgst gene. In order to perform molecular biology studies of the pbgst gene, a PCR strategy was used to sequence the full coding region of the pbgst gene. FIG. 6A-6B is a *Plasmodium berghei* glutathione S-transferase gene structure of a coding region. The sequence corresponding to the open reading frame was amplified by PCR using genomic DNA or cDNA (obtained by Reverse-Transcription) from *P. berghei* ANKA-GFP line (FIG. 6A). Referring to FIG. 7 is a nucleotide and predicted amino acid sequences of the *Plasmodium berghei* glutathione S-transferase. The genomic sequence of the pbgst consists of 808 bp in length (FIG. 7). The sequence analysis and comparison of the genomic DNA and cDNA sequences revealed a transcript composed of two exons containing 38 bp and 580 bp, respectively (FIG. 6B). The exons are separated by a 190 bp intron (FIG. 6B). Based on the sequence analysis the coding sequence consists of 618 bp. The DNA and cDNA sequences of the pbgst gene were submitted to GenBank (accession numbers are pending). The pbgst sequence is identical to the one subsequently reported in the PlasmoDB database (gene identifier in GeneDB as PBANKA_102390). Referring to FIG. 8A-8B is a diagrammatic representation of the coding region of the human and rodent *Plasmodium* spp. glutathione S-transferase gene. The comparison of the gene structure with those GSTs among other *Plasmodium* species shows that *P. berghei* gst gene is conserved between all *Plasmodium* spp. including the human malarial parasite, *P. falciparum* (FIG. 8A). The length of exon 1 is identical for all *Plasmodium* spp. reported, however the length of exon 2 is different in *P. falciparum* containing 598 bp as compared to the other *Plasmodium* spp., which is 580 bp (FIG. 8B). The exon 2 from *P. falciparum* is distinguished by an insertion of six amino acids in position 140-145 (NNNDKY), increasing its length (FIG. 1). Interestingly, intron lengths show differences between the *Plasmodium* species: 129 bp in *P. falciparum*, 148 bp in *P. vivax*, 159 bp in *P. knowlesi,* 190 bp in *P. berghei,* 247 bp in *P. yoelii,* and 158 bp in *P. chabaudi* (FIG. 8A-8B).

Figure 9:
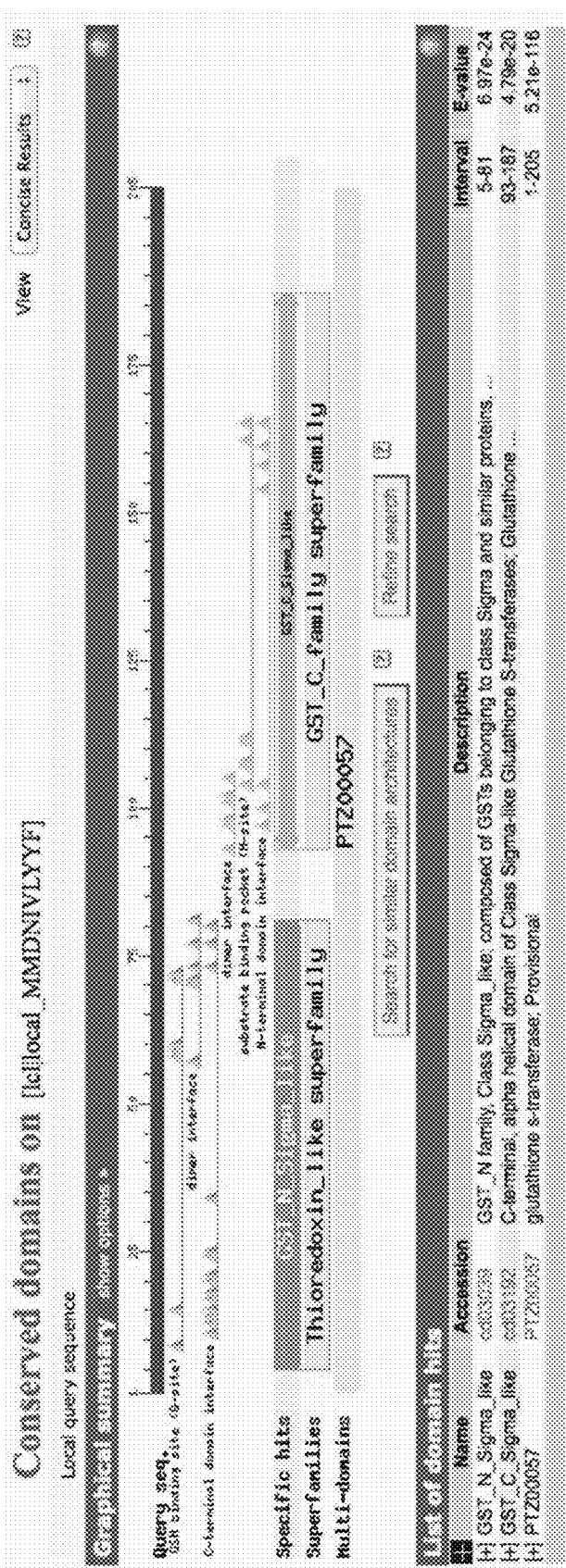
FIG. 9 shows the *Plasmodium berghei* glutathione S-transferase conserved domains.
Figure 10:
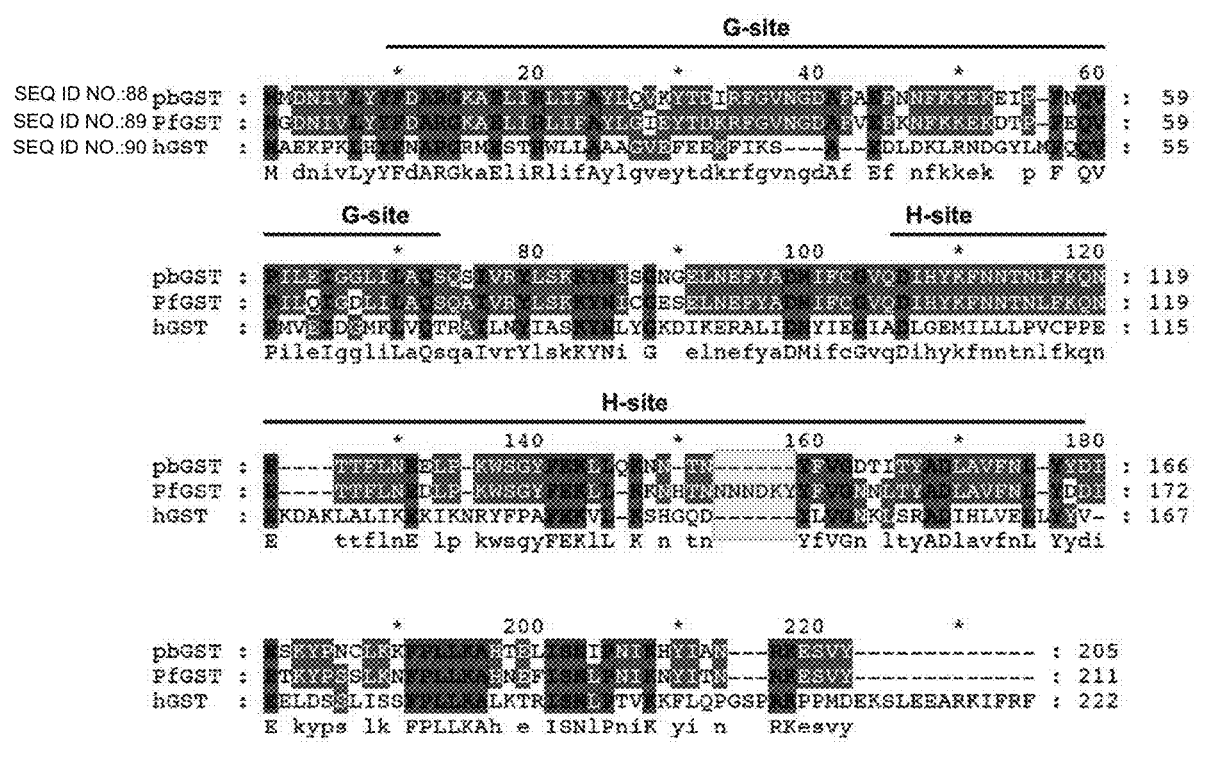

The pbGST contains the GST N-terminal and C-terminal domains and the Thioredoxin-like domain characteristic of GST proteins. FIG. 9 shows the *Plasmodium berghei* glutathione S-transferase conserved domains. Similar results were obtained using the NCBI's Conserved Domain Database showing that the pbGST contains the conserved GST_N_Sigma_like and the GST_C_Sigma_like domains (FIG. 9). Results from the analysis of the conserved domains indicate that the pbGST contains an N-terminal Thioredoxin_like superfamily and C-terminal alpha helical domains. The predicted amino acid sequence of the *P. berghei* GST was aligned with the *P. falciparum* GST revealing a high degree of sequence identity, which differs only in the absence of six amino acids (NNNDKY—position 140-145). FIG. 10 shows a sequence alignment of *P. berghei, P. falciparum* and human GST homologues.

Referring to FIG. 11A-11C is an expression analysis of the *Plasmodium berghei* glutathione S-transferase. The pbgst gene encodes a predicted protein of 205 amino acids with a predicted molecular mass of approximately 24 kDa. Similar to its homolog in *P. falciparum*; the western blot analysis of the blood stage protein extracts using a rabbit polyclonal antibody against PfGST detected a protein of ~50 kDa under non-reducing conditions (native) (FIG. 11A, left panel) and a denatured protein consisting of ~25 kDa under reducing conditions (denatured) (FIG. 11A, right panel). The HSP70 monoclonal antibody was used as a loading control (FIG. 11B). To assess the expression of the pbgst gene, the mRNA level was evaluated using RT-qPCR (FIG. 11C). The RT-qPCR data shows the relative gene expression as fold increase over time. The data was normalized against the expression of 18s rRNA. The RT-qPCR data demonstrated that the pbgst is expressed in parasite blood stages (FIG. 11C). Results from Western blot analysis and RT-qPCR data confirmed the pbGST expression during the parasite blood stages.

Figure 14:
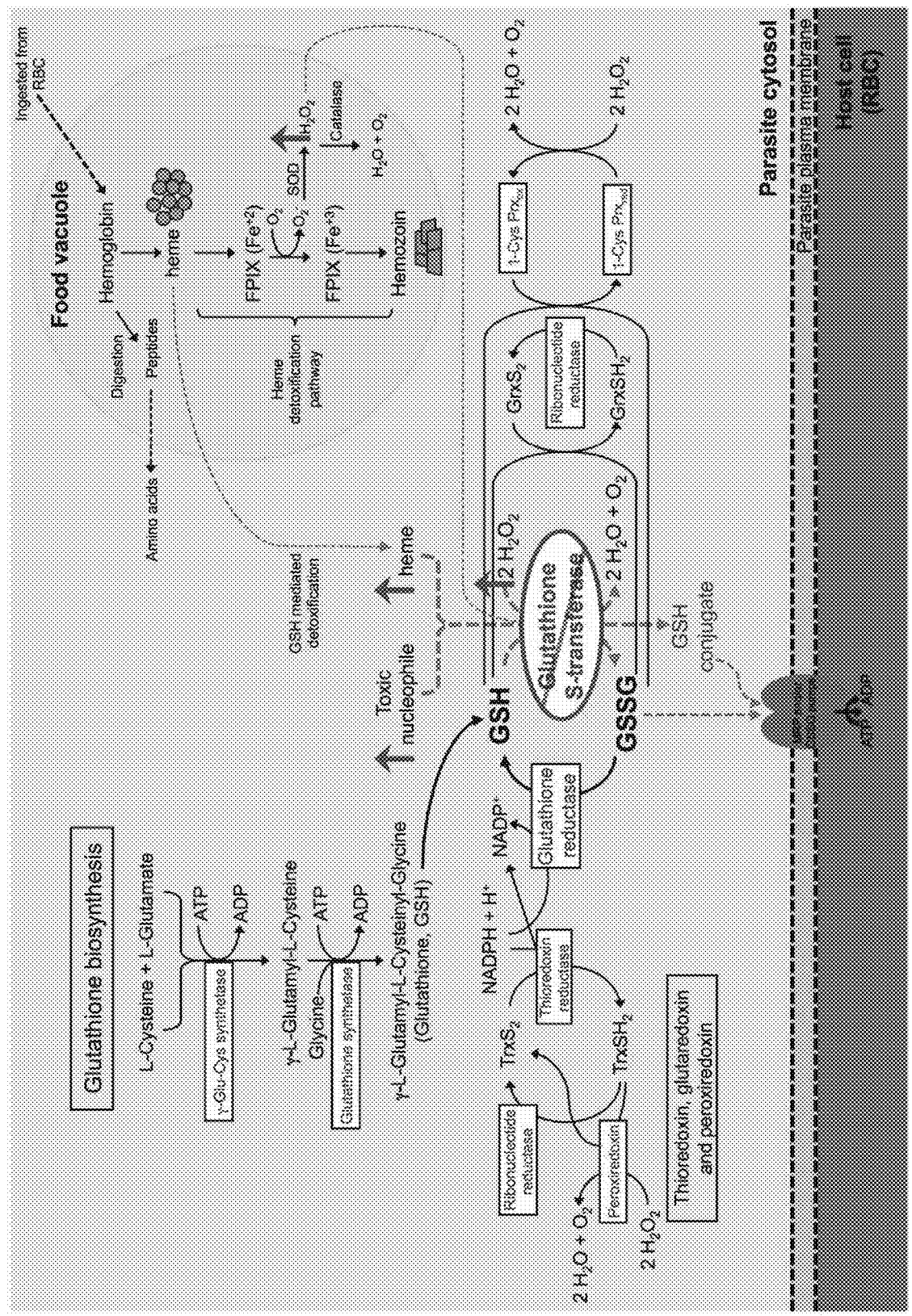
FIG. 14 shows an importance of the GST enzyme in the *Plasmodium berghei* intracellular blood stages.

Referring to FIG. 12A-12E is a diagrammatic representation of the pbgst-ko construct 1 and analysis of potential integration. To investigate whether the *P. berghei* gst gene is essential for parasite development in the vertebrate host, the gene in the *P. berghei* (ANKA-GFP line) was attempted to disrupt. A double crossover recombination strategy was used to design and generate two pbgst knockout constructs (named aspbgst-ko construct 1A and pbgst-ko construct 1B). The pbgst-ko construct 1A generated includes the majority of the pbgst gene, excluding only 39 bp of the pbgst gene between the two targeting regions (FIG. 12A). The pbgst-ko construct 1B generated includes a portion of an adjacent gene (PB102380) (FIG. 12B). This results states that the full pbgst gene sequence was not available in the databases at the time of the constructs design. Further both the constructs contained the 5' and 3' pbgst targeting regions, which will drive the recombination event resulting in the replacement of the pbgst region by the tgdhfr ts selectable marker cassette. This selectable marker allows selection of mutants using treatment with the drug pyrimethamine. The schematic representation of the predicted integration event for the pbgst-ko construct 1A and pbgst-ko construct 1B are presented in FIG. 12A and FIG. 12B. Four independent transfections were carried out (FIG. 12E); no mutant parasites were selected in two transfections while pyrimethamine resistant parasites were selected in the other two transfections. The southern blot analyses of the two samples, from the independent electroporated parasites, show no integration in the pbgst locus (Chromosome 10) (FIG. 12C). This initial observation suggests that the absence of the pbgst gene has a negative effect in the development of the parasite in the blood stages. Additionally, to further confirm unsuccessful transfections attempts one transfection was carried out by Leiden collaborators at their site, obtaining similar results (no integration at the predicted locus, FIG. 12D). FIG. 13A-13D is a diagrammatic representation of the pbgst-ko construct 2 and analysis of potential integration. To further determine if the pbgst gene is essential for the parasite development in the blood stages, an alternative strategy to attempt disruption of the pbgst gene was done using the hdhfr yfcu positive-negative selectable marker system. Two different knockout plasmids (named aspbgst-ko construct 2A and pbgst-ko construct 2B) were generated (FIG. 13A). These constructs contain the hdhfr gene as a selectable marker allowing selection of parasites using treatment with the drug WR99210. These constructs were designed after sequencing the pbgst sequence and the targeting regions selected include only the 5' and 3' regions of the pbgst gene. The two independent transfections were done using these knockout plasmids and WR99210 resistant parasites were obtained (FIG. 13D). The southern blot analysis of eight samples, from independent electroporated parasite, showed no integration of the knockout plasmid in the predicted pbgst locus in Chromosome 10 (FIGS. 13B and 13C). These results demonstrated that pbGST has an important role in the parasite blood stages in vivo and their disruption has a detrimental effect in the parasite development. FIG. 14 shows an importance of the GST enzyme in the *Plasmodium berghei* intracellular blood stages. These unsuccessful attempts to disrupt the pbgst using two different strategies and four different constructs indicate that the pgbst gene is essential for parasite blood stage proliferation (FIG. 14).

Figure 16:
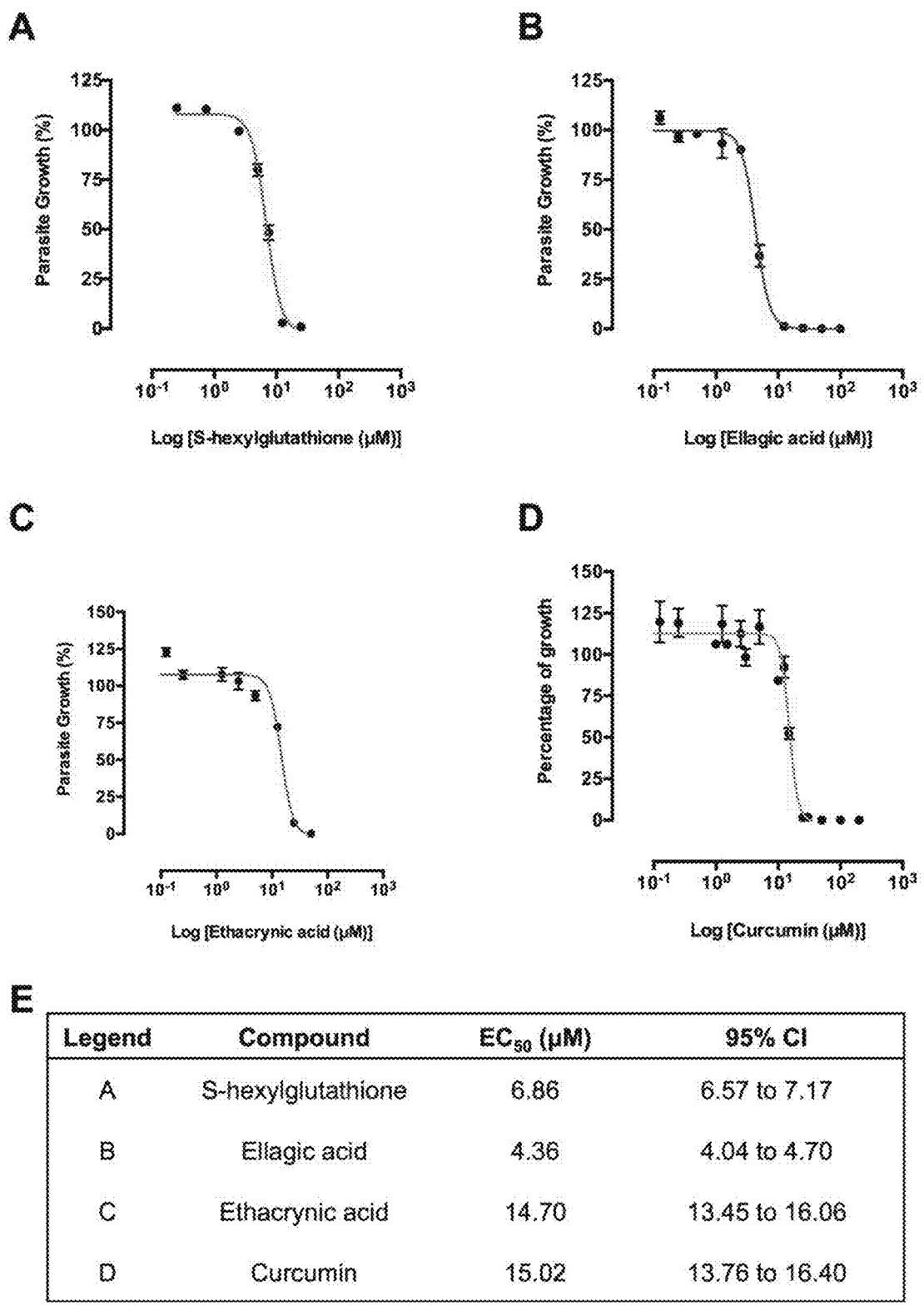
FIG. 16A-16E shows the *Plasmodium berghei* in vitro drug luminescence assay of standard GST inhibitors.

Susceptibility of *Plasmodium berghei* Blood Stages to Standard GST Inhibitors: The GSTs have been associated with drug resistance of cells and organisms including the parasites. To determine if the standard GST inhibitors (S-hexylglutathione, ellagic acid, ethacrynic acid and curcumin) have an effect against the *P. berghei* blood stages development an in vitro drug luminescence assay was conducted. Results from the in vitro *P. berghei* assay shows that standard GST inhibitors causes the parasite growth inhibition. FIG. 16A-16E shows the *Plasmodium berghei* in vitro drug luminescence assay of standard GST inhibitors. The growth inhibition curves and $EC_{50}$ values of three independent experiments for each of the standard GST inhibitor are shown in FIG. 16A-16E. The $EC_{50}$ values of the standard GST inhibitors were 4.36 μM for ellagic acid followed by 6.86 μM S-hexylglutathione, 14.70 μM ethacrynic acid and 15.02 μM curcumin. The 95% confidence interval for the $LogEC_{50}$ of each of the inhibitor is shown in FIG. 16E. The effect of the standard GST inhibitors studied in the growth of the *P. berghei* blood stages confirms that pbGST plays a role in the development in vivo. These results provide evidence that the standard GST inhibitors have an effect in the *P. berghei* blood stages.

Figure 17:
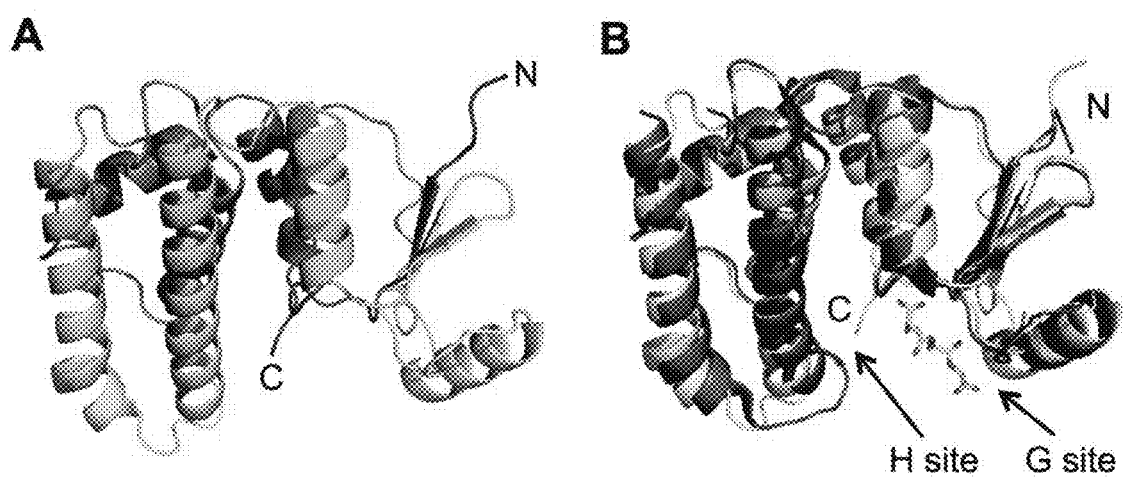
FIG. 17A-17B shows a tertiary structure of the *Plasmodium berghei* GST monomer and structural superposition of pbGST with the PfGST-GSH bound structure.
Figure 18:
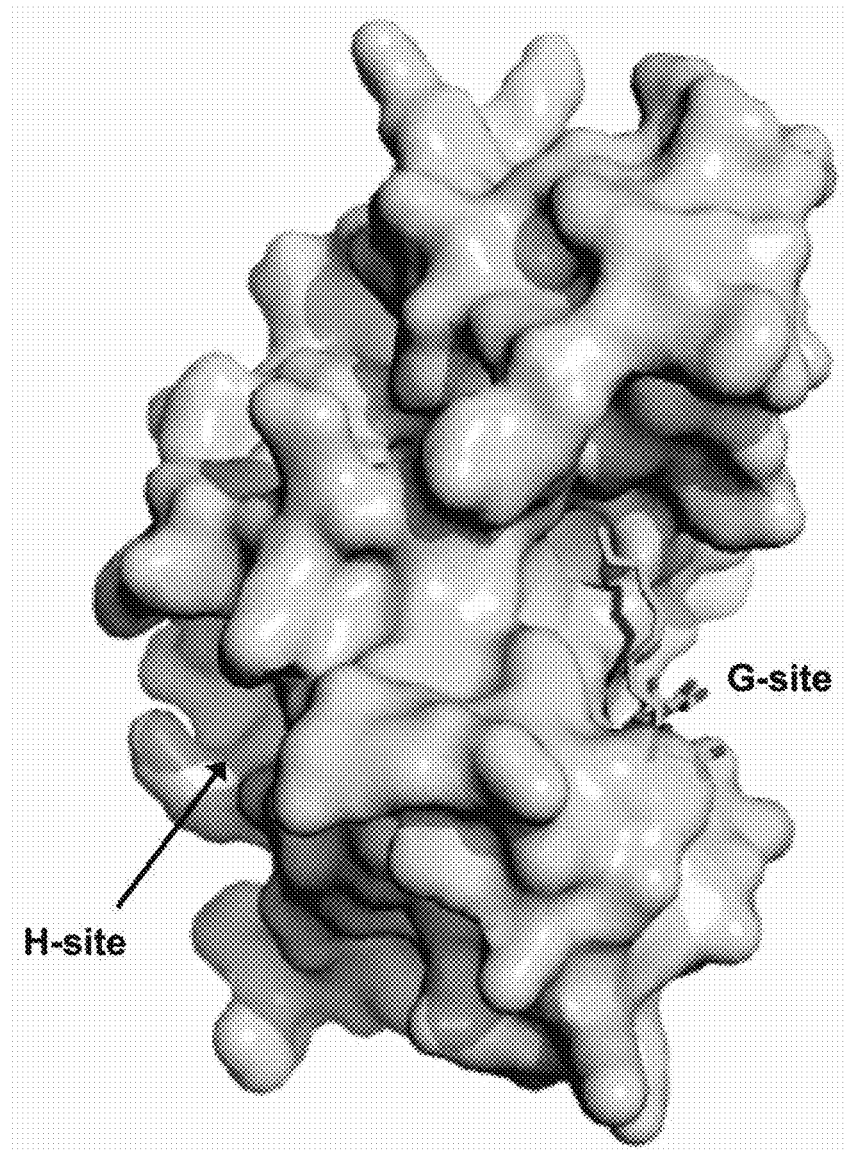
FIG. 18 illustrates an identification of the binding sites on the pbGST surface structure.
Figure 19:
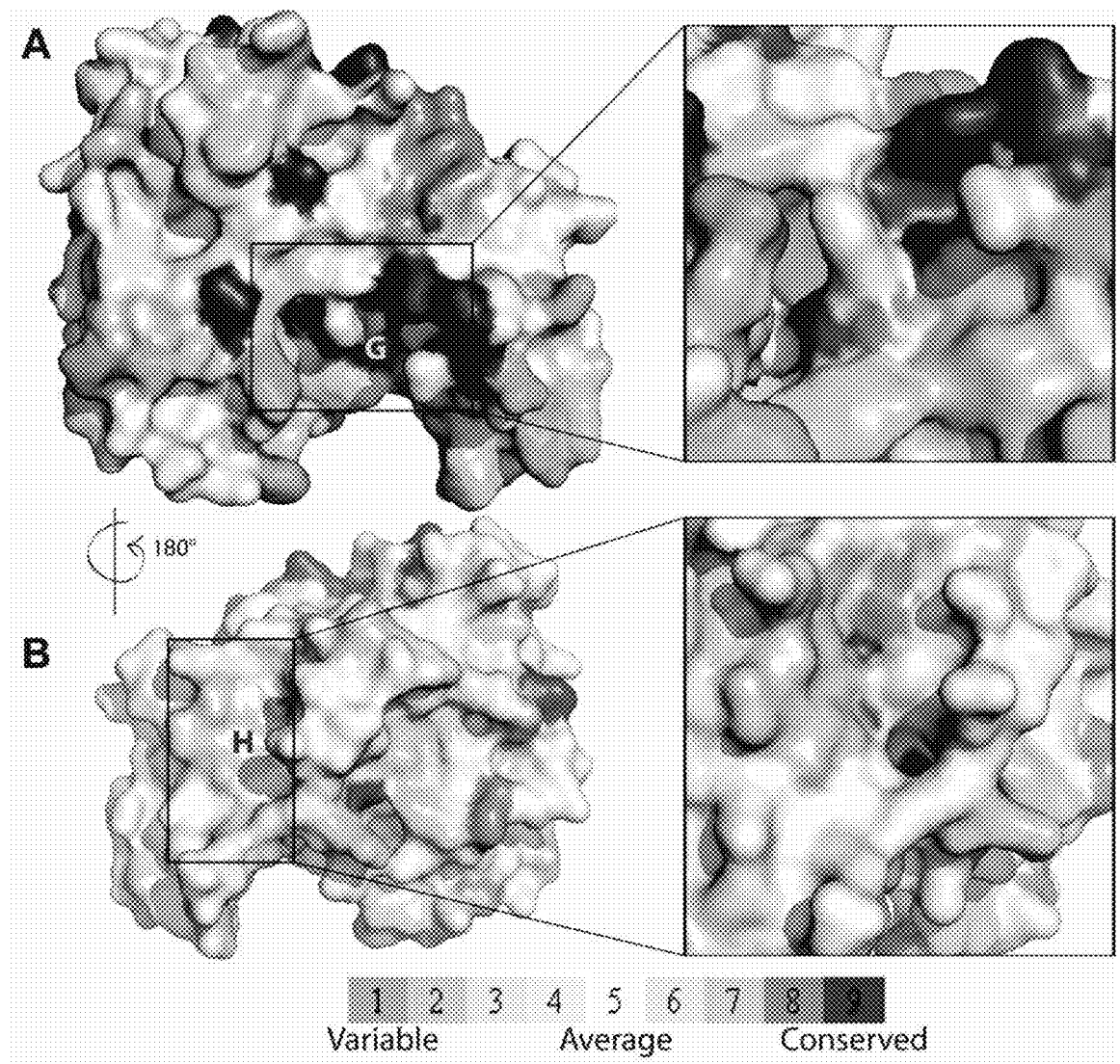
FIG. 19A-19B shows a comparison of a G and H binding sites in the *P. berghei*, *P. falciparum* and human GST homologues.

In Silico Screening of Two Chemical Libraries: ChEMBL-Neglected Tropical Disease Archive and the ChemBridge Library:

FIG. 17A-17B shows a tertiary structure of the *Plasmodium berghei* GST monomer and structural superposition of pbGST with the PfGST-GSH bound structure. To discover the novel antimalarial compounds, a virtual library screening was performed using the ChEMBL-NTD Archive against pbGST. As shown in FIG. 17A, a pbGST structural homology model was generated by comparative modeling and used to perform the VLS. FIG. 18 illustrates an identification of the binding sites on the pbGST surface structure. The VLS was done against the pbGST structural model (FIG. 18), taking into consideration that the binding sites in *P. berghei* and *P. falciparum* are very similar and conserved (FIG. 17B). The model predicts that compounds that bind to the pbGST binding pockets will similarly bind to the PfGST pockets. Referring to FIG. 19A-19B shows a comparison of the G and H binding sites in the *P. berghei*, *P. falciparum* and human GST homologues. The comparison of the G and H binding sites of *P. berghei*, *P. falciparum* and three human GST homologues using the ConSurf Server indicates that the G-site is highly conserved in the three GSTs species (FIG. 19A). In contrast, the H-site differs between the *Plasmodium* and the human GSTs, being this site more variable (FIG. 19B).

The VLS were conducted for the two binding sites (G-site and H-site) of the pbGST protein (FIG. 18). The VLS of the ChEMBL-NTD Archive identified 500 virtual library hits showing potential interaction with the pbGST

TABLE 6

Summary of the virtual library screening results.

| Criteria | Libraries ChEMBL-NTD archive | ChemBridge library |
|---|---|---|
| Library Size | 4,000,000 | 900,000 |
| Compounds Screened | 26,773 | 740,000 |
| Virtual Library Hits | 500 | 2,000 |
| Selected Molecules | 21 | 20 |

Figure 20:
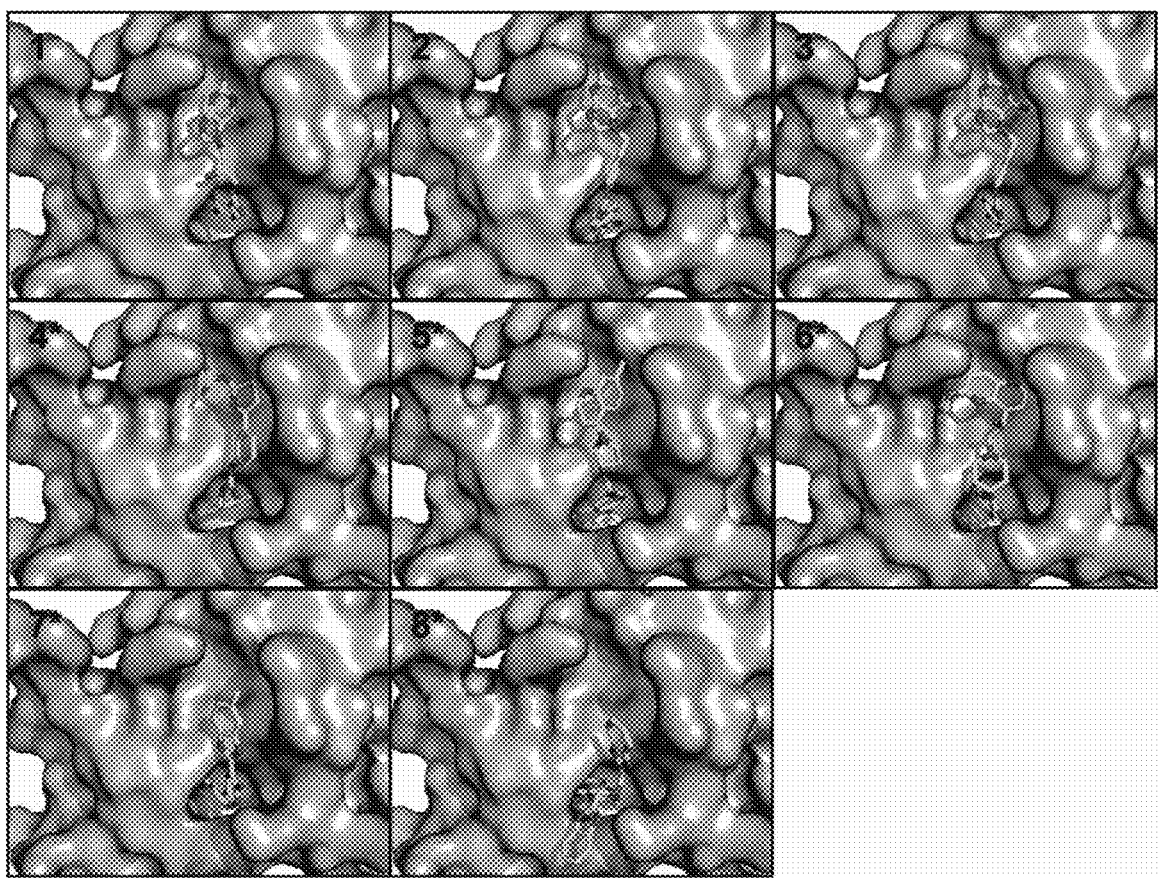
FIG. 20 is a docking representation of the ChEMBL-NTD compounds on the H binding pocket of the *P. berghei* GST protein.

The docking conformations of the ligands into the pbGST binding sites were evaluated considering all chemical features. Referring to FIG. 20 is a docking representation of the ChEMBL-NTD compounds on the H binding pocket of the *P. berghei* GST protein. A total of 21 compounds predicted to bind the pbGST binding pockets were obtained from the VLS of the ChEMBL-NTD Archive. Table 7 and FIGS. 29A-29E represent the compounds identified through virtual library screening of the ChEMBL-Neglected Tropical Disease Archive against pbGST.

TABLE 7

| Compound | CID [TCMDC code] | Mol. Wt. | Binding Site | Docking Score |
|---|---|---|---|---|
| 1 | 44346773 | 362.771 | H-site | −15.0265 |
| 2 | 44346824 | 442.4236 | H-site | −14.6433 |
| 3 | 587171 | 394.8144 | H-site | −14.0962 |
| 4 | 44533692 [139553] | 380.4667 | H-site | −13.8463 |
| 5 | 44526004 [133661] | 419.8274 | H-site | −13.8256 |
| 6 | 44528139 [134945] | 481.4945 | H-site | −13.5265 |
| 7 | 44525306 [133132] | 322.3115 | H-site | −13.4112 |
| 8 | 623893 [124132] | 407.4704 | H-site | −13.4088 |
| 9 | 44405216 | 390.4781 | G-site | −9.8628 |
| 10 | 44530598 [136818] | 476.5259 | G-site | −9.5236 |
| 11 | 44530596 [136816] | 530.4972 | G-site | −9.4398 |
| 12 | 44532358 [138323] | 549.59 | G-site | −8.9777 |

TABLE 7-continued

| Compound | CID [TCMDC code] | Mol. Wt. | Binding Site | Docking Score |
|---|---|---|---|---|
| 13 | 44522315 [125362] | 399.5329 | G-site | −8.6325 |
| 14 | 44523644 [132196] | 450.4638 | G-site | −8.6177 |
| 15 | 5905592 | 286.2827 | G-site | −7.7447 |
| 16 | 44523646 [132198] | 450.4638 | G-site | −7.5457 |
| 17 | 15595291 | 429.6385 | G-site | −7.3656 |
| 18 | 44523911 [132371] | 483.5383 | G-site | −6.9847 |
| 19 | 44522225 [124853] | 425.567 | G-site | −6.9293 |
| 20 | 44535716 | 428.5692 | G-site | −6.7252 |
| 21 | 15595296 | 373.5322 | G-site | −6.6734 |

Figure 21:
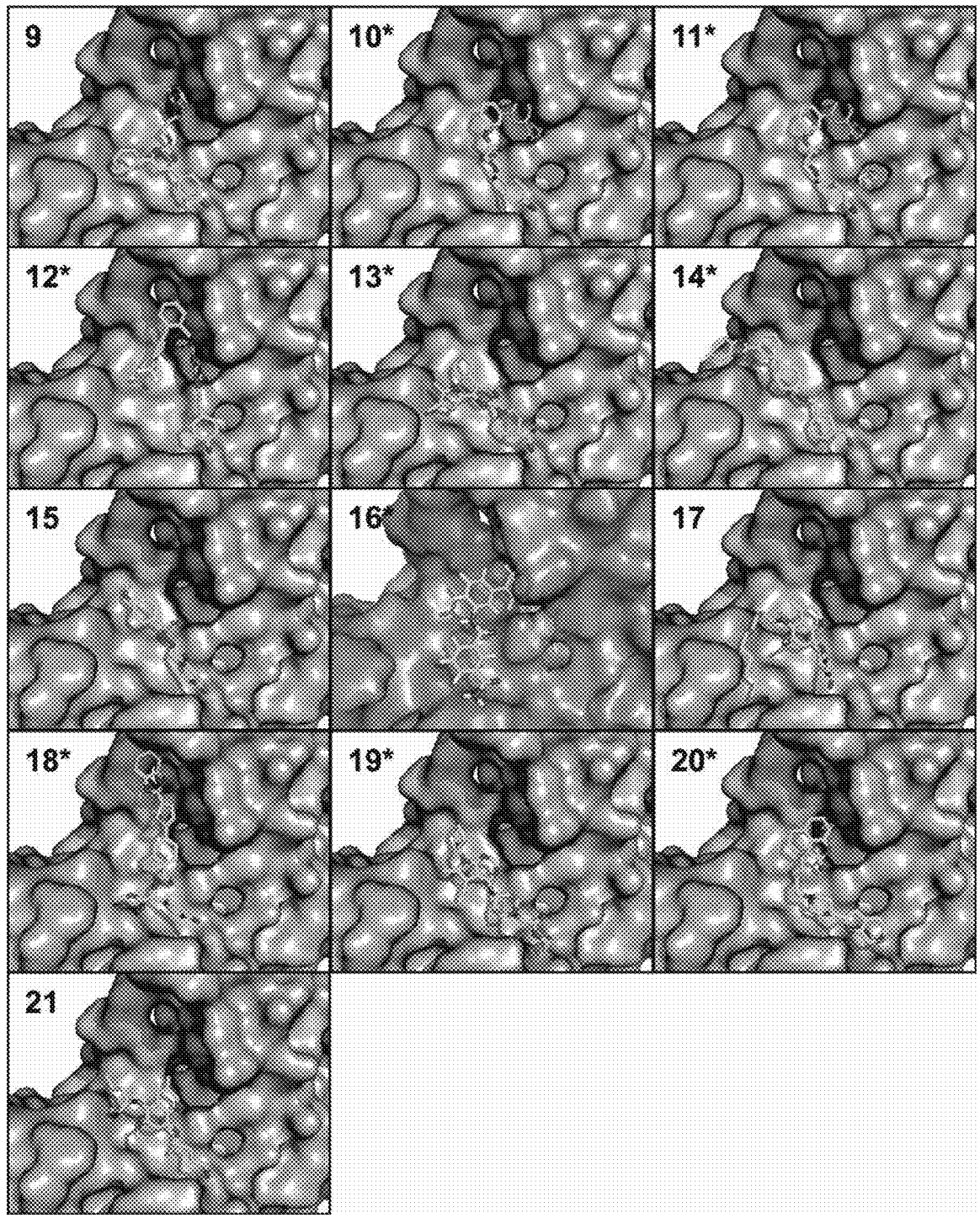
FIG. 21 is a docking representation of the ChEMBL-NTD compounds on the GSH binding pocket of the *P. berghei* GST protein.

Referring to FIG. 21 is a docking representation of the ChEMBL-NTD compounds on the GSH binding pocket of the *P. berghei* GST protein. The in silico docking of the compounds within the respective binding site are shown in FIGS. 20 and 21. The docking analyses show favorable binding interactions between the small molecule compounds and the pbGST protein. Eight compounds are predicted to bind into the H-site (FIG. 20) and 13 compounds to the G-site (FIG. 21). The ChEMBL-NTD Archive comprises 11 datasets including the GlaxoSmithKline Tres Cantos Antimalarial Set (GSK TCAMS). From the 21 compounds identified by the VLS of the ChEMBL-NTD archive, 14 compounds from the GSK TCAMS Dataset were obtained. These 14 compounds are identified in Table 7 with the TCMDC codes, which were prioritized for biological evaluation based on the interactions with the binding sites. In order to find the novel compounds with antimalarial potential, a VLS was performed using the ChemBridge library. The VLS was carried out against the pbGST structural model as described above for the ChEMBL-NTD Archive. The screening was performed only against the G-site of the pbGST protein. A total of 2,000 virtual library hits were identified with potential interaction in the G-site of the pbGST protein (Table 6). Through the VLS 20 small molecules were selected (Table 6) and predicted to bind the G-site of the pbGST. In silico docking of the 20 selected compounds showed binding interactions between the compounds and the G-site binding pocket of the pbGST protein. These compounds represent an important step in the discovery of the novel compounds with antimalarial activity since they have not been tested in the malarial parasite, *Plasmodium*.

Antimalarial Activity of the Identified Compounds from the GSK TCAMS Dataset

Figure 15:
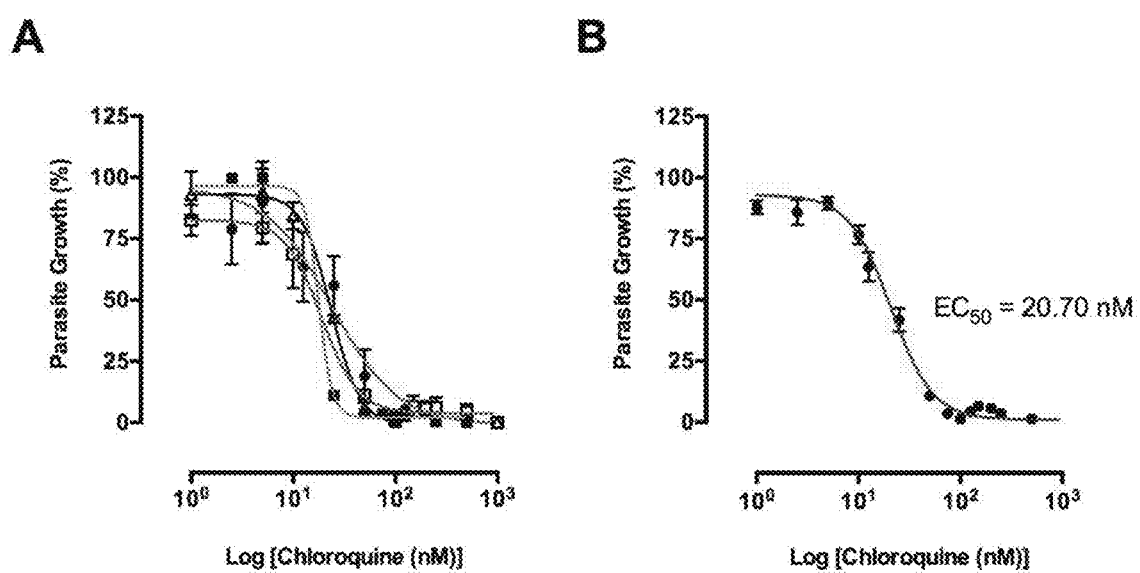
FIG. 15A-15B shows standardization of the *Plasmodium berghei* in vitro drug luminescence assay using Chloroquine.

The *P. berghei* in vitro drug lumincescence assay was employed to determine the potential antimalarial activity of the compounds identified through the VLS. Initially, the ITDL assay was standardized using Chloroquine. Referring to FIG. 15A-15B shows standardization of the *Plasmodium berghei* in vitro drug luminescence assay using Chloroquine. Results from the in vitro drug susceptibility with CQ indicated an $EC_{50}$ value of 20.70 nM (six independent experiments in triplicate each) shown in FIG. 15B. Chloroquine $EC_{50}$ value are consistent with the published results ($EC_{50}$=20 nM; of this drug, confirming the accuracy of the assay.

Figure 22:
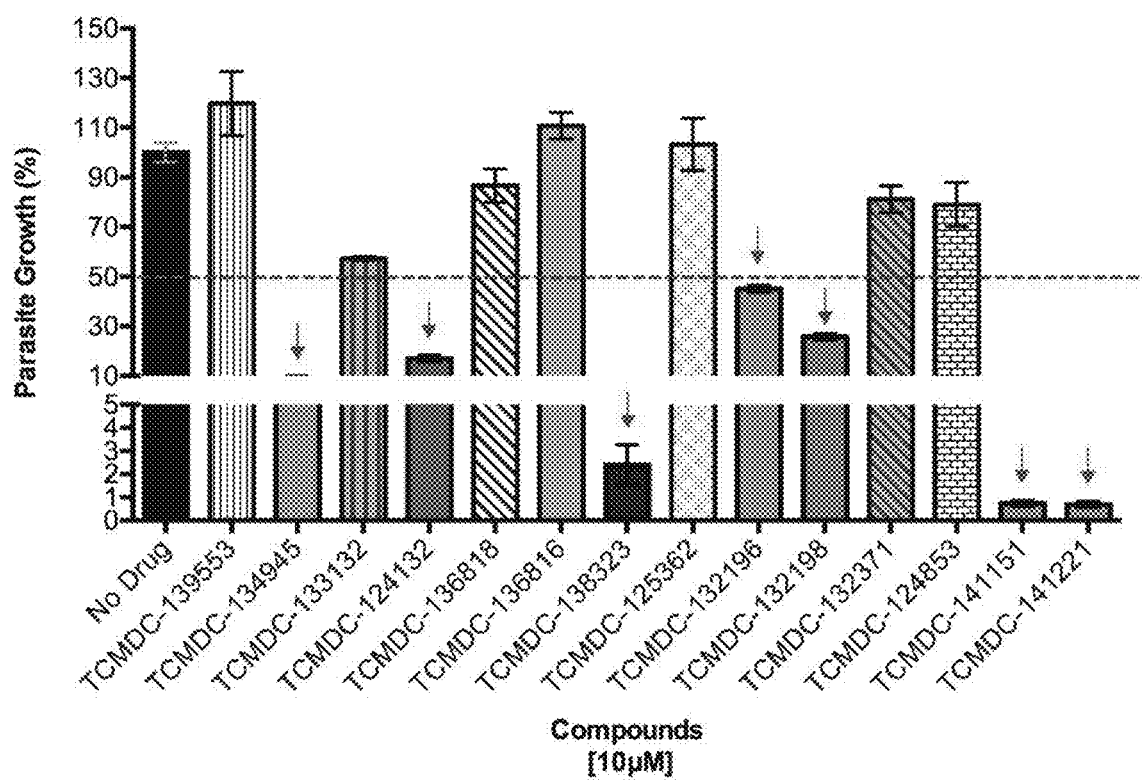
FIG. 22 shows a growth inhibition against the *Plasmodium berghei* using the 14 GSK TCAMS compounds at 10 µM.
Figure 29A:
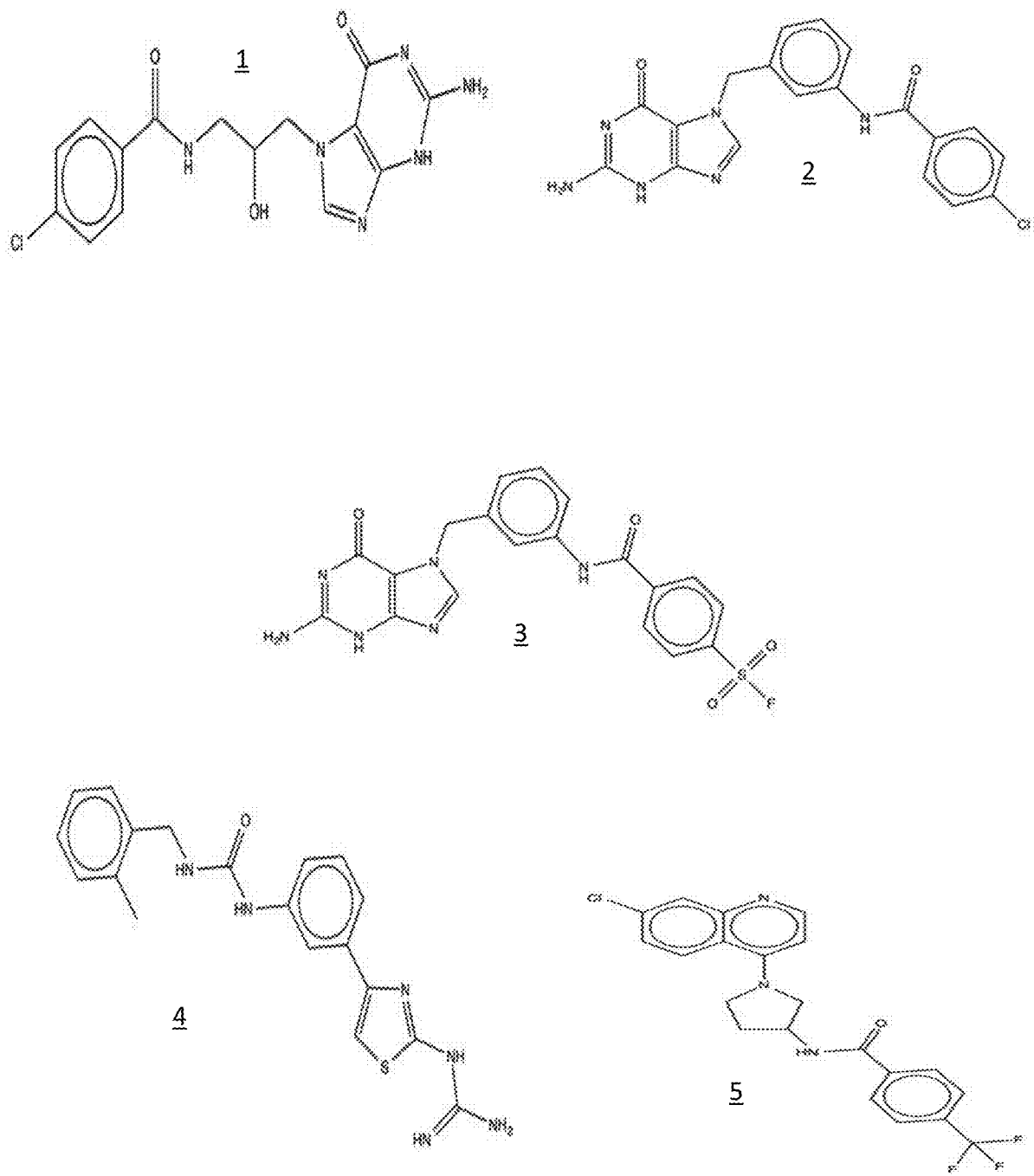
FIG. 29A-29E show the structure of the compounds identified through virtual library screening of the ChEMBL-Neglected Tropical Disease Archive against pbGCT, according to the present invention.
Figure 29B:
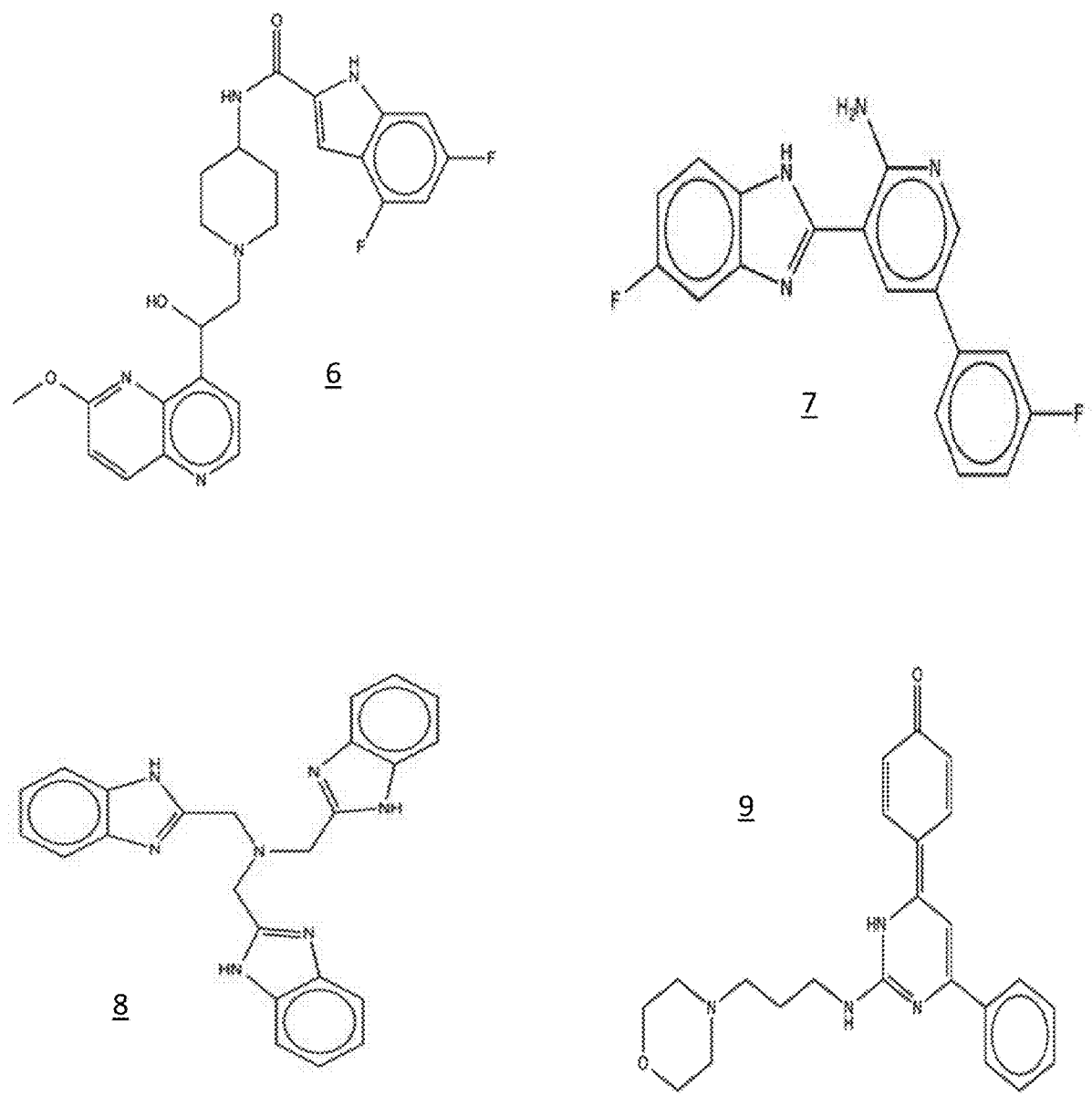
Figure 29C:
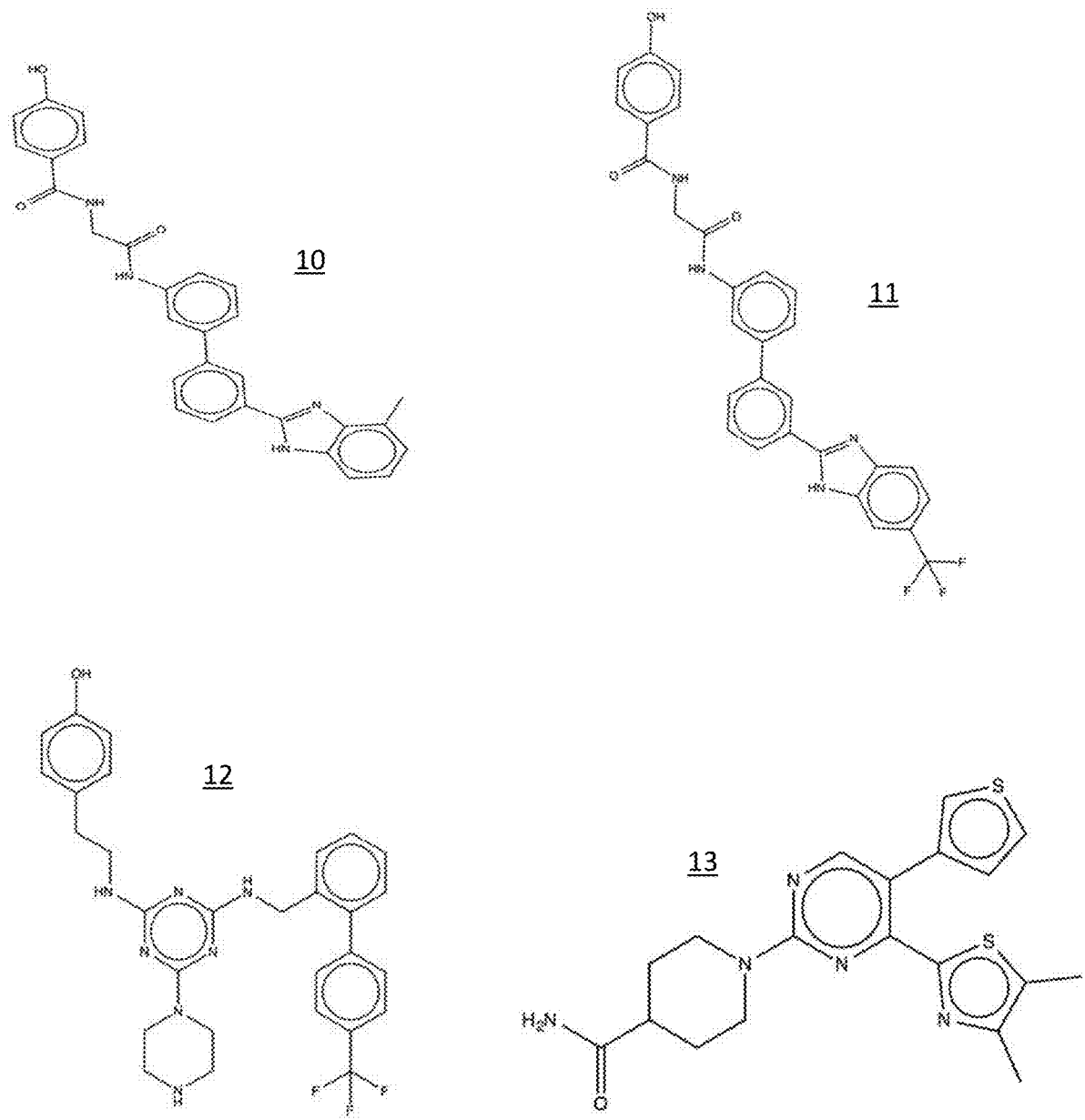
Figure 29D:
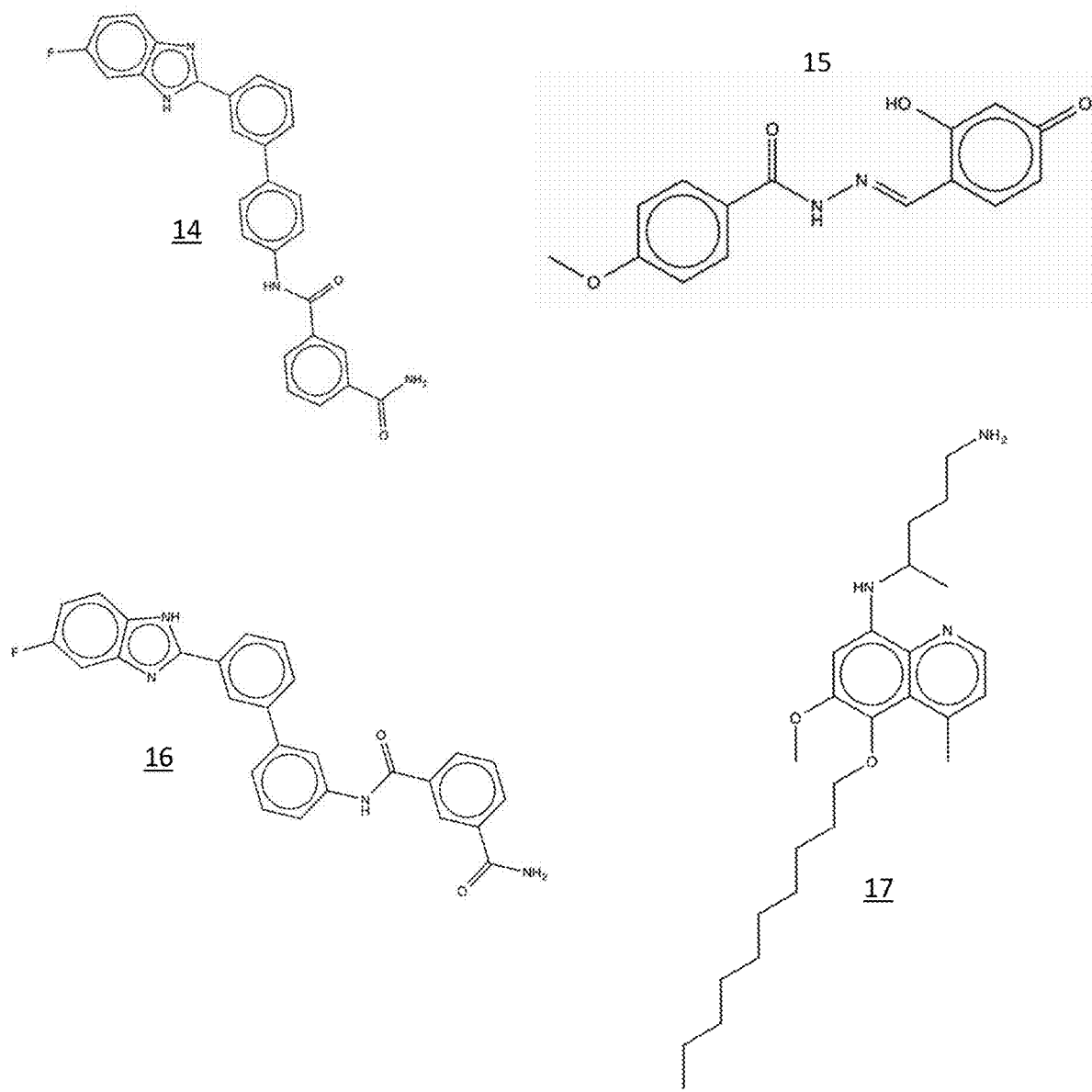
Figure 29E:
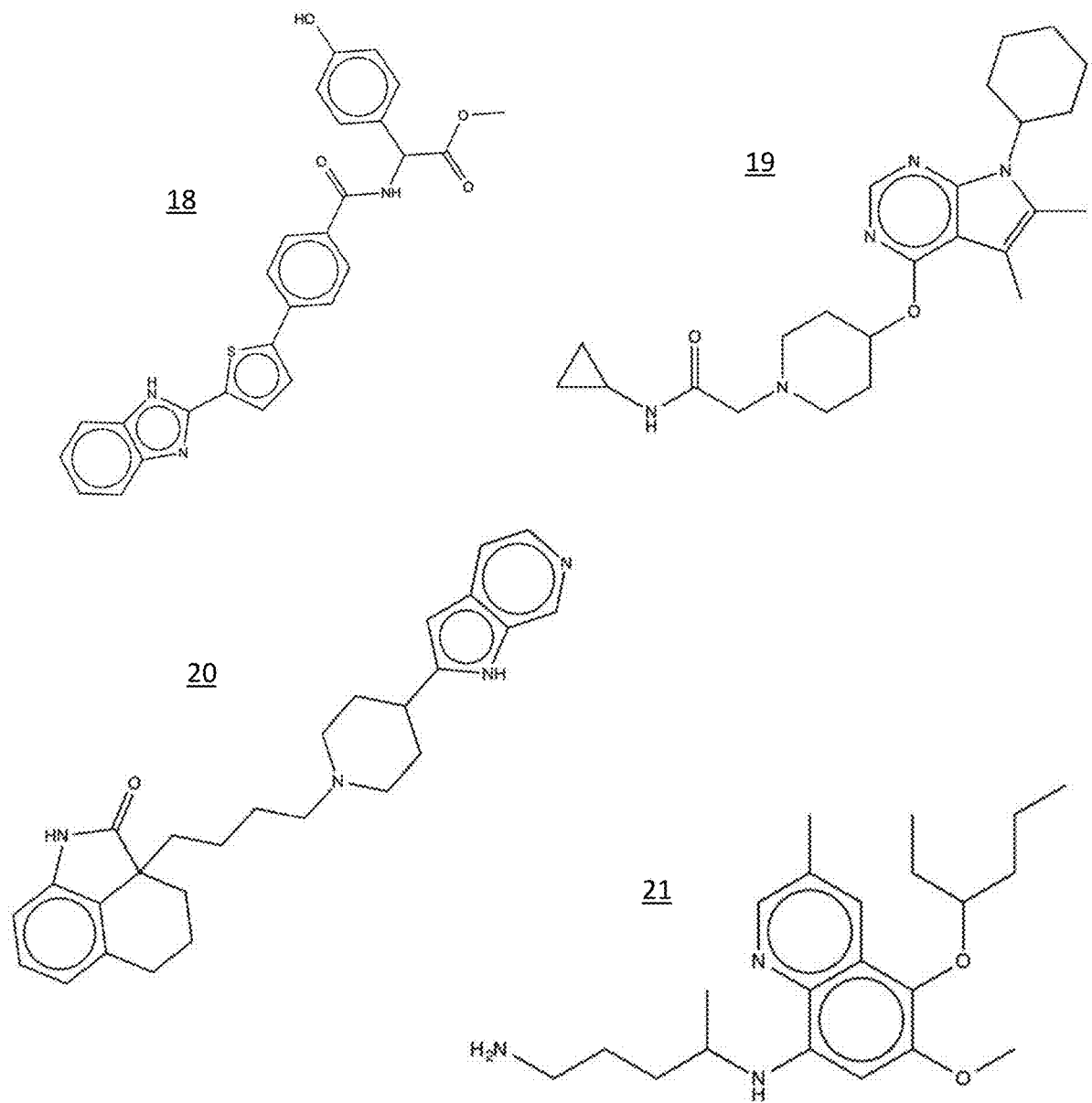

A total of 14 compounds from the GSK TCAMS dataset were obtained and tested in vitro to determine if they have antimalarial activity against the *P. berghei* blood stages. The assay was done at the following concentrations: 0.01 μM, 0.1 µM, 1 µM and 10 µM. Referring to FIG. 22 shows a growth inhibition against the *Plasmodium berghei* using the 14 GSK TCAMS compounds at 10 µM. It has been observed that seven of these compounds significantly inhibited the parasite growth by more than 50%, indicated by a red arrow in FIG. 22. The compounds, TCMDC-141151 and TCMDC-141221, are structurally the same. As shown in FIG. 22, it is observed that both the compounds present very similar parasite growth inhibition. Therefore, only TCMDC-141151 was used for further assays and identified as TCMDC-141151/TCMDC-141221. The six compounds that show more than 50% of parasite growth inhibition in the initial testing were the following: TCMDC-134945, TCMDC-124132, TCMDC-138323, TCMDC-132196, TCMDC-132198, TCMDC-141151/TCMDC-141221 (FIG. 22).

The results from the six compounds that presented antimalarial activity were verified in independent tests to assure accuracy of the growth inhibition curve ($EC_{50}$) against the *P. berghei* blood stages. Additional concentrations of the six compounds were used in the ITDL in order to obtain a dose response curve and $EC_{50}$ for each one. Referring to FIG. 23A-23E shows the GSK TCAMS compounds showing in vitro antimalarial activity. Four of the tested compounds, TCMDC-134945, TCMDC-124132, TCMDC-138323 and TCMDC-141151/TCMDC-141221, presented antimalarial activity ($EC_{50}$) at low micromolar concentration (FIGS. 23A-23D). The $EC_{50}$ values for each compound was: 1.48 µM for TCMDC-134945, 1.15 µM for TCMDC-124132, 3.03 µM for TCMDC-138323 and 1.04 µM for TCMDC-141151/TCMDC-141221 (FIG. 23E). The 95% confidence interval for the $LogEC_{50}$ of each inhibitor is reported in FIG. 23E. FIG. 25A-25D shows a proposed binding mode and interaction of GSK TCAMS compounds in the G and H binding pockets of the *P. berghei* glutathione S-transferase enzyme. As the compounds, TCMDC-132196 and TCMDC-132198, showed parasite growth inhibition close to the $EC_{50}$ cut off, they were tested again. FIG. 24A-24B shows a growth inhibition curves of the compounds TCMDC-132196 and TCMDC-132198. These results indicate that 4 out of 14 compounds tested in vitro have an effect at low micromolar concentration on the growth of the *P. berghei* blood stages.

Potential Activity of Three Compounds Against the *Plasmodium berghei* Glutathione S-Transferase:

The GST activity was determined in the blood stage protein extracts of the *P. berghei* (ANKA-GFP) parasites by increasing the absorption at 340 nm. This assay was standardized using the standard GST inhibitor, S-hexylglutathione, and the human placenta GST as a positive control. FIG. 26A-26D shows the glutathione S-transferase enzymatic activity in the presence of S-hexylglutathione. The $IC_{50}$ values of the standard GST inhibitor S-hexylglutathione was determined for the human placenta GST (41.27 µM) and the *P. berghei* GST (31.16 µM) as shown in FIGS. 26A and 26B. To demonstrate the potential inhibitory activity of S-hexylglutathione, different concentrations of the compound were used to determine the effect on activity of hGST and pbGST (FIGS. 26C and 26D). A 50% of inhibition activity was observed at 50 µM of S-hexylglutathione in both human placenta and *P. berghei* GSTs. Significant differences were observed in hGST which present inhibition of activity at 50 µM (**, p<0.0001) and 250 µM (**, p<0.0001) of S-hexylglutathione (FIG. 26C). In addition, the pbGST showed an inhibition effect that is reproducible at 50 µM and 250 µM, however, since n=2 a statistical analysis cannot be done (FIG. 26D).

Referring to FIG. 27A-27C shows the *Plasmodium berghei* Glutathione S-transferase potential inhibitory activity of the GSK TCAMS compounds. The GSK TCAMS compounds that shows in vitro antimalarial activity at low micromolar concentration (TCMDC-134945, TCMDC-124132, and TCMDC-141151/TCMDC-141221) were analyzed to verify the potential inhibition of the pbGST. No inhibitory activity was observed between the pbGST activity and the concentrations of the compounds TCMDC-134945 and TCMDC-141151 used (FIGS. 27A and 27C). A tendency of inhibition was observed in the pbGST using the TCMDC-124132 compound and a more marked effect is observed at 50 µM of TCMDC-124132 (FIG. 27B). Regardless that the effect of the compounds is reproducible, a statistical analysis cannot be done since n=2. This result suggests that compound TCMDC-124132 might have inhibitory activity on *P. berghei* GST at a concentration of 50 µM. FIG. 28A-28B shows a comparison of the effect of TCMDC-124132 compound in the Glutathione S-transferase activity of *Plasmodium berghei* and human. To confirm these results, a complete inhibition curve using various greater concentrations of the tested compound is done. The TCMDC-124132 compound was also assayed against the human placenta GST and similarly to pbGST a tendency of inhibition was observed at 50 µM and 100 µM. Statistical difference was observed in hGST at 100 µM (****, adjusted p value<0.0001) of TCMDC-124132 (FIG. 28B). Results indicate that TCMDC-134945 and TCMDC-141151/TCMDC-141221 compounds did not present inhibition against the *P. berghei* GST, providing evidence that GST is not the major target for the GSK TCAMS compounds tested. However, the TCMDC-124132 compounds present an effect against the pbGST and hGST and our results suggest that this compound have an effect against GST.

In an embodiment, the *Plasmodium* spp. GST was characterized and classified into the sigma class of GST. The *P. berghei* gst gene was characterized and reverse genetic approaches showed that this gene is essential during the blood stages. This result confirms that GST is a good target for the development of novel antimalarials compounds and reveals the importance of this detoxification enzyme for the survival of *P. berghei* erythrocytic stages. In another embodiment, the *P. berghei* gst gene was sequenced and partially characterized. The pbgst gene has an open reading frame of 808 nucleotides. Further, the *P. berghei* GST is used as a drug target. The specificity of three GSK TCAMS compounds (TCMDC-134945, TCMDC-124132, and TCMDC-141151/TCMDC-141221) was tested in a GST enzymatic assay. During the study it was found that TCMDC-124132 compound presented inhibitory activity in pbGST and hGST.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A method for treating malaria in a mammal, the method comprising: administering to a mammal a compound having formula (I):

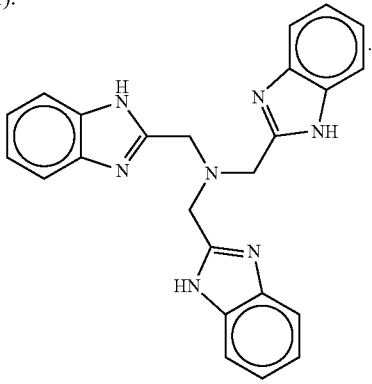

2. The method of claim 1, wherein the compound shows 50% of a maximal inhibition at 1.15 μM.

3. The method of claim 1, wherein the compound inhibits growth of a *plasmodium* malarial parasite.

4. The method of claim 3, wherein the malarial parasite is *Plasmodium berghei*.

5. The method of claim 3, wherein the malarial parasite is *Plasmodium falciparum*.

6. The method of claim 1, wherein the compound binds to a H-site of the glutathione S-transferase.

* * * * *